(12) United States Patent
Baker et al.

(10) Patent No.: US 9,790,196 B2
(45) Date of Patent: *Oct. 17, 2017

(54) LYSINE DEMETHYLASE INHIBITORS FOR DISEASES AND DISORDERS ASSOCIATED WITH FLAVIVIRIDAE

(71) Applicant: Oryzon Genomics, S.A., Cornellà de Liobregat, Barcelona (ES)

(72) Inventors: Jonathan A. Baker, Salt Lake City, UT (US); Matthew Collin Thor Fyfe, Chipping Norton (GB)

(73) Assignee: ORYZON GENOMICS S.A., Cornella de Llobregat, Barcelona (ES)

( * ) Notice: Subject to any disclaimer, the term of this patent is extended or adjusted under 35 U.S.C. 154(b) by 0 days.

This patent is subject to a terminal disclaimer.

(21) Appl. No.: 14/096,557

(22) Filed: Dec. 4, 2013

(65) Prior Publication Data

US 2014/0256742 A1 Sep. 11, 2014

Related U.S. Application Data

(63) Continuation of application No. 13/990,182, filed as application No. PCT/EP2011/071444 on Nov. 30, 2011, now abandoned.

(60) Provisional application No. 61/458,776, filed on Nov. 30, 2010.

(51) Int. Cl.

| A61K 31/135 | (2006.01) |
| A01N 33/02 | (2006.01) |
| C07D 295/195 | (2006.01) |
| A61K 31/165 | (2006.01) |
| A61K 31/495 | (2006.01) |
| A61K 45/06 | (2006.01) |
| C07C 215/64 | (2006.01) |
| C07C 237/20 | (2006.01) |

(52) U.S. Cl.
CPC ........ *C07D 295/195* (2013.01); *A61K 31/135* (2013.01); *A61K 31/165* (2013.01); *A61K 31/495* (2013.01); *A61K 45/06* (2013.01); *C07C 215/64* (2013.01); *C07C 237/20* (2013.01)

(58) Field of Classification Search
CPC . C07C 215/64; C07C 237/20; C07D 295/195; A61K 2300/00; A61K 31/135; A61K 31/165; A61K 31/495; A61K 45/06
USPC .................................. 514/255.01, 619, 647
See application file for complete search history.

(56) References Cited

U.S. PATENT DOCUMENTS

| 3,106,578 A | 10/1963 | Kaiser et al. |
| 3,365,458 A | 1/1968 | Biel et al. |
| 3,471,522 A | 10/1969 | Biel et al. |
| 3,532,712 A | 10/1970 | Biel et al. |
| 3,532,749 A | 10/1970 | Biel et al. |
| 3,758,684 A | 9/1973 | Elion et al. |
| 4,409,243 A | 10/1983 | Lieb |
| 4,522,811 A | 6/1985 | Eppstein et al. |
| 4,530,901 A | 7/1985 | Weissmann |
| 6,043,393 A | 3/2000 | de Meijere et al. |
| 6,211,244 B1 | 4/2001 | Van Wagenen et al. |
| 6,337,074 B1 | 1/2002 | Marsden et al. |
| 6,809,120 B1 | 10/2004 | Warrington et al. |
| 7,399,825 B2 | 7/2008 | Lipps et al. |
| 7,611,704 B2 | 11/2009 | Thorpe et al. |
| 7,628,993 B2 | 12/2009 | Vilalta et al. |
| 7,799,782 B2 | 9/2010 | Munson et al. |
| 8,524,717 B2 | 9/2013 | Guibourt et al. |
| 8,722,743 B2 | 5/2014 | Ortega-Munoz et al. |
| 8,859,555 B2 | 10/2014 | Ortega-Munoz et al. |
| 8,946,296 B2 | 2/2015 | Ortega Muñoz et al. |
| 8,993,808 B2 | 3/2015 | Guibourt et al. |
| 9,006,449 B2* | 4/2015 | Fyfe ..................... C07C 211/40 546/276.4 |
| 9,061,966 B2 | 6/2015 | Laria et al. |
| 9,149,447 B2 | 10/2015 | Ortega Muñoz et al. |
| 9,181,198 B2 | 11/2015 | Ortega Muñoz et al. |
| 9,186,337 B2* | 11/2015 | Baker .................. A61K 31/131 |
| 2003/0008844 A1 | 1/2003 | Spero et al. |
| 2003/0236225 A1 | 12/2003 | Protopopova et al. |
| 2004/0019117 A1 | 1/2004 | Protopopova et al. |
| 2004/0033986 A1 | 2/2004 | Protopopova et al. |
| 2004/0048802 A1 | 3/2004 | Ripka et al. |
| 2004/0132820 A1 | 7/2004 | Gosselin et al. |
| 2004/0147741 A1 | 7/2004 | Sundermann et al. |
| 2004/0162287 A1 | 8/2004 | Sundermann et al. |
| 2004/0176469 A1 | 9/2004 | Thomas |
| 2004/0229872 A1 | 11/2004 | Friderichs et al. |

(Continued)

FOREIGN PATENT DOCUMENTS

| EP | 1193268 | 4/2002 |
| EP | 1704859 | 9/2006 |

(Continued)

OTHER PUBLICATIONS

CDC (Centers for Disease Control and Prevention), "Viral Hepatitis—Hepatitis C Information", May 31, 2015, http://www.cdc.gov/hepatitis/hcv/.*
Ahmed et al. "Ticagreior: a new reversible oral antiplatelet agent" Int Research Journal of Pharmacy, 2010, 1(1), 62-69.
Arya et al, "Synthesis of 5H-dibenzo[a,d]cycloheptene derivatives with diverse biological activities", Indian J Chemistry B, 1978, 16B,220-225.
Bar-Am et al, "Regulation of Bcl-f family proteins, neurotrophic factors, and APP processing in the neurorescue activity of propargylamine". FASEB J, 2005, 19(13), 1899-1901.
Barlesi et al, "Global histone modifications predict prognosis of resected non small-cell lung cancer",J Clin Oncol,2007,25, 4358-4364.
Benelkebir et al, "Enantioselective synthesis of tranycypromine analogues as lysine demethylase (LSD1) inhibitors", Bioorg Med Chem, 2011, 19(12),3709-3716.

(Continued)

*Primary Examiner* — My-Chau T Tran
(74) *Attorney, Agent, or Firm* — Finnegan, Henderson, Farabow, Garrett & Dunner, LLP

(57) ABSTRACT

The invention relates to methods and compositions for the treatment or prevention of Flaviviridae infections. In particular, the invention relates to an LSD1 inhibitor for use in treating or preventing Flaviviridae infections, including hepatitis C virus infections.

15 Claims, 4 Drawing Sheets

(56) References Cited

U.S. PATENT DOCUMENTS

| | | | |
|---|---|---|---|
| 2004/0254158 A1 | 12/2004 | Qiao et al. | |
| 2005/0009832 A1 | 1/2005 | Sun et al. | |
| 2005/0154056 A1 | 7/2005 | Yang et al. | |
| 2006/0116370 A1 | 6/2006 | Dollinger et al. | |
| 2006/0148904 A1 | 7/2006 | Protopopova et al. | |
| 2006/0211709 A1 | 9/2006 | Buhr et al. | |
| 2006/0270673 A1 | 11/2006 | Duggan et al. | |
| 2006/0275366 A1 | 12/2006 | Malcolm et al. | |
| 2006/0287287 A1 | 12/2006 | Gerritz et al. | |
| 2007/0213338 A1 | 9/2007 | Lebsack et al. | |
| 2008/0139665 A1 | 6/2008 | Schuele et al. | |
| 2008/0242698 A1 | 10/2008 | Flor et al. | |
| 2008/0269228 A1 | 10/2008 | Moore et al. | |
| 2009/0203750 A1 | 8/2009 | Kozikowski et al. | |
| 2009/0247530 A1 | 10/2009 | Nolte et al. | |
| 2010/0016262 A1 | 1/2010 | Mehal et al. | |
| 2010/0240649 A1 | 9/2010 | Zhang | |
| 2010/0292225 A1 | 11/2010 | Chamoin et al. | |
| 2010/0324147 A1 | 12/2010 | McCafferty et al. | |
| 2012/0202810 A1 | 8/2012 | Nolte et al. | |
| 2013/0095067 A1* | 4/2013 | Baker | A61K 31/131 424/85.4 |
| 2013/0197095 A1 | 8/2013 | Nolte et al. | |
| 2013/0274267 A1* | 10/2013 | Cesar Castro Palomino Laria | A61K 31/13 514/252.12 |
| 2013/0303545 A1* | 11/2013 | Maes | A61K 31/00 514/255.01 |
| 2014/0163041 A1* | 6/2014 | Fyfe | A61K 31/00 514/255.01 |
| 2014/0296255 A1* | 10/2014 | Maes | A61K 31/135 514/255.01 |
| 2014/0329833 A1* | 11/2014 | Maes | A61K 31/135 514/255.01 |
| 2015/0025054 A1* | 1/2015 | Ortega Munoz | C07D 309/04 514/210.01 |
| 2015/0065434 A1* | 3/2015 | Woster | A61K 38/1709 514/19.9 |
| 2015/0119396 A9* | 4/2015 | Ortega Munoz | C07C 271/24 514/237.8 |
| 2015/0232436 A1* | 8/2015 | Baker | C07D 295/195 514/255.01 |

FOREIGN PATENT DOCUMENTS

| | | |
|---|---|---|
| EP | 1741708 | 1/2007 |
| EP | 2233495 | 9/2010 |
| GB | 1307341 | 2/1973 |
| JP | 2001354563 | 12/2001 |
| SU | 230169 | 10/1968 |
| WO | WO94/27947 | 12/1994 |
| WO | WO96/38141 | 12/1996 |
| WO | WO98/18459 | 5/1998 |
| WO | WO99/05142 | 2/1999 |
| WO | WO99/05143 | 2/1999 |
| WO | WO99/31072 | 6/1999 |
| WO | WO99/54440 | 10/1999 |
| WO | WO99/67203 | 12/1999 |
| WO | WO00/34283 | 6/2000 |
| WO | WO01/92264 | 12/2001 |
| WO | WO02/079152 | 10/2002 |
| WO | WO03/087064 | 10/2003 |
| WO | WO03/093297 | 11/2003 |
| WO | WO03/096989 | 11/2003 |
| WO | WO2004/020415 | 3/2004 |
| WO | WO2004/055010 | 7/2004 |
| WO | WO2004/062601 | 7/2004 |
| WO | WO2004/065367 | 8/2004 |
| WO | WO2004/072086 | 8/2004 |
| WO | WO2005/009941 | 2/2005 |
| WO | WO2005/023761 | 3/2005 |
| WO | WO2005/025558 | 3/2005 |
| WO | WO2005/037843 | 4/2005 |
| WO | WO2005/058808 | 6/2005 |
| WO | WO2005/058883 | 6/2005 |
| WO | WO2005/058884 | 6/2005 |
| WO | WO2005/103003 | 11/2005 |
| WO | WO2006/071608 | 7/2006 |
| WO | WO2006/087206 | 8/2006 |
| WO | WO2007/000248 | 1/2007 |
| WO | WO2007/005896 | 1/2007 |
| WO | WO2007/015824 | 2/2007 |
| WO | WO2007/025144 | 3/2007 |
| WO | WO2007/025709 | 3/2007 |
| WO | WO2007/021839 | 7/2007 |
| WO | WO2007/106016 | 9/2007 |
| WO | WO2007/134799 | 11/2007 |
| WO | WO2008/033466 | 3/2008 |
| WO | WO2008/116156 | 9/2008 |
| WO | WO2008/127734 | 10/2008 |
| WO | WO2009/001132 | 12/2008 |
| WO | WO2009/023179 | 2/2009 |
| WO | WO2009/039134 | 3/2009 |
| WO | WO2009/052078 | 4/2009 |
| WO | WO2009/097278 | 8/2009 |
| WO | WO2009/109991 | 9/2009 |
| WO | WO2009/117515 | 9/2009 |
| WO | WO2009/145856 | 12/2009 |
| WO | WO2009/153197 | 12/2009 |
| WO | WO2010/011845 | 1/2010 |
| WO | WO2010/014921 | 2/2010 |
| WO | WO2010/030592 | 3/2010 |
| WO | WO2010/043721 | 4/2010 |
| WO | WO2010/084160 | 7/2010 |
| WO | WO2010/085749 | 7/2010 |
| WO | WO2010/099527 | 9/2010 |
| WO | WO2010/139784 | 12/2010 |
| WO | WO2010/143582 | 12/2010 |
| WO | WO2011/022489 | 2/2011 |
| WO | WO2011/031934 | 3/2011 |
| WO | WO2011/035941 | 3/2011 |
| WO | WO2011/042217 | 4/2011 |
| WO | WO2011/057262 | 5/2011 |
| WO | WO2011/106105 | 9/2011 |
| WO | WO2011/106106 | 9/2011 |
| WO | WO2011/113005 | 9/2011 |
| WO | WO2011/131576 | 10/2011 |
| WO | WO2011/131697 | 10/2011 |
| WO | WO2011/132083 | 10/2011 |
| WO | WO2012/001531 | 1/2012 |
| WO | WO2012/013727 | 2/2012 |
| WO | WO2012/013728 | 2/2012 |
| WO | WO2012/034116 | 3/2012 |
| WO | WO2012/042042 | 4/2012 |
| WO | WO2012/045883 | 4/2012 |
| WO | WO2012/107498 | 8/2012 |
| WO | WO2012/107499 | 8/2012 |
| WO | WO2012/135113 | 10/2012 |
| WO | WO2012/156531 | 11/2012 |
| WO | WO2012/156537 | 11/2012 |
| WO | WO2013/057320 | 4/2013 |
| WO | WO2013/057322 | 4/2013 |

OTHER PUBLICATIONS

Biljak et al,"Platelet count, mean platelet volume and smoking status in stable chronic obstructive pulmonary disease", Platelets, 2011,22(6), 466-70.

Binda et al, "Biochemical, structural, and biological evaluation of tranylcypromine derivatives as inhibitors of histone demethylases LSD1 and LSD2", J Am Chem Soc,2010,132(19),6827-6833.

Bisi et al, "Multidrug resistance reverting activity and antitumor profile of new phenothiazine derivatives", Bioorg Med Chem, 2008, 16(13), 6474-6482.

Boilard et al, "Platelets amplify inflammation in arthritis via collagen-dependent microparticle production", Science, 2010,327(5965), 580-583.

Bolesov et al, "Cyclopropanes and cyciabutanes LXIX", Zhurnal Organicheskoi Khimii (English Translation), 1974, 10(10), 2122-2128.

Bolesov et al, "Cyclopropanes and cyclobutanes LXVIII. N-mono and N,N-disubstituted 1-amino-2-phenyicyclopropanes",Zhurnal Organicheskoi Khimii (English Translation), 1974, 10(6), 1678-84.

(56) References Cited

OTHER PUBLICATIONS

Brand and Perrimon, "Targeted gene expression as a means of altering cell fates and generating dominant phenotypes", 1993, Development, 118, 401-415.
Brydon et al, "Platelets, coronary heart disease and stress", Brain, Behavior and Immunity,2006, 20(2), 113-119.
Burakova et al, "N- and O-alkylation of 3-indolylcyclopropylacetic acid derivatives", Russian Chemical Bulletin, 2002, 51(10) 1829-1840.
Burk et al, "Cognitive deficits in spinocerebellar ataxia 2", Brain, 1999, 122(4), 769-777.
Cakmak et al, "Platelets: indicator of inflammation in CORP", Int J Med Med Sci, 2009. 1(5), 227-229.
Calogero et al, "Inhibition of cell growth by EGR-1 in human primary cultures from malignant glioma",Cancer Cell International,2004,4, 1.
Casero et al, "Recent advances in the development of polyamine analogues as antitumor agents", J Med Chem, 2009, 52(15),4551-4573.
Chen et al, "Association of insulin resistance and hematologic parameters: study of a middle-aged and elderly Chinese population in Taiwan", J Chin Med Assoc,2006, 69(6), 248-253.
Chimenti et al "Synthesis, Stereochemical Identification, and Selective Inhibitory Activity against Human Monoamine Oxidase-B of 2-Methylcyclohexylidene-(4-arylthiazol-2-yl)hydrazones", (2008) J. Med. Chem. 51 (16), 4874-4880.
Choi et al "Histone demethylase LSD1 is required to induce skeletal muscle differentiation by regulating myogenic factors" (2010) Biochemical and Biophysical Research Communications 401(3), 327-332.
Choo et al, "Genetic organization and diversity of the hepatitis C virus", Proc Natl Acad Sci,1991,88,2451-2455.
Culhane et al, A mechanism-based inactivator for histone demethylase LSD1, J Am Chem Soc, 2006, 128(14), 4536-4537.
Culhane et al, "Comparative analysis of small molecules and histone substrate analogues as LSD1 lysine demethylase inhibitors", J Am Chem Soc, 2010,132(9),3164-3176.
Danese et al, "Platelets in inflamatory bowel disease: clinical, pathogenic and therapeutic implications", Am J Gastroenterol, 2004,99(5), 938-45.
Di Stefano et al, Mutation of *Drosophila* Lsd1 disrupts H3-K4 methylation, resulting in tissue-specific defects during development, Curr Biol,2007 17(9), 808-12.
East et al, "An orally bioavailable positive allosteric modulator of the mGlu4 receptor with efficacy in an animal model of motor dysfunction", Bioorg Med Chem Lett, 2010, 20(16), 4901-5.
Ellis et al, "Expression of *Drosophila* glass protein and evidence for negative regulation of its activity in non-neuronal cells by another DNA-binding protein",Development,1993, 119, 855-865.
Elsheikh et al "Global histone modifications in breast cancer correlate with tumor phenotypes, prognostic factors and patient outcome", Canc Res. 2009,69, 3802-3809.
Erazo et al, "Varicella-zoster virus open reading frame 66 protein kinase is required for efficient viral growth in primary human corneal stromal fibroblast cells", J Virol, 2008,82, 7553-7665.
Faler et al, "The Kulinkovich reaction in the snythesis of constrained N,N-dialkyl neurotransmitter analogues", Organic Letters 2007 ,9(10), 1987-1990.
Ferlay et al, "Estimates of the cancer incidence and mortality in Europe in 2006", Annals of Oncology 2007, 18(3), 581-92.
Ferraro et al, "EGR1 predicts PTEN and survival in patients with non-small-cell lung cancer", J Clin Oncol, 2005, 23(9), 1921-26.
Fischer et al, "Recovery of learning and memory is associated with chromatin remodelling", Nature, 2007,447, 178-182.
Forneris et al "LSD1: oxidative chemistry for multifaceted functions in chromatin Regulation." Trends in Biochemical Sciences 2008,33(4), 181-189.
Gawaz et al, "Platelets in inflammation and atherogenesis", J Clin Invest, 2005,115(12), 3378-3384.
Gooden et al, "Facile synthesis of substituted trans-2-arylcyclopropylamine inhibitors of the human histone demethylase LSD1 and monoamine oxidases A and B", Bioorg Med Chem Lett 2008, 18(10), 3047-51.
Han et al "Modulation of breast cancer resistance protein (BCRP/ABCG2) by non-basic chalcone analogues" Eur. J. Pharma. 2008, 35(1-2) 30-41.
Han et al, "Antidepressants reveal differential effect against 1-methyl-4-phenylpyridinium toxicity in differentiated PC12 cells", Eur J Pharmacol, 2009, 604 (1-3),36-44.
Hayami et al, "Overexpression of LSD1 contributes to human carcinogenesis through chromatin regulation in various cancers", Int J Cancer, 2011, 128(3), 574-86.
Hruschka et al, "Fluorinated phenylcyclopropylamines. Part 5:Effect of electron-withdrawing or- donating aryl substituents on the inhibition of monoamine oxidases A and B by 2-aryl-2-fluoro-cyclopropylamines", Bioorg Med Chem,2008, 16(15), 7148-7166.
Huang et al, "Novel oligoamine analogues inhibit lysine-specific demethylase 1 (LSD1) and induce re-expression of epigeneticall silenced genes",Clin Cancer Res,2009, 15(23), 7217-28.
Huang et al, "p53 is regulated by the lysine demethylase LSD1",Nature,2007,449, 105-108.
Huang et al,"Inhibition of lysine-specific demethylase 1 by polyamine analogues results in reeexpression of aberrantly silenced genes", PNAS,2007, 104(19), 8023-8028.
Jackson et al, "Polyglutamine-expanded human Huntingtin transgenes induce degeneration of *Drosophila* photoreceptor neurons", Neuron, 1998, 21, 633-642.
Kahl et al,"Androgen receptor coactivators lysine-specific histone demethylase 1 and four and a half LIM domain protein 2 predict risk of prostate cancer recurrence", Cancer Res,2006,66 (23), 11341-11347.
Kaiser et al, "2-substituted cyclopropylamines. I. Derivatives and analogs of 2-phenylcyclopropylamine", J Med Pharm Chem (ACS), 1962, 5, 1243-1265.
Kiefmann et al, "Red blood cells induce hypoxic lung inflammation", Blood, 2008,111(10),5205-14.
Kim et al, "Flavin chemical models for monoamine oxidase inactivation by cyclopropylamines, α-silylamines, and hydrazines", J Am Chem Soc 1995, 117, 100-105.
Kinzel et al, "Identification of MK-5710 ((8aS)-8a-methyl-1,3-dioxo-2-[(1S,2R)-2-phenylcyclopropyl]-N-(1-phenyl-1H-pyrazol-5-yl)hexahydro-imidazo[1,5-a]pyrazine-7-(1H)-carboxamide), a potent smoothened antagonist for use in Hedgehog pathway dependent malignancies. Part 2", Biorg Med Chem Lett 2011, 21(15), 4429-4435.
Kornerup et al, "The role of platelets in the pathophysiology of asthma" Platelets, 2007,18(5), 319-28.
Krieger et al, "Enhancement of hepatitis C virus RNA replication by cell culture-adaptive mutations", J Virol, 2001,75, 4614-4624.
Lan et al "Mechanisms involved in the regulation of histone lysine demethylases", Current Opinion in Cell Biology, 2008,20, 316-325.
Lee et al, "Combinatorial lead optimization of [1,2]-diamines based on ethambutol as potential antituberculosis preclinical candidates", J Comb Chem, 2003, 5(2), 172-187.
Lee et al, "Histone H3 lysine 4 demethylation is a target of nonselective antidepressive medications",Chem Biol, 2006,13(6), 563-567.
Li et al, "Association between inflammatory mediators and angiographic morphologic features indicating thrombus formation in patients with acute myocardial infarction", Chin Med J. 2009,122(15), 1738-42.
Liang et al, "Inhibition of the histone demethylase LSD1 blocks alpha-herpesvirus lytic replication and reactiviation from latency",Nat Med, 2009, 15 (11), 1312-1317.
Lim et al, "Lysine-specific demethylase 1 (LSD1) is highly expressed in ER-negative breast cancers and a biomarker predicting aggressive biology", Carcinogenesis,2010, 31(3), 512-20.
Lucerna et al, "Sustained expression of early growth response protein-1 blocks agiogenesis and tumor growth",Cancer Research,2006, 66,6708-6713.
Lupu Roxana, "Up-to-date in the hematological malignancies treatment", Maedica, 2006,1(1), 63-65.

(56) References Cited

OTHER PUBLICATIONS

Maclay et al, "Increased platelet activation in patients with stable and acute exacerbation of COPD", Thorax, 2011,66(9), 769-74.
Mannaioni et al, "Platelets and inflammation: role of platelet-derived growth factor, adhesion molecules and histamine", Inflamm Res, 1997,46(1), 4-18.
McNicol et al, "Beyond hemostasis: the role of platelets in inflammation, malignancy and infection",Cardiovascular & Haematological Disorders-Drug Targets, 2008,8, 99-117.
Meanwell, "Synopsis of some recent tactical application of bioisosteres in drug design", J Med Chem, 2011, 54(8),2529-91.
Metzger et al, "LSD1 demethylates repressive histone marks to promote androgen-receptor-dependent transcription",Nature, 2005, 437(7057),436-9.
Mimasu et al, "Crystal structure of histone demethylase LSD1 and tranylcypromine at 2.25 A" Biochemical and Biophysical Research Communications ,2008,366, 15-22.
Mimasu et al, "Structurally designed trans-2-phenylcyclopropylamine derivatives potently inhibit histone demethylase LSD1/KDM1", Biochemistry,2010,49(30), 6494-6503.
Moritani et al, "Activation of platelets in bronchial asthma", Chest., 1998, 113, 452-458.
Nabil Aboul-Enein et al, "Synthesis of some 4-substituted amino-1-methylpiperidines structurally related to anithistaminics", Pharmaceutica Acta Helvetiae, 1973, 48(3): 151-156.
Neelamegan et al, "Brain-penetrant LSD1 inhibitors can block memory consolidation", ACS Chem Neurosci, 2012, 3(2), 120-128.
Ogasawara et al, "Synthesis and biological activity of optically active NCL-1, a lysine-specific demethylase 1 selective inhibitor",Bioorg Med Chem, 2011, doi:10.1016/j.bmc.2010.12.024.
O'Sullivan et al, "The inflammatory role of platelets in cystic fibrosis", Am J Respir Crit Care Med, 2006,173, 483-90.
Pannala et al "Synthesis and structure-activity relationship of 4-(2-aryl-cyclopropylamino)-quinoline-3-carbonitriles as EGFR tyrosine kinase inhibitors". Bioorg & Med Chem Lett , 2007,17(21), 5978-5082.
Pitchford et al, "Platelet P-selectin is required for pulmonary eosinophil and lymphocyte recruitment in a murine model of allergic inflammation", Blood, 2005,105, 2074-2081.
Pollock et al, Lysine-specific histone demethylase 1 inhibitors control breast cancer proliferation in ERalpha-dependent and -independent manners, ACS Chem Biol 2012,7, 1221-1231.
Ravina et al, "The relationship between CAG repeat length and clinical progression in Huntington's disease", Movement Disorders,2008,23(9), 1223-7.
Reddy et al, "Role of lysine-specific demethylase 1 in the proinflammatory phenotype of vascular smooth muscle cells of diabetic mice",Circ Res,2008,103, 615-23.
Riley et al, "Absolute configuration of (+)- and (−)-trans-2-phenylcyclopropylamine hydrochloride",J Med Chem, 1972,15(11), 1187-1188.
Ringer et al, "Correlation of thrombosis with increased platelet turnover in thrombocytosis", Blood, 1998,91(4), 1288-1294.
Schmidt et al,"trans-2-phenylcyclopropylarnine is a mechanism-based inactivator of the histone demethylase LSD1", Biochemistry, 2007,46(14),4408-4416.
Schulte et al, "Lysine-specific demethylase 1 is strongly expressed in poorly differentiated neuroblastoma: implications for therapy", Cancer Res,2009,69(5),2065-71.
Scoumanne et al "Protein methylation: a new mechanism of p53 tumor suppressor regulation" Histol Histopathol 2008,23, 1143-1149.
Scoumanne et al, "The lysine-specific demethylase 1 is required for cell proliferation in both p53-dependent and -independent manners", J Biol Chem, 2007,282(21), 15471-5.
Seligson et al, "Global histone modification patterns predict risk of prostate cancer recurrence",Nature, 2005,435, 1262-1266.

Seligson et al,"Global levels of histone modifications predict prognosis in different cancers",Am J Path, 2009,174,1619-28.
Sharma et al, "(Bis)urea and (bis)thiourea inhibitors of lysine-specific demethylase 1 as epigenetic modulators", J Med Chem, 2010,53(14), 5197-5212.
Shi et al,"Histone demethylation mediated by the nuclear amine oxidase homolog LSD1", Cell, 2004,119,941-953.
Shi, "Histone lysine demethylases: emerging roles in development, physiology and disease", Nature Reviews Genetics 2007, 8:829-833.
Stephens et al, "The determination of the absolute configurations of chiral molecules using vibrational circular dichcroism (VCD) spectroscopy",Chirality, 2008,20(5), 643-663.
Stoffel et al, "Leukocyte count and risk of thrombosis in patients undergoing haematopoietic stem cell transplantation of intensive chemotherapy",Thromb Haemost, 2010,103(6), 1228-32.
Stratmann et al, "Pathobiology and cell interactions of platelets in diabetes", Diabetes & Vascular Disease Research,2005, 2(1), 16-23.
Szewczuk et al, "Mechanistic analysis of a suicide inactivator of histone demethylase LSD1", Biochemistry, 2007,46, 6892-6902.
Tamagawa-Mineoka et al, "Elevated platelet activation in patients with atopic dermatitis and psoriasis: increased plasma levels of beta-thromboglobulin and platelet factor 4", Allergology International,2008, 57, 391-396.
Taylor et al,"Roscovitine, a cyclin-dependent kinase inhibitor, prevents replication of varicella-zoster virus", J Virol, 2004,78, 2853-2862.
Thaulow et al, "Blood platelet count and function are related to total and cardiovascular death in apparently healtht men", Circulation, 1991,84, 613-617.
Ueda et al, "Identification of cell-active lysine specific demethylase 1-selective inhibitors",J Am Chem Soc, 2009, 131(48), 17536-17537.
Vagner et al, "Peptidomimetics, a synthetic tool of drug discovery", Current Opinion on Chemical Biology, 2008, 12:292-296.
Wagner et al, "Platelets in inflammation and thrombosis", Arteriosclerosis, Thrombosis and Vascular Biology, 2003, 23, 2131-2137.
Wang et al, "Novel histone demethylase LSD1 inhibitors selectively target cancer cells with pluripotent stem cell properties," Cancer Research, 2011, 71(23):7238-49.
Wang et al "LSD1 is a Subunit of the NuRD Complex and Targets the Metastasis Programs in Breast Cancer" Cell 2009, 138, 660-672.
Wang et al, "The lysine demethylase LSD1 (KDM1) is required for maintenance of global DNA methylation", Nature Genetics, 2009, 41(1), 125-129.
Weinreb et al, "Novel neuroprotective mechanism of action of rasagiline is associated with its propargyl moiety: interaction of Bcl-2 family members with PKC pathway", Ann NY Acad Sci, 2005, 1053, 348-55.
Wermuth, "Molecular variations based on isosteric replacements", The Practice of Medicinal Chemistry (2nd edition), Academic Press, London, 2003, pp. 189-214.
Westland et al , "N-substituted derivatives of 2-aminoethanethiol and 2-hydraxinoethanethiol", JMedChem 1968, 11(4),824-829.
Whitlow et al,"Recruitment of the transcriptional coactivator HCF-1 to viral immediate-early promoters during initiation of reactivation from latency of herpes simplex virus type 1", J Virol, 2009,83(18):9591-5.
Willoughby et al, "Platelets and cardiovascular disease"Eur J Cardiovasc Nursing,2002,1, 273-288.
XP002568777 Database chemcats, database accession No. 2088922753, order No. kbsb-0063197, Aurora screening library, Aug. 20, 2009.
Yang et al "Structural Basis for the Inhibition of the LSD1 Histone Demethylase by the Antidepressant trans-2-Phenylcyclopropylamine" Biochemistry 2007,46 (27), 8058-8065.
Yang et al "Structural basis of histone demethylation by LSD1 revealed by suicide inactivation" Nature Structural & Molecular Biology 2007, 14(6), 535-539.
Yoshida et al, "Fluorinated phenylcyolopropsylamines. Part 3: inhibition of monoamine oxidase A and B",Bioorg Med Chem,2004,12(10),2645-2652.

(56) References Cited

OTHER PUBLICATIONS

Youdim et al, "Bifunctional drug derivatives of MAO-B inhibitor rasagiline and iron chelator VK-28 as a more effective approach to treatment of brain ageing and ageing neurodegenerative diseases", Mechanisms of Ageing and Development, 2005, 126: 317-326.
F. Zaragoza Dorwald "Side reactions in Organic Synthesis: a guide to successful synthesis design" Wiley-VCH Verlag GmbH & Co, KGaA, Wilenheim, Chapter 1, 2005.
Zirkle et al, "2-substituted cyclopropylamines. II. Effect of structure upon monoamine oxidase-inhibitory activity as measured in vivo by potentiation of tryptamine convulsions", J Med Pharm Chem (ACS). 1962, 5, 1265-84.
"Definition of Cancer"—MedicineNetcom Medical references for patients, http://www.medterms.com, 2005.
Johnson et al, CAPLUS, Document No. 157:576967, "Preparation of cyclopropylamines as LSD1 inhibitors in the treatment of cancer", 2012.
Delorme et al, HCAPLUS, Document No. 132:49802, "Preparation of 1-(N-substituted aminomethyl)-4-guanidinomethylcyclohexanes useful in pain management", 1999.
CAS Registry No. RN220351-33-7, entered STN Mar. 11, 1999.
CAS Registry No. RN844655-03-04, entered STN Mar. 9, 2005.
CAS Registry No. RN1248611-33-7, entered STN Oct. 29, 2010.
CAS Registry No. RN1248913-30-5, entered STN Nov. 1, 2010.
CAS Registry No. RN1248971-98-3, entered STN Nov. 1, 2010.
CAS Registry No. RN1250045-89-6, entered STN Nov. 1, 2010.
CAS Registry No. RN1250199-20-2, entered STN Nov. 1, 2010.
CAS Registry No. RN1250332-49-0, entered STN Nov. 1, 2010.
CAS Registry No. RN1251130-23-0, entered STN Nov. 3, 2010.
CAS Registry No. RN1270634-53-1, entered STN Mar. 27, 2011.
CAS Registry No. RN1273738-91-2, entered STN Apr. 3, 2011.
CAS Registry No. RN1274124-27-4, entered STN Apr. 3, 2011.
CAS Registry No. RN1274681-54-7, entered STN Apr. 4, 2011.
CAS Registry No. RN1280568-04-8, entred STN Apr. 15, 2011.
CAS Registry No. RN1280602-35-8, entered STN Apr. 15, 2011.
CAS Registry No. RN1281516-77-5, entered STN Apr. 17, 2011.
CAS Registry No. RN846596-02-9, entered STN Mar. 22, 2005.
CAS Registry No. RN848204-13-7, entered STN Apr. 11, 2005.
CAS Registry No. RN848732-87-6, entered STN Apr. 19, 2005.
CAS Registry No. RN848742-47-2, entered STN Apr. 19, 2005.
CAS Registry No. RN848753-47-9, entered STN Apr. 19, 2005.
CAS Registry No. RN903487-42-3, entered STN Aug. 23, 2006.
CAS Registry No. RN918305-55-2, entered STN Jan. 24, 2007.
CAS Registry No. RN959071-98-8, entered STN Dec. 20, 2007.
CAS Registry No. RN1026299-47-7, entered STN Jun. 8, 2008.
CAS Registry No. RN1157140-28-7, entered STN Jun. 14, 2009.
CAS Registry No. RN218057-33-0, entered STN Apr. 11, 2010.
CAS Registry No. RN1247564-27-7, entered STN Oct. 27, 2010.
CAS Registry No. RN1247717-42-5, entered STN Oct. 27, 2010.
CAS Registry No. RN124799947-4, entered STN Oct. 28, 2010.
CAS Registry No. RN1281556-75-9, entered STN Apr. 17, 2011.
CAS Registry No. RN1281596-19-7, entered STN Apr. 17, 2011.
CAS Registry No. RN1281615-78-8, entered STN Apr. 17, 2011.
CAS Registry No. RN1281856-83-4, entered STN Apr. 18, 2011.
CAS Registry No. RN1281886-96-1, entered STN Apr. 18, 2011.
CAS Registry No. RN1282014-65-6, entered STN Apr. 18, 2011.
CAS Registry No. RN1282165-83-6, entered STN Apr. 19, 2011.
CAS Registry No. RN1282245-50-4, entered STN Apr. 19, 2011.
CAS Registry No. RN1282292-27-6, entered STN Apr. 19, 2011.
CAS Registry No. RN1282425-35-7, entered STN Apr. 19, 2011.
CAS Registry No. RN1282679-60-0, entered STN Apr. 20, 2011.
CAS Registry No. RN1282773-23-2, entered STN Apr. 20, 2011.
CAS Registry No. RN1282804-36-7, entered STN Apr. 20, 2011.
CAS Registry No. RN1282928-27-1, entered STN Apr. 20, 2011.
CAS Registry No. RN1283337-81-4, entered STN Apr. 21, 2011.
CAS Registry No. RN1283356-05-7, entered STN Apr. 21, 2011.
CAS Registry No. RN1283449-65-9, entered STN Apr. 21, 2011.
CAS Registry No. RN1283533-13-0, entered STN Apr. 21, 2011.
CAS Registry No. RN1283662-53-2, entered STN Apr. 21, 2011.
CAS Registry No. RN1283728-98-2, entered STN Apr. 21, 2011.
CAS Registry No. RN1283887-44-4, entered STN Apr. 22, 2011.
CAS Registry No. RN1284036-80-1, entered STN Apr. 22, 2011.
CAS Registry No. RN1284049-14-4, entered STN Apr. 22, 2011.
CAS Registry No. RN1284310-21-9, entered STN Apr. 22, 2011.
CAS Registry No. RN1285070-57-6, entered STN Apr. 24, 2011.
CAS Registry No. RN1285129-34-1, entered STN Apr. 24, 2011.
CAS Registry No. RN1285144-86-6, entered STN Apr. 24, 2011.
CAS Registry No. RN1285176-99-9, entered STN Apr. 24, 2011.
CAS Registry No. RN1285178-46-2, entered STN Apr. 24, 2011.
CAS Registry No. RN1285235-05-3, entered STN Apr. 24, 2011.
CAS Registry No. RN1285348-65-3, entered STN Apr. 25, 2011.
CAS Registry No. RN1285612-69-2, entered STN Apr. 25, 2011.
CAS Registry No. RN1290805-79-6, entered STN May 6, 2011.
CAS Registry No. RN1290906-73-8, entered STN May 6, 2011.
CAS Registry No. RN1290912-35-4, entered STN May 6, 2011.
CAS Registry No. RN1290912-36-5, entered STN May 6, 2011.
CAS Registry No. RN1290949-23-3, entered STN May 6, 2011.
CAS Registry No. RN1290949-24-4, entered STN May 6, 2011.
CAS Registry No. RN1290949-25-5, entered STN May 6, 2011.
CAS Registry No. RN1290971-74-2, entered STN May 6, 2011.
CAS Registry No. RN1290972-32-5, entered STN May 6, 2011.
CAS Registry No. RN1291186-57-6, entered STN May 8, 2011.
CAS Registry No. RN1291186-59-8, entered STN May 8, 2011.
CAS Registry No. RN1291186-62-3, entered STN May 8, 2011.
CAS Registry No. RN1291186-64-5, entered STN May 8, 2011.
CAS Registry No. RN1291230-78-8, entered STN May 8, 2011.
CAS Registry No. RN1291273-81-8, entered STN May 8, 2011.
CAS Registry No. RN1291273-82-9, entered STN May 8, 2011.
CAS Registry No. RN1291273-84-1, entered STN May 8, 2011.
CAS Registry No. RN1291273-86-3, entered STN May 8, 2011.
CAS Registry No. RN1291273-87-4, entered STN May 8, 2011.
CAS Registry No. RN1292446-11-7 entered STN May 10, 2011.
CAS Registry No. RN1304214-87-6, entered STN Jun. 2, 2011.
GAS Registry No. RN1304214-96-7, entered STN Jun. 2, 2011.
CAS Registry No. RN1304214-97-8, entered STN Jun. 2, 2011.
CAS Registry No. RN1304215-06-2, entered STN Jun. 2, 2011.
CAS Registry No. RN1304827-17-5, entered STN Jun. 3, 2011.
CAS Registry No. RN1304845-37-1, entered STN Jun. 3, 2011.
CAS Registry No. RN1304845-55-3, entered STN Jun. 3, 2011.
CAS Registry No. RN1304845-63-3, entered STN Jun. 3, 2011.
CAS Registry No. RN1304845-67-7, entered STN Jun. 3, 2011.
CAS Registry No. RN1304845-70-2, entered STN Jun. 3, 2011.
CAS Registry No. RN1304845-72-4, entered STN Jun. 3, 2011.
CAS Registry No. RN1304845-83-7, entered STN Jun. 3, 2011.
CAS Registry No. RN1305397-75-4, entered STN Jun. 5, 2011.
CAS Registry No. RN1305397-86-7, entered STN Jun. 5, 2011.
CAS Registry No. RN1305398-16-6, entered STN Jun. 5, 2011.
CAS Registry No. RN1306275-88-6, entered STN Jun. 5, 2011.
CAS Registry No. RN1306275-95-5, entered STN Jun. 5, 2011.
CAS Registry No. RN1306276-35-8, entered STN Jun. 5, 2011.
CAS Registry No. RN1306322-57-5, entered STN Jun. 6, 2011.
CAS Registry No. RN1306373-68-1, entered STN Jun. 6, 2011.
CAS Registry No. RN1306589-39-8, entered STN Jun. 6, 2011.
CAS Registry No. RN1307573-60-9, entered STN Jun. 8, 2011.
CAS Registry No. RN1307574-08-8, entered STN Jun. 8, 2011.
International Search Report and Written Opinion of the International Searching Authority for PCT/EP2011/071444 dated Feb. 2, 2013.

\* cited by examiner

A)

B)

LYSINE DEMETHYLASE INHIBITORS FOR DISEASES AND DISORDERS ASSOCIATED WITH FLAVIVIRIDAE

This application is a continuation of U.S. patent application Ser. No. 13/990,182, filed May 29, 2012, which is a national stage filing under 35 U.S.C. §371 of International Application No. PCT/EP2011/071444, filed on Nov. 30, 2011, and claims the benefit of U.S. Provisional Application No. 61/458,776, filed Nov. 30, 2010, all of which are incorporated herein by reference.

FIELD OF THE INVENTION

The invention relates to methods and compositions for the treatment or prevention of diseases and disorders associated with Flaviviridae and in particular hepatitis C virus infection and viral hepatitis. The invention also relates to an LSD1 inhibitor for use in treating or preventing diseases and disorders associated with Flaviviridae and in particular hepatitis C virus infection and viral hepatitis.

BACKGROUND OF THE INVENTION

One of the most dangerous and insidious classes of viruses that has enormous economic impact in terms of health care costs and associated burdens is the Flaviviridae which include the well know hepatitis C virus (HCV) which cause significant health problems world-wide, as well as other viruses such as West Nile Virus (WNV) and Dengue or Yellow Fever virus which can be deadly with the potential for catastrophic epidemics.

The Flaviviridae are characterized as being positive sense single stranded RNA viruses that have a genome of about 10 Kb that generally encodes one long ORF composed of a number of genes that are transcribed as a large polyprotein. The large polyprotein is processed to yield different enzymatic and structural proteins which go on to assist in RNA replication and viral propagation with the assistance of host cell factors. It is thought that the lifecycle of Flaviviridae does not go through replicative DNA intermediates.

Disease caused by hepatitis C virus is an enormous burden on the world's health systems. HCV is a major cause of liver disease throughout the world. It is estimated that upwards of 10,000 deaths per year are attributable to HCV in the United States. About four million people in the United States have antibodies to HCV. It is estimated that well over 150 million people worldwide are chronically infected with HCV. Chronic hepatitis C can cause hepatitis, cirrhosis, liver failure, and liver cancer (hepatocellular carcinoma). There are a variety of subtypes of HCV including at least 6 major genotypes and 50 subtypes. As with many other viruses, HCV is known to mutate quickly, and changes in the envelope protein may help the virus avoid the immune system of the host.

Efforts to combat HCV have been met with limited success. Vaccines and immunoglobulin products for preventing HCV have been in development but are not currently available. Given the rapidly mutating nature of the virus and the variety of variants of HCV, it is a daunting task and if possible, it will likely take a long time to develop such products for prevention of HCV infection. The only preventative strategies relate to the ability to stop transmission of the virus by screening blood supplies and educating the public regarding high-risk groups and behaviors.

Two treatments are available in the United States for those infected with HCV: monotherapy treatment with alpha interferon or combination therapy with alpha interferon and ribavirin. Combination therapy appears to be the most efficacious treatment and therefore is the treatment of choice in the United States.

Alpha interferon monotherapy can be effective in treating chronic HCV, but it is not effective against all HCV infections and there can be unwanted side effects associated with this treatment option. The other treatment option is a combination therapy with alpha interferon and ribavirin. Again, there are undesirable side effects associated with this combination therapy.

Despite years of intensive research aimed at developing treatments and prophylactic measures against HCV, there is a need for new improved treatments of HCV.

A new class of compounds for treating HCV targets the viral protease. Telaprevir, recently approved by the FDA, is the front runner in this category, with first in class blockbuster potential. Other advanced clinical programs include nucleoside and non-nucleoside polymerase inhibitors which target the viral RNA polymerase.

The mechanisms that viruses use to propagate themselves involves co-opting certain aspect of their host cell to enter, be transported to the correct location in the cell (e.g., nucleus) for replication or establishment of latency, depart an infected cell and are only beginning to be understood on a general level. One long standing difficult goal in antiviral research has been the search of host cell factors that can be target for treating and preventing viral infection.

A group of enzymes known as lysine methyl transferases and lysine demethylases are involved in histone lysine modifications. One particular human lysine demethylase enzyme called Lysine Specific Demethylase-1 (LSD1) was recently discovered (Shi et al. (2004) *Cell* 119:941) and shown to be involved in histone lysine methylation. LSD1 has a fair degree of structural similarity, and amino acid identity/homology to polyamine oxidases and monoamine oxidases, all of which (i.e., MAO-A, MAO-B and LSD1) are flavin dependent amine oxidases which catalyze the oxidation of nitrogen-hydrogen bonds and/or nitrogen-carbon bonds. Although the main target of LSD1 appears to be mono- and di-methylated histone lysines, specifically H3K4 and H3K9, there is evidence in the literature that LSD1 can demethylate methylated lysines on non-histone proteins like p53, E2F1, Dnmt1 and STAT3.

Several groups have reported LSD1 inhibitors in the literature. Sharma et al. recently reported a new series of urea and thiourea analogs based on an earlier series of polyamines which were shown to inhibit LSD1 and modulate histone methylation and gene expression in cells (J. Med. Chem. 2010 PMID: 20568780 [PubMed—as supplied by publisher]). Sharma et al. note that "To date, only a few existing compounds have been shown to inhibit LSD1." Some efforts were made to make analogs of the histone peptide that is methylated by the enzyme, other efforts have focused on more small molecule like molecules based on known MAO inhibitors. Gooden et al. reported trans-2-arylcyclopropylamine analogues that inhibit LSD1 with Ki values in the range of 188-566 micromolar (Gooden et al. ((2008) *Bioorg. Med. Chem. Let.* 18:3047-3051)). Most of these compounds were more potent against MAO-A as compared to MAO-B. Ueda et al. ((2009) J. Am. Chem Soc. 131(48):17536-17537) reported cyclopropylamine analogs selective for LSD1 over MAO-A and MAO-B that were designed based on reported X-ray crystal structures of these enzymes with a phenylcyclopropylamine-FAD adduct and a FAD-N-propargyl lysine peptide. The reported IC50 values for phenylcyclopropylamine were about 32 micromolar for LSD1 whereas as compounds 1 and 2 had values of 2.5 and 1.9 micromolar respectively.

Importantly, studies have also been conducted on amine oxidase inhibitor compounds to determine selectivity for MAO-A versus MAO-B since MAO-A inhibitors can cause dangerous side-effects (see e.g., Yoshida et al. (2004) Bioorg. Med. Chem. 12(10):2645-2652; Hruschka et al. (2008) Biorg Med Chem. (16):7148-7166; Folks et al. (1983) J. Clin. Psychopharmacol. (3)249; and Youdim et al. (1983) Mod. Probl. Pharmacopsychiatry (19):63).

Currently the treatments available for HCV and related diseases have serious drawbacks. There is a need for new drugs for these diseases that target novel points of intervention in the disease processes and avoid side-effects associated with certain targets. The invention described herein below provides an entirely new class of HCV antivirals.

BRIEF SUMMARY OF THE INVENTION

The present invention relates to the treatment or prevention of Flaviviridae infection and diseases caused by such viruses, and in particular hepatitis C. The inventors have unexpectedly found that inhibitors of LSD1 reduce HCV RNA replication. This finding is unexpected since HCV is not thought to go through a DNA replicative intermediate and the most well characterized functions of LSD1 relate to histone methylation and its effect on modulating DNA transcription. Advantageously, the use of selective LSD1 inhibitors or dual LSD1/MAOB inhibitors avoids side-effects associated with targets such as MAOA. Furthermore, the invention is also based on the unexpected finding that LSD1 inhibitors targeting a host cell protein inhibit HCV RNA replication and therefore avoid problems with targeting a viral activity like viral proteases or polymerases, which result in the generation of resistant strains. The inventors found that administration of LSD1 inhibitors chronically was well tolerated in a mammal (selective and dual LSD1/MAOB inhibitors). Thus, the inventors have unexpectedly found that LSD1 inhibition, particularly selective LSD1 inhibition or LSD1/MAOB dual inhibitions, is a new therapeutic approach to treating and preventing Flaviviridae infection and related diseases and disorders.

The present invention provides for the treatment and prevention of Flaviviridae infection and diseases caused by Flaviviridae infection. In particular, the invention provides compositions and methods that affect the ability of Flaviviridae to utilize the host's cellular machinery as part of the virus' lifecycle. The invention relates to the finding that interfering with the normal ability of viruses to utilize the host cell machinery with LSD1 inhibitors reduces HCV RNA replication.

The Flaviviridae infections and the diseases caused by Flaviviridae to be treated or prevented in accordance with the present invention include, without being limited thereto, infections and diseases caused by Hepatitis C Virus, Yellow fever virus, West Nile Virus, Dengue Virus or Japanese encephalitis virus. The diseases caused by Flaviviridae comprise, e.g., Hepatitis C infection, Yellow fever, Dengue fever, Japanese encephalitis, or West Nile encephalitis. The invention particularly relates to the treatment or prevention of an infection or disease caused by Hepatitis C Virus.

Thus, the treatment and prevention of Flaviviridae infection and diseases caused by Flaviviridae according to the invention comprises administering to an individual in need of treatment, a therapeutically effective amount of a LSD1 inhibitor. The individual in need of treatment can be a human or e.g., another mammal. In one embodiment, the Flaviviridae is Hepatitis C Virus, Yellow fever virus, West Nile Virus, Dengue Virus or Japanese encephalitis virus. In particular, the Flaviviridae may be Hepatitis C Virus, West Nile Virus or Dengue Virus. In one embodiment, the Flaviviridae is Hepatitis C Virus. In one embodiment, the disease caused by Flaviviridae is Hepatitis C infection, Yellow fever, Dengue fever, Japanese encephalitis, or West Nile encephalitis. In another embodiment, the disease caused by Flaviviridae is Hepatitis C infection.

Accordingly, the invention provides HCV treatment and prevention methods and compositions based on inhibitors of LSD1.

In one embodiment, the invention provides a method of affecting the ability of HCV to replicate RNA. According to this method, an effective amount of a pharmaceutical composition comprising a LSD1 inhibitor is administered to an individual in need of treatment. The composition is preferably a small molecule inhibitor of LSD1.

In another embodiment, the invention provides a method of treating an individual infected with HCV by administering to the individual a therapeutically effective amount of a LSD1 inhibitor. According to one aspect of this embodiment, the LSD1 inhibitor is an irreversible or a reversible amine oxidase inhibitor. In one aspect, the irreversible amine oxidase inhibitor is a phenylcyclopropylamine derivative or analog, a phenelzine derivative or analog, or a propargylamine derivative or analog.

In yet another embodiment, the present invention provides a method of treating an individual infected with HCV by administering, to a patient in need of therapeutic or prophylactic treatment, an amount of a LSD1 inhibitor effective to reduce HCV RNA replication. Such treatments can be used to suppress the symptoms of HCV i.e., suppressive therapy, or for treating episodic outbreaks i.e., episodic therapy.

The invention further provides a method of identifying compounds that have HCV antiviral activity. More particularly, the method involves identifying compounds that inhibit LSD1 and then testing the LSD1 inhibitors in an HCV antiviral assay. According to this embodiment an assay system is employed to detect compounds and/or compositions that affect the ability of the virus to propagate itself.

In one aspect, the invention is a method of treating or preventing a symptom of HCV infection in an individual infected with HCV comprising identifying a patient in need of such treatment and administering to said individual for a sufficient period of time an amount of a LSD1 inhibitor sufficient to improve the symptom or reduce the rate of decline of the symptom thereby treating or preventing said symptom of HCV infection. In a related aspect, the invention is the use of a LSD1 inhibitor in an amount sufficient to modulate LSD1 activity for treating or preventing liver disease in an individual infected with HCV. In a specific aspect, the liver disease is hepatitis or hepatocellular carcinoma. In one embodiment of this aspect, the amount of LSD1 inhibitor administered is sufficient to modulate or inhibit LSD1 activity while not substantially inhibiting MAOA activity, thereby avoiding or reducing side-effects associated with administration of MAOA inhibitors.

In one aspect, the invention relates to a pharmaceutical composition for use in treating Flaviviridae comprising an anti-Flaviviridae effective amount of a LSD1 inhibitor. In one embodiment, the Flaviviridae is Hepatitis C Virus, Yellow fever virus, West Nile Virus, Dengue Virus or Japanese encephalitis virus. In particular, the Flaviviridae may be Hepatitis C Virus, West Nile Virus or Dengue Virus. In one embodiment, the Flaviviridae is Hepatitis C Virus.

In one aspect, the invention relates to a pharmaceutical composition for use in treating HCV infection comprising an anti-HCV effective amount of a LSD1 inhibitor.

In one aspect, the invention relates to a method of combination treatment. According to this method a LSD1 inhibitor and a second anti-HCV agent are administered to an individual (e.g. a human) in need of treatment. In one aspect, the second anti-HCV agent is preferably chosen from an interferon agent, a nucleoside polymerase inhibitor, a non-nucleoside polymerase inhibitor, a protease inhibitor or a NS5A inhibitor. In one aspect, the protease inhibitor is Telaprevir, Boceprevir, TMC435350, R7227, or BI201335. In one aspect, the nucleoside polymerase inhibitor is R7128, PSI-7851, or IDX184.

In one aspect, the invention relates to a composition for combination treatment of HCV. Accordingly, the pharmaceutical composition of this aspect comprises a LSD1 inhibitor and a second anti-HCV agent along with a pharmaceutically acceptable carrier or excipient. In one aspect, the second agent is chosen from a nucleoside polymerase inhibitor, a non-nucleoside polymerase inhibitor, a protease inhibitor or a NS5A inhibitor. In one aspect, the protease inhibitor is Telaprevir, Boceprevir, TMC435350, R7227, or BI201335. In one aspect, the nucleoside polymerase inhibitor is R7128, PSI-7851, or IDX184. In one aspect, the non-nucleoside polymerase inhibitor is PF-868554 or GS-9190. In one aspect, the NS5A inhibitor is BMS-790052.

In one aspect, the invention is a method or pharmaceutical composition for treating an individual co-infected with HCV and HBV. Accordingly, the method comprises identifying an individual in need of treatment and administering to said individual a therapeutically effective amount of an LSD1 inhibitor. In a more specific aspect, the method further comprises administering to said individual one or more anti-HCV or anti-HBV agents.

In one aspect, the sufficient period of time for administering the LSD1 inhibitors is for 5 or more days to the individual, more preferably from 5 days to 4 years, even more preferably from 5 days to two years, yet even more preferably for 15 days to 2 years, and again yet even more preferably from 15 days to 1 year. In one aspect, the LSD1 inhibitor is administered daily in amount sufficient to yield a Cmax above the IC50 value for the LSD1 inhibitor. A person skilled in the art will appreciate that the Cmax should be above the IC50 value in the same species (e.g., in a human) in which the Cmax is to be measured.

The invention also relates to an LSD1 inhibitor for use in any of the above-described methods.

Accordingly, the invention relates to an LSD1 inhibitor (or a pharmaceutical composition comprising an LSD1 inhibitor and a pharmaceutically acceptable carrier) for use in the treatment or prevention of a Flaviviridae infection or a disease caused by Flaviviridae. In one embodiment, the Flaviviridae is Hepatitis C Virus, Yellow fever virus, West Nile Virus, Dengue Virus or Japanese encephalitis virus. In particular, the Flaviviridae may be Hepatitis C Virus, West Nile Virus or Dengue Virus. In one embodiment, the Flaviviridae is Hepatitis C Virus. In a preferred embodiment, the invention relates to an LSD1 inhibitor (or a pharmaceutical composition comprising an LSD1 inhibitor and a pharmaceutically acceptable carrier) for use in the treatment or prevention of HCV infection or a disease caused by HCV. In another embodiment, the invention relates to an LSD1 inhibitor (or a pharmaceutical composition comprising an LSD1 inhibitor and a pharmaceutically acceptable carrier) for use in the treatment or prevention of a symptom of HCV infection in an individual infected with HCV. In another embodiment the invention relates to an LSD1 inhibitor (or a pharmaceutical composition comprising an LSD1 inhibitor and a pharmaceutically acceptable carrier) for use in the treatment or prevention of a liver disease in an individual infected with HCV. In a preferred embodiment, the liver disease is hepatitis or hepatocellular carcinoma.

The present invention furthermore provides a LSD1 inhibitor to be administered in combination with one or more further therapeutic agents for use in the treatment or prevention of a Flaviviridae infection or a disease caused by Flaviviridae. The one or more further therapeutic agents may, for example, be antiviral agents (such as, e.g., anti-HCV agents). In particular the invention provides a LSD1 inhibitor to be administered in combination with a second anti-HCV agent, for use in the treatment or prevention of HCV infection or a disease caused by HCV. The administration of the LSD1 inhibitor and the one or more further therapeutic agents, such as a second anti-HCV agent, may, e.g., be simultaneous/concomitant or sequential/separate. In one embodiment, the second anti-HCV agent is preferably chosen from an interferon agent, a nucleoside polymerase inhibitor, a non-nucleoside polymerase inhibitor, a protease inhibitor or a NS5A inhibitor. In one embodiment, the protease inhibitor is Telaprevir, Boceprevir, TMC435350, R7227, or BI201335. In another embodiment, the nucleoside polymerase inhibitor is R7128, PSI-7851, or IDX184. In another embodiment, the non-nucleoside polymerase inhibitor is PF-868554 or GS-9190. In another embodiment, the NS5A inhibitor is BMS-790052.

In one embodiment, the LSD1 inhibitor to be used in accordance with the present invention, in particular in the treatment or prevention of Flaviviridae infection or a disease caused by Flaviviridae, including HCV infection or a disease caused by HCV, is a small molecule inhibitor of LSD1. In a preferred embodiment, the LSD1 inhibitor is a selective LSD1 inhibitor or a dual LSD1/MAO-B inhibitor. In another embodiment, the LSD1 inhibitor is a 2-cyclylcyclopropan-1-amine compound, a phenclzine compound or a propargylamine compound, and is more preferably a 2-cyclylcyclopropan-1-amine compound. Said 2-cyclylcyclopropan-1-amine compound is preferably a 2-arylcyclopropan-1-amine compound or a 2-heteroarylcyclopropan-1-amine compound, more preferably a 2-phenylcyclopropan-1-amine compound, a 2-pyridinylcyclopropan-1-amine compound or a 2-thiazolylcyclopropan-1-amine compound.

Thus, the invention also relates to the following embodiments:
1. A method of treating or preventing Flaviviridae infection or an associated disease or disorder comprising identifying an individual in need of such treatment and administering to said individual a LSD1 inhibitor.
2. The method as in 1 wherein said Flaviviridae infection is Hepatitis C Virus, West Nile Virus or Dengue Virus.
3. The method as in 1 wherein said Flaviviridae infection is Hepatitis C virus.
4. The method as in 1 wherein said LSD1 inhibitor is a reversible or irreversible amine oxidase inhibitor.
5. The method as in 1 wherein said LSD1 inhibitor inhibits Flaviviridae RNA replication.
6. The method as in 1 wherein said LSD1 inhibitor is a phenylcyclopropylamine derivative or analog, a phenelzine derivative or analog, or a propargylamine derivative or analog.
7. The method as in 1 wherein said LSD1 has a therapeutic index of 10 or great.

8. The method as in 1 wherein said LSD1 has a therapeutic index of 100 or great.
9. The method as in 1 further comprising administering to said individual a second anti-HCV agent.
10. The method as in 9 wherein said second anti-HCV agent is an interferon agent, a protease inhibitor, a nucleoside polymerase inhibitor, a non-nucleoside polymerase inhibitor, or a NS5A inhibitor.
11. A LSD1 inhibitor or a pharmaceutical composition comprising a LSD1 inhibitor for use in treating or preventing Flaviviridae infection or a related disease or disorder.
12. The LSD1 inhibitor as in 11 wherein said Flaviviridae infection is HCV infection.
13. A LSD1 inhibitor or a pharmaceutical composition comprising a LSD1 inhibitor and a second anti-HCV agent for use in treating or preventing Flaviviridae infection or a related disease or disorder.
14. The LSD1 inhibitor as in 13 wherein said Flaviviridae infection is HCV infection.
15. The LSD1 inhibitor as in 13 or 14 wherein said second anti-HCV is an interferon agent, a protease inhibitor, a nucleoside polymerase inhibitor, a non-nucleoside polymerase inhibitor, or a NS5A inhibitor.
16. The LSD1 inhibitor as in 11 to 15 wherein said LSD1 inhibitor is a reversible or irreversible amine oxidase inhibitor.
17. The LSD1 inhibitor as in 11 to 15 wherein said LSD1 inhibitor is an irreversible amine oxidase inhibitor.
18. The LSD1 inhibitor as in 11 to 15 wherein said LSD1 inhibitor is a phenylcyclopropylamine derivative or analog, a phenelzine derivative or analog, or a propargylamine derivative or analog.
19. The method as in 6 or the LSD1 inhibitor as in 18 wherein said phenelzine analog or derivative: (a) has one, two, three, four or five substituents on the phenyl group; (b) has the phenyl group substituted with (exchanged for) an aryl or heterocyclyl group wherein said aryl or heterocyclyl group has zero, one, two, three, four or five substituents; or (c) as in (a) or (b) and having a substitution on the terminal nitrogen of the hydrazine group.
20. The method as in 6 or the LSD1 inhibitor as in 18 wherein said propargylamine derivative or analog is a pargyline derivative or analog wherein: (a) said pargyline derivative or analog has one, two, three, four or five substituents on the phenyl group; (b) said pargyline derivative or analog has the phenyl group substituted with (exchanged for) an aryl or heterocyclyl group wherein said aryl or heterocyclyl group has zero, one, two, three, four or five substituents; or (c) as in (a) or (b) wherein the propargylmine moiety of pargyline has one or two substituents.
21. The method as in 6 or the LSD1 inhibitor as in 18 wherein said phenylcyclopropylamine derivative or analog: (a) has one, two, three, four or five substituents on the phenyl group; or (b) the phenyl group substituted with (exchanged for) an aryl or heterocyclyl group wherein said aryl or heterocyclyl group has zero, one, two, three, four or five substituents; or (c) as in (a) or (b) and additionally having one or two substituents on the amino group of the cyclopropylamine core.
22. A method of treating or preventing HCV and HBV co-infection comprising identifying an individual in need of such treatment and administering to said individual a LSD1 inhibitor and optionally a second anti-HCV agent or anti-HBV agent.
23. The LSD1 inhibitor as in 1-21 wherein said LSD1 inhibitor has a therapeutic index of 100 or greater.
24. The method of 6 or 21 or the LSD1 inhibitor of 18 or 21 wherein the phenylcyclopropylamine derivative or analog has the 1S,2R configuration in respect to the substituents on the cyclopropyl ring.
25. The method of 6 or 21 or the LSD1 inhibitor of 18 or 21 wherein the phenylcyclopropylamine derivative or analog has the 1R,2S configuration in respect to the substituents on the cyclopropyl ring.

BRIEF DESCRIPTION OF THE DRAWINGS

FIG. 1 summarizes structure-activity relationship evolution of increased potency towards LSD1 as compared to MAOA and/or MAOB from compounds that were not selective (e.g., tranylcypromine) to compounds that are selective inhibitors of LSD1 with IC50 values in the low nanomolar range.

FIG. 2 summarizes structure-activity relationship evolution of increased potency towards LSD1 and MAOB as compared to MAOA from compounds that were not selective for LSD1 and MAOB (e.g., tranylcypromine). The dual LSD1/MAOB compounds have IC50 values for these two targets in the low nanomolar range.

FIG. 3A. shows the results of a western blot stained for H3K4 methylation with SH-SY5Y cells grown in the presence of Compound Dual-1 (at 100 µM) or parnate ("PNT") (at 250 µM) for 1, 2, and 3 days, showing that this compound, Dual-1, increases H3K4 methylation in cells in a time dependent manner. FIG. 3B is a graph showing quantification of the results shown in FIG. 3A.

DETAILED DESCRIPTION OF THE INVENTION

Figure 1:
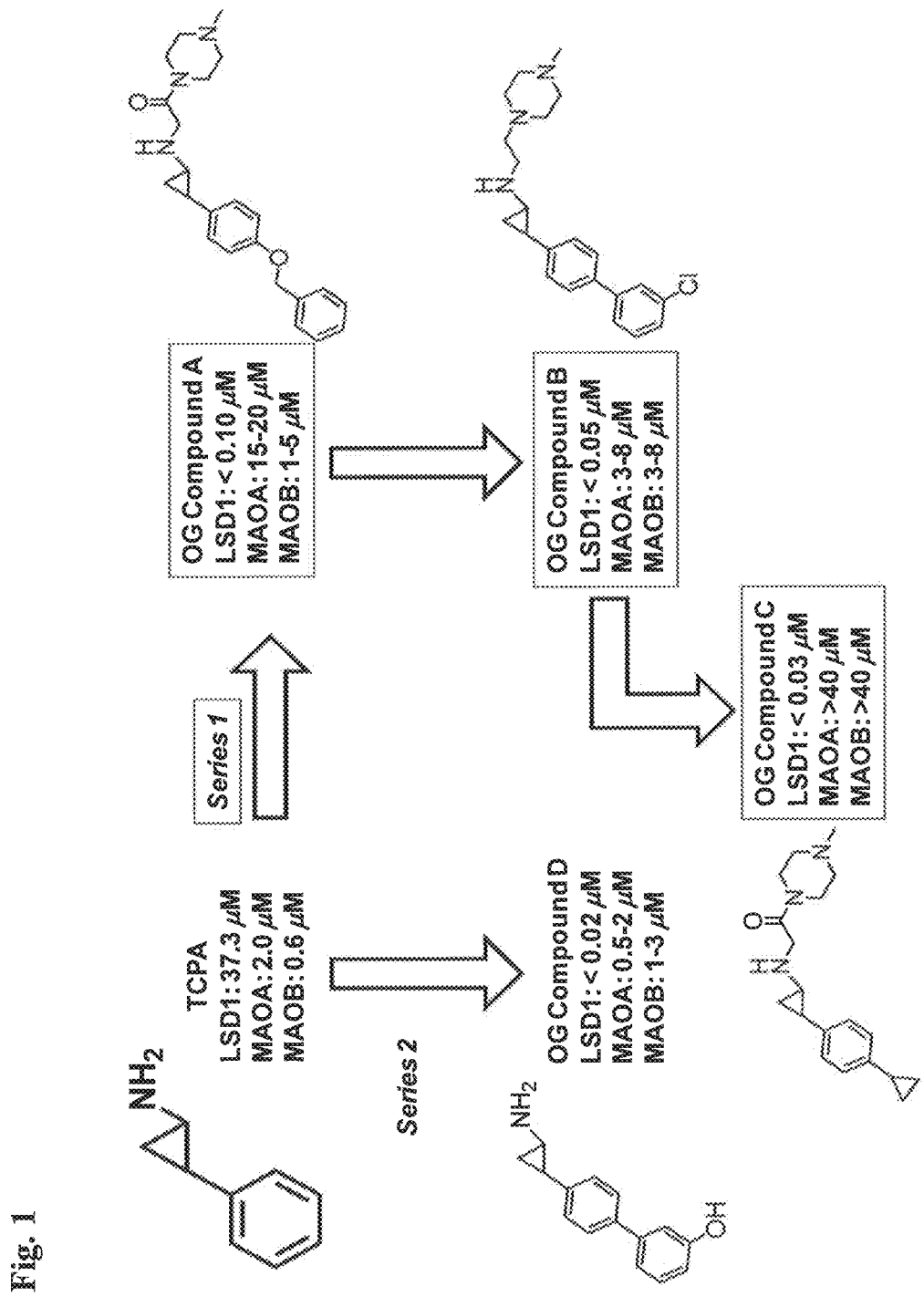
FIG. 1 Optimization of Selective LSD1 Inhibitors.

The inventors have unexpectedly found that inhibitors of LSD1 can reduce HCV RNA replication. This finding is unexpected since HCV is thought not to go through a DNA replicative intermediate and the most well characterized functions of LSD1 relate to histone methylation and its effect on modulating DNA transcription. Thus, the inventors have shown that LSD1 inhibitors inhibit the ability of RNA viruses such as HCV, a member of the Flaviviridae family of viruses, to replicate their RNA. This finding is significant since RNA viruses are known to mutate rapidly and develop resistance to therapeutics targeted to viral proteins. Thus, the methods and compositions of the invention can be useful for treating viruses and viral infections resistant to current treatments or treatment that are in developments and eventually clinically approved. Additionally, the methods and compositions of the invention can be useful for treating viruses or viral infection while reducing the likelihood of the virus or viral infection to developing resistance to current treatments or treatment that are in developments and eventually clinically approved. Other advantages and more details of the invention are described in more detail below.

A medicinal chemistry effort undertaken by some of the inventors resulted in the synthesis and identification of small molecule, potent selective LSD1 inhibitors and potent dual inhibitors of LSD1 and MAOB. This effort resulted in the identification of a number of compounds having different selectivities for LSD1, MAOA, and MAOB. See FIG. 1.

Subsequent studies of some of the optimized compounds in a neural derived cell line and other cell lines indicted that both selective LSD1 inhibitors and dual inhibitors of LSD1 and MAOB can increase histone methylation levels at the cellular level, indicating that these compounds inhibit cellular lysine demethylase activity. Furthermore, these LSD1 inhibitors show dose dependent effects on gene expression levels in these cells.

The LSD1 inhibitors were able to be administered safely to mammals chronically at doses that are thought to achieve levels of the inhibitor sufficient for causing a biological effect.

Lastly, Compound X, a potent selective LSD1 inhibitor was shown to have activity in the 300-500 nanomolar range in an HCV RNA replication assay with a "therapeutic index" of greater than 100. See Example 5. Without being bound by theory, it is believed that LSD1 inhibitors, including selective LSD1 inhibitors and dual LSD1/MAO-B inhibitors, inhibit HCV RNA replication and have use for treating or preventing Flaviviridae infection or an associated disease or disorder. More specifically, it is believed that LSD1 inhibitors, as a result of this invention, have use in treating or preventing HCV or an associated disease or disorder.

Methods of Treatment or Prevention and Disease

The invention relates to methods of treatment or prevention of diseases or disorders related to Flaviviridae infection.

In one embodiment, the invention is the use of a LSD1 inhibitor for treating or preventing Flaviviridae infection. In a related aspect, the invention is a method of treating or preventing Flaviviridae infection comprising administering a LSD1 inhibitor to an individual. In another related aspect, the invention is a method of treating or preventing Flaviviridae infection comprising administering a LSD1 inhibitor to an individual in need of such treatment. In yet another related aspect, the invention is a method of treating or preventing Flaviviridae infection comprising identifying an individual in need of such treatment or prevention and administering a LSD1 inhibitor to said individual. In one embodiment, the Flaviviridae is Hepatitis C Virus, Yellow fever virus, West Nile Virus, Dengue Virus or Japanese encephalitis virus. In a specific embodiment, the Flaviviridae is HCV, Dengue virus or West Nile virus. In another specific embodiment, the Flaviviridae is HCV. In another specific embodiment, the Flaviviridae is WNV. In another specific embodiment, the Flaviviridae is Dengue virus. In another specific embodiment, the Flaviviridae is yellow fever virus. In one aspect, the LSD1 inhibitor is a small molecule inhibitor of LSD1. In one aspect, the LSD1 inhibitor is a selective inhibitor of LSD1. In one aspect, the LSD1 inhibitor is a selective inhibitor of LSD1 and MAOB (i.e. a dual LSD1/MAO-B inhibitor). In one aspect, the LSD1 inhibitor is an irreversible or a reversible amine oxidase inhibitor. In one aspect, the irreversible amine oxidase inhibitor is a phenylcyclopropylamine derivative or analog, a phenelzine derivative or analog, or a propargylamine derivative or analog. In one aspect, the LSD1 inhibitor is a 2-cyclylcyclopropan-1-amine compound, a phenelzine compound, or a propargylamine compound, more preferably a 2-cyclylcyclopropan-1-amine compound, still more preferably a 2-arylcyclopropan-1-amine compound or a 2-heteroarylcyclopropan-1-amine compound, and even more preferably a 2-phenylcyclopropan-1-amine compound, 2-pyridinylcyclopropan-1-amine compound or a 2-thiazolylcyclopropan-1-amine compound. In one aspect of this embodiment, the LSD1 inhibitor has a therapeutic index of 10 or greater. In one aspect of this embodiment, the LSD1 inhibitor has a therapeutic index of 50 or greater. In one aspect of this embodiment, the LSD1 inhibitor has a therapeutic index of 100 or greater.

In one embodiment, the invention is the use of a LSD1 inhibitor for inhibiting Flaviviridae RNA replication. In a related aspect, the invention is a method of inhibiting Flaviviridae RNA replication comprising administering a LSD1 inhibitor to an individual. In another related aspect, the invention is a method of inhibiting Flaviviridae RNA replication comprising administering a LSD1 inhibitor to an individual in need of such treatment. In yet another related aspect, the invention is a method of inhibiting Flaviviridae RNA replication comprising identifying an individual in need of such treatment or prevention and administering a LSD1 inhibitor to said individual. In one aspect, the LSD1 inhibitor is a small molecule inhibitor of LSD1. In one aspect, the LSD1 inhibitor is a selective inhibitor of LSD1. In one aspect, the LSD1 inhibitor is a selective inhibitor of LSD1 and MAOB. In one aspect, the LSD1 inhibitor is an irreversible or a reversible amine oxidase inhibitor. In one aspect, the irreversible amine oxidase inhibitor is a phenylcyclopropylamine derivative or analog, a phenelzine derivative or analog, or a propargylamine derivative or analog. In one aspect, the LSD1 inhibitor is a 2-cyclylcyclopropan-1-amine compound, a phenelzine compound, or a propargylamine compound, more preferably a 2-cyclylcyclopropan-1-amine compound, still more preferably a 2-arylcyclopropan-1-amine compound or a 2-heteroarylcyclopropan-1-amine compound, and even more preferably a 2-phenylcyclopropan-1-amine compound, 2-pyridinylcyclopropan-1-amine compound or a 2-thiazolylcyclopropan-1-amine compound. In one aspect of this embodiment, the LSD1 inhibitor has a therapeutic index of 10 or greater. In one aspect of this embodiment, the LSD1 inhibitor has a therapeutic index of 50 or greater. In one aspect of this embodiment, the LSD1 inhibitor has a therapeutic index of 100 or greater. In one embodiment, the Flaviviridae is Hepatitis C Virus, Yellow fever virus, West Nile Virus, Dengue Virus or Japanese encephalitis virus. In one aspect of this embodiment, the Flaviviridae is HCV, WNV, or Dengue Virus. In one aspect of this embodiment, the Flaviviridae is HCV. In one aspect of this embodiment, the Flaviviridae is WNV. In one aspect of this embodiment, the Flaviviridae is Dengue Virus. In one aspect of this embodiment, the Flaviviridae is Yellow fever Virus.

In one embodiment, the invention is the use of a LSD1 inhibitor for treating or preventing HCV infection. In a related aspect, the invention is a method of treating or preventing HCV infection comprising administering a LSD1 inhibitor to an individual. In another related aspect, the invention is a method of treating or preventing HCV infection comprising administering a LSD1 inhibitor to an individual in need of such treatment. In yet another related aspect, the invention is a method of treating or preventing HCV infection comprising identifying an individual in need of such treatment or prevention and administering a LSD1 inhibitor to said individual. In one aspect, the LSD1 inhibitor is a small molecule inhibitor of LSD1. In one aspect, the LSD1 inhibitor is a selective inhibitor of LSD1. In one aspect, the LSD1 inhibitor is a selective inhibitor of LSD1 and MAOB. In one aspect, the LSD1 inhibitor is an irreversible or a reversible amine oxidase inhibitor. In one aspect, the irreversible amine oxidase inhibitor is a phenylcyclopropylamine derivative or analog, a phenelzine derivative or analog, or a propargylamine derivative or analog. In one aspect, the LSD1 inhibitor is a 2-cyclylcyclopropan-1-amine compound, a phenelzine compound, or a propargylamine compound, more preferably a 2-cyclylcyclopropan-1-amine compound, still more preferably a 2-arylcyclopropan-1-amine compound or a 2-heteroarylcyclopropan-1-amine compound, and even more preferably a 2-phenylcyclopropan-1-amine compound, 2-pyridinylcyclopropan-1-amine compound or a 2-thiazolylcyclopropan-1-amine compound. In one aspect of this embodiment, the LSD1 inhibitor has a therapeutic index of 10 or greater. In one aspect of this embodiment, the LSD1 inhibitor has a therapeutic index of 50 or greater. In one aspect of this embodiment, the LSD1 inhibitor has a therapeutic index of 100 or greater.

In one embodiment, the invention is the use of a LSD1 inhibitor for inhibiting HCV RNA replication. In a related aspect, the invention is a method of inhibiting HCV RNA replication comprising administering a LSD1 inhibitor to an individual. In another related aspect, the invention is a method of inhibiting HCV RNA replication comprising administering a LSD1 inhibitor to an individual in need of such treatment. In yet another related aspect, the invention is a method of inhibiting HCV RNA replication comprising identifying an individual in need of such treatment or prevention and administering a LSD1 inhibitor to said individual. In one aspect, the LSD1 inhibitor is a small molecule inhibitor of LSD1. In one aspect, the LSD1 inhibitor is a selective inhibitor of LSD1. In one aspect, the LSD1 inhibitor is a selective inhibitor of LSD1 and MAOB. In one aspect, the LSD1 inhibitor is an irreversible or a reversible amine oxidase inhibitor. In one aspect, the irreversible amine oxidase inhibitor is a phenylcyclopropylamine derivative or analog, a phenelzine derivative or analog, or a propargylamine derivative or analog. In one aspect, the LSD1 inhibitor is a 2-cyclylcyclopropan-1-amine compound, a phenelzine compound, or a propargylamine compound, more preferably a 2-cyclylcyclopropan-1-amine compound, still more preferably a 2-arylcyclopropan-1-amine compound or a 2-heteroarylcyclopropan-1-amine compound, and even more preferably a 2-phenylcyclopropan-1-amine compound, 2-pyridinylcyclopropan-1-amine compound or a 2-thiazolylcyclopropan-1-amine compound. In one aspect of this embodiment, the LSD1 inhibitor has a therapeutic index of 10 or greater. In one aspect of this embodiment, the LSD1 inhibitor has a therapeutic index of 50 or greater. In one aspect of this embodiment, the LSD1 inhibitor has a therapeutic index of 100 or greater.

The patient, subject, or individual, such as the individual in need of treatment or prevention, may be e.g., a eukaryote, an animal, a vertebrate animal, a mammal, a rodent (e.g., a guinea pig, a hamster, a rat, a mouse), a murine (e.g., mouse), a canine (e.g., a dog), a feline (e.g., a cat), an equine (e.g., a horse), a primate, a simian (e.g., a monkey or ape), a monkey (e.g., a marmoset, a baboon), an ape (e.g., gorilla, chimpanzee, orangutang, gibbon), or a human. The meaning of the terms "eukaryote", "animal", "mammal", etc., is well known in the art and can, for example, be deduced from Wehner und Gehring (1995; Thieme Verlag). In the context of this invention, it is particularly envisaged that animals are to be treated which are economically, agronomically or scientifically important. Scientifically important organisms include, but are not limited to, mice, rats, rabbits, fruit flies like *Drosophila melogonaster* and nematodes like *Caenorhabditis elegans*. Non-limiting examples of agronomically important animals are sheep, cattle and pig, while, for example, cats and dogs may be considered as economically important animals. Preferably, the subject/patient/individual is a mammal; more preferably, the subject/patient/individual is a human.

As used herein, in the context of diseases and disorders, the term "treating" refers to a slowing of or a reversal of the progress of the disease. Treating a disease or disorder includes treating a symptom and/or reducing the symptoms of the disease.

As used herein, in the context of diseases and disorders, the term "preventing" refers to a slowing of the disease or of the onset of the disease or the symptoms thereof. Preventing a disease or disorder can include stopping the onset of the disease or symptoms thereof.

As used herein, "second anti-HCV" refers to an anti-HCV different from the LSD1 inhibitor of the invention and which preferably does not act via LSD1 inhibition.

As used herein, "therapeutic index" refers to the ratio between the concentration of a drug that causes a lethal or toxic effect and the concentration that causes a therapeutic effect, and can be expressed as Therapeutic Index=LD50/ED50 (in animals) or TD50/ED50 (in humans). "Selectivity index", as used herein, is equivalent to "therapeutic index".

As used herein, "LSD1 inhibitor" refers to a molecule that directly or indirectly lowers or downregulates a biological activity of Lysine Dependent Demethylase 1 (LSD1). A LSD1 inhibitor may be any member of a class of compounds (e.g. a small molecule or an antibody) that binds LSD1 and inhibits a biological activity (e.g. demethylase activity) of a LSD1 protein or a protein complex in which LSD1 exerts its function (e.g. LSD1 being complexed to co-REST and/or other protein members of the nucleosome). A LSD1 inhibitor may also be any member of a class of compounds that decreases the expression of a nucleic acid encoding a LSD1 protein (e.g. an inhibitory nucleic acid, RNAi, such as a small hairpin RNA).

As used herein "a small molecule inhibitor of LSD1" refers to an LSD1 inhibitor having a molecular weight of less than 1000 daltons, preferably less than 700 daltons.

As used herein, the term "selective LSD1 inhibitor", "LSD1 selective inhibitor" or "selective inhibitor of LSD1" refers to an LSD1 inhibitor which preferably has an IC50 value for LSD1 that is at least two-fold lower than its IC50 values for MAO-A and MAO-B. More preferably, a selective LSD1 inhibitor has an IC50 value for LSD1 which is at least five-fold lower than its IC50 values for MAO-A and MAO-B. Even more preferably, a selective LSD1 inhibitor has an IC50 value for LSD1 which is at least ten-fold lower than its IC50 values for MAO-A and MAO-B. Even more preferably, a selective LSD1 inhibitor has an IC50 value for LSD1 which is at least 20-fold lower than its IC50 values for MAO-A and MAO-B. Even more preferably, a selective LSD1 inhibitor has an IC50 value for LSD1 which is at least 50-fold lower than its IC50 values for MAO-A and MAO-B. Even more preferably, a selective LSD1 inhibitor has an IC50 value for LSD1 which is at least 100-fold lower than its IC50 values for MAO-A and MAO-B. The ability of a compound to inhibit LSD1 and its IC50 values for LSD1, MAO-A and MAO-B are preferably to be determined in accordance with the experimental protocol described in Example 1.

As used herein, the term "selective inhibitor of LSD1 and MAOB", "dual LSD1/MAO-B inhibitor", "LSD1/MAO-B inhibitor", "dual LSD1/MAOB selective inhibitor", "dual inhibitor selective for LSD1 and MAO-B" or "dual inhibitor of LSD1 and MAO-B" refers to an LSD1 inhibitor which preferably has IC50 values for LSD1 and MAO-B which are at least two-fold lower than its IC50 value for MAO-A. More preferably, a dual LSD1/MAO-B selective inhibitor has IC50 values for LSD1 and MAO-B which are at least five-fold lower than its IC50 value for MAO-A. Even more preferably, a dual LSD1/MAO-B selective inhibitor has IC50 values for LSD1 and MAO-B which are at least ten-fold lower than its IC50 value for MAO-A. Even more preferably, a dual LSD1/MAO-B selective inhibitor has IC50 values for LSD1 and MAO-B which are at least 20-fold lower than its IC50 value for MAO-A. The ability of a compound to inhibit LSD1 and MAO-B and its IC50 values for LSD1, MAO-A and MAO-B are preferably to be determined in accordance with the experimental protocol described in Example 1.

In another aspect, the invention is a method of treating HCV comprising identifying an individual in need of such treatment and administering to said individual for a sufficient period of time an amount of a LSD1 inhibitor, preferably a selective LSD1 inhibitor, sufficient to treat HCV. In a related aspect, the invention is the use of a LSD1 inhibitor, preferably a selective LSD1 inhibitor, or a pharmaceutical composition comprising said LSD1 inhibitor (or said selective LSD1 inhibitor) in an amount sufficient to inhibit LSD1 activity for treating HCV. In a specific aspect, said treatment reduces HCV RNA replication. In one embodiment of this aspect, the amount of LSD1 inhibitor, preferably a selective LSD1 inhibitor, administered or that is in the pharmaceutical composition is sufficient to modulate or inhibit LSD1 activity while not substantially inhibiting MAOA activity, thereby avoiding or reducing side-effects associated with administration of MAOA inhibitors. In a specific aspect of this embodiment, preferably the amount of LSD1 inhibitor administered per day to a human is from about 0.5 mg to about 500 mg per day. More preferably the amount of LSD1 inhibitor administered per day to a human is from about 0.5 mg to about 200 mg per day or is a pharmaceutical composition formulated in such a way as to deliver this amount of free base equivalent (or free acid equivalent depending on the parent molecule). Preferably, the LSD1 inhibitor is administered or formulated to be administered for 5 or more days to the individual, more preferably from 5 days to 4 years, even more preferably from 5 days to two years, yet even more preferably for 15 days to 2 years, and again yet even more preferably from 15 days to 1 year. It is noted that in this context administration for e.g., 5 or more days, means an amount sufficient over a time sufficient to cause pharmacologic inhibition of LSD1 over this period of time and this does not necessarily mean administration of compound every day or only once per day. Depending on the PK/ADME properties of the inhibitors, a suitable amount and dosing regimen can be determined by a skilled practitioner in view of this disclosure.

In one aspect, the invention is a method of treating or preventing HCV comprising identifying an individual in need of such treatment and administering to said individual for a sufficient period of time an amount of a dual LSD1/MAOB inhibitor sufficient to treat or prevent HCV. In a related aspect, the invention is the use of a dual LSD1/MAOB inhibitor or a pharmaceutical composition comprising said dual LSD1/MAOB inhibitor in an amount sufficient to modulate LSD1 activity for treating or preventing HCV. In a specific aspect, treating or preventing HCV comprises inhibiting HCV RNA replication. In one embodiment of this aspect, the amount of selective LSD1 inhibitor administered or that is in the pharmaceutical composition is sufficient to inhibit LSD1 and MAOB activity while not substantially inhibiting MAOA activity, thereby avoiding or reducing side-effects associated with administration of MAOA inhibitors. In a specific aspect of this embodiment, preferably the amount of LSD1/MAOB inhibitor administered per day to a human is from about 0.5 mg to about 500 mg per day. More preferably, the amount of LSD1/MAOB inhibitor administered per day to a human is from about 0.5 mg to about 200 mg per day or is a pharmaceutical composition formulated in such a way as to deliver this amount of free base equivalent (or free acid equivalent depending on the parent molecule). In one embodiment of this aspect, the amount of LSD1/MAOB inhibitor administered is sufficient to inhibit LSD1/MAOB activity while not substantially inhibiting MAOA activity, thereby avoiding or reducing side-effects associated with administration of MAOA inhibitors. Preferably, the dual LSD1/MAOB inhibitor is administered or formulated to be administered for 5 or more days to the individual, more preferably from 5 days to 4 years, even more preferably from 5 days to two years, yet even more preferably for 15 days to 2 years, and again yet even more preferably from 15 days to 1 year. It is noted that in this context administration for e.g., 5 or more days, means an amount sufficient over a time sufficient to cause pharmacologic inhibition of LSD1 and MAOB over this period of time and this does not necessarily mean administration of compound every day or only once per day. Depending on the PK/ADME properties of the inhibitors, a suitable amount and dosing regimen can be determined by a skilled practitioner in view of this disclosure.

In one aspect, the invention is a method of treating or preventing HCV comprising identifying an individual in need of such treatment and administering to said individual for a sufficient period of time an amount of a LSD1 inhibitor and an interferon agent sufficient to treat or prevent HCV. In a related aspect, the invention is the use of a LSD1 inhibitor, or a pharmaceutical composition comprising said LSD1 inhibitor, and an interferon agent, or a pharmaceutical composition comprising said interferon agent, in an amount sufficient for treating or preventing HCV. In a specific aspect, treating or preventing HCV comprises inhibiting HCV RNA replication via LSD1 and inhibiting HCV via an interferon dependent mechanism. In one embodiment of this aspect, the amount of interferon administered to the individual is sufficient to treat or prevent HCV while avoiding or reducing side-effects associated with administration of higher doses of interferon. In a specific aspect of this embodiment, preferably the amount of LSD1 administered per day to a human is from about 0.5 mg to about 500 mg per day. More preferably the amount of LSD1 inhibitor administered per day to a human is from about 0.5 mg to about 200 mg per day or is a pharmaceutical composition formulated in such a way as to deliver this amount of free base equivalent (or free acid equivalent depending on the parent molecule). In one embodiment of this aspect, the amount of the interferon agent administered to the individual is sufficient to treat or prevent HCV. More preferably, the amount of the interferon agent administered to the individual is sufficient to treat or prevent HCV while avoiding or lessening the side effects associated with higher doses of an interferon agent. Depending on the PK/ADME properties of the inhibitors and interferon agent a suitable amount and dosing regimen can be determined by a skilled practitioner in view of this disclosure.

In one aspect, the invention is a method of treating or preventing HCV comprising identifying a individual in need of such treatment and administering to said individual for a sufficient period of time an amount of a LSD1 inhibitor and a protease inhibitor sufficient to treat or prevent HCV. In a related aspect, the invention relates to a LSD1 inhibitor, or a pharmaceutical composition comprising said LSD1 inhibitor, and a protease inhibitor, or a pharmaceutical composition comprising said protease inhibitor, in an amount sufficient for use in treating or preventing HCV. In a specific aspect, treating or preventing HCV comprises inhibiting HCV RNA replication via LSD1 and inhibiting HCV via a protease dependent mechanism. In one embodiment of this aspect, the amount of protease administered is sufficient to prevent or treat HCV. In one embodiment of this aspect, the amount of protease administered is sufficient to prevent or treat HCV while avoiding or reducing side-effects associated with administration of higher doses of protease inhibitor. In one aspect, the protease inhibitor is Telaprevir, Boceprevir, TMC435350, R7227, VX985, MK7009 (Vaniprevir) or BI201335. In a specific aspect of this embodiment, preferably the amount of LSD1 administered per day to a human is from about 0.5 mg to about 500 mg per day. More preferably the amount of LSD1 inhibitor administered per day to a human is from about 0.5 mg to about 200 mg per day or is a pharmaceutical composition formulated in such a way as to deliver this amount of free base equivalent (or free acid equivalent depending on the parent molecule). In one embodiment of this aspect, the amount of the protease inhibitor administered to the individual is from 100 to 3000 mg daily. More preferably, the amount of the protease inhibitor is administered to the individual is from 100 to 2500 mg daily. Even more preferably, the amount of the protease inhibitor administered to the individual is from 100 to 2000 mg daily. Depending on the PK/ADME properties of the inhibitors, a suitable amount and dosing regimen can be determined by a skilled practitioner in view of this disclosure.

In one aspect, the invention is a method of treating or preventing HCV comprising identifying a individual in need of such treatment and administering to said individual for a sufficient period of time an amount of a LSD1 inhibitor and a nucleoside polymerase inhibitor sufficient to treat or prevent HCV. In a related aspect, the invention is the use of a LSD1 inhibitor, or a pharmaceutical composition comprising said LSD1 inhibitor, and nucleoside polymerase inhibitor, or a pharmaceutical composition comprising said nucleoside polymerase inhibitor, in an amount sufficient for treating or preventing HCV. In a specific aspect, treating or preventing HCV comprises inhibiting HCV RNA replication via LSD1 and inhibiting HCV via a nucleoside polymerase dependent mechanism. In one embodiment of this aspect, the amount of nucleoside polymerase inhibitor administered is sufficient to treat or prevent HCV. In one embodiment of this aspect, the amount of nucleoside polymerase inhibitor administered is sufficient to treat or prevent HCV while avoiding or reducing side-effects associated with administration of higher doses of nucleoside polymerase inhibitor. In one aspect, the nucleoside polymerase inhibitor is BI-207127, MK0608, R7128, PSI-7851, or IDX184. In a specific aspect of this embodiment, preferably the amount of LSD1 administered per day to a human is from about 0.5 mg to about 500 mg per day. More preferably the amount of LSD1 inhibitor administered per day to a human is from about 0.5 mg to about 200 mg per day or is a pharmaceutical composition formulated in such a way as to deliver this amount of free base equivalent (or free acid equivalent depending on the parent molecule). In one embodiment of this aspect, the amount of the nucleoside polymerase inhibitor administered to the individual is from 50 to 3000 mg per day. More preferably, the amount of the nucleoside polymerase inhibitor is administered to the individual is from 50 to 2250 mg per day. Even more preferably, the amount of the nucleoside polymerase inhibitor administered to the individual is from 50 to 1500 mg per day. Depending on the PK/ADME properties of the inhibitors, a suitable amount and dosing regimen can be determined by a skilled practitioner in view of this disclosure.

In one aspect, the invention is a method of treating or preventing HCV comprising identifying an individual in need of such treatment and administering to said individual for a sufficient period of time an amount of a LSD1 inhibitor and a non-nucleoside polymerase inhibitor sufficient to treat or prevent HCV. In a related aspect, the invention is the use of a LSD1 inhibitor, or a pharmaceutical composition comprising said LSD1 inhibitor, and non-nucleoside polymerase inhibitor, or a pharmaceutical composition comprising said non-nucleoside polymerase inhibitor, in an amount sufficient for treating or preventing HCV. In a specific aspect, treating or preventing HCV comprises inhibiting HCV RNA replication via LSD1 and inhibiting HCV via a nucleoside polymerase dependent mechanism. In one embodiment of this aspect, the amount of non-nucleoside polymerase inhibitor administered is sufficient to treat or prevent HCV. In one embodiment of this aspect, the amount of non-nucleoside polymerase inhibitor administered is sufficient to treat or prevent HCV while avoiding or reducing side-effects associated with administration of higher doses of non-nucleoside polymerase inhibitor. In one aspect, the non-nucleoside polymerase inhibitor is chosen from VX222, ANA598, GS9190, VCH759, PF-868554, ABT072, ABT333, or GL59728. In a specific aspect of this embodiment, preferably the amount of LSD1 administered per day to a human is from about 0.5 mg to about 500 mg per day. More preferably the amount of LSD1 inhibitor administered per day to a human is from about 0.5 mg to about 200 mg per day or is a pharmaceutical composition formulated in such a way as to deliver this amount of free base equivalent (or free acid equivalent depending on the parent molecule). In one embodiment of this aspect, the amount of the non-nucleoside polymerase inhibitor administered to the individual is from 50 to 3000 mg per day. More preferably, the amount of the non-nucleoside polymerase inhibitor is administered to the individual is from 50 to 2250 mg per day. Even more preferably, the amount of the non-nucleoside polymerase inhibitor administered to the individual is from 50 to 1500 mg per day. Depending on the PK/ADME properties of the inhibitors, a suitable amount and dosing regimen can be determined by a skilled practitioner in view of this disclosure.

In one aspect, the invention is a method of treating or preventing HCV comprising identifying an individual in need of such treatment and administering to said individual for a sufficient period of time an amount of a LSD1 inhibitor and a NS5A inhibitor sufficient to treat or prevent HCV. In a related aspect, the invention is the use of a LSD1 inhibitor, or a pharmaceutical composition comprising said LSD1 inhibitor, and NS5A inhibitor, or a pharmaceutical composition comprising said NS5A inhibitor, in an amount sufficient for treating or preventing HCV. In a specific aspect, treating or preventing HCV comprises inhibiting HCV RNA replication via LSD1 and inhibiting HCV via a NS5A dependent mechanism. In one embodiment of this aspect, the amount of NS5A inhibitor administered is sufficient to treat or prevent HCV. In one embodiment of this aspect, the amount of NS5A inhibitor administered is sufficient to treat or prevent HCV while avoiding or reducing side-effects associated with administration of higher doses of NS5A inhibitor. In one aspect, the NS5A inhibitor is BMS-790052. In a specific aspect of this embodiment, preferably the amount of LSD1 administered per day to a human is from about 0.5 mg to about 500 mg per day. More preferably the amount of LSD1 inhibitor administered per day to a human is from about 0.5 mg to about 200 mg per day or is a pharmaceutical composition formulated in such a way as to deliver this amount of free base equivalent (or free acid equivalent depending on the parent molecule). In one embodiment of this aspect, the amount of the NS5A inhibitor administered to the individual is from 50 to 3000 mg per day. More preferably, the amount of the NS5A inhibitor is administered to the individual is from 50 to 2250 mg per day. Even more preferably, the amount of the NS5A inhibitor administered to the individual is from 50 to 1500 mg per day. Depending on the PK/ADME properties of the inhibitors, a suitable amount and dosing regimen can be determined by a skilled practitioner in view of this disclosure.

In one aspect, the invention relates to treating or preventing a disease or disorder associated with co-infection of HBV and HCV comprising identifying a patient co-infected or suspected of being co-infected with HBV and HCV and administering to said patient a therapeutically effective amount of an LSD1 inhibitor and one or more anti-HCV or anti-HBV agents. One preferred anti-HCV or anti-HBV agent is an interferon agent. Other anti-HBV agents include Lamivudine, Adefovir Dipivoxil, Entecavir, Telbivudine, or Tenofovir. In one aspect, the second anti-HBV agent is Lamivudine, Adefovir Dipivoxil, Entecavir, Telbivudine, or Tenofovir. Other anti-HCV agents include protease inhibitors, nucleoside polymerase inhibitors, non-nucleoside polymerase inhibitors, and NS5A inhibitors as described herein. While not wishing to be bound by theory, it is believed that treatment of HCV and HBV co-infection with an LSD1 inhibitor according to the invention yields unexpected benefits.

The invention also relates to an LSD1 inhibitor for use in any of the above-described methods.

Accordingly, the invention relates to an LSD1 inhibitor (or a pharmaceutical composition comprising an LSD1 inhibitor and a pharmaceutically acceptable carrier) for use in treating or preventing a Flaviviridae infection. In one embodiment, the Flaviviridae is Hepatitis C Virus, Yellow fever virus, West Nile Virus, Dengue Virus or Japanese encephalitis virus. In a specific embodiment, the Flaviviridae is HCV, Dengue virus or West Nile virus. In another specific embodiment, the Flaviviridae is HCV. In another specific embodiment, the Flaviviridae is WNV. In another specific embodiment, the Flaviviridae is Dengue virus. In another specific embodiment, the Flaviviridae is yellow fever virus. In one aspect, the LSD1 inhibitor is a small molecule inhibitor of LSD1. In one aspect, the LSD1 inhibitor is a selective inhibitor of LSD1. In one aspect, the LSD1 inhibitor is a selective inhibitor of LSD1 and MAOB (i.e. a dual LSD1/MAO-B inhibitor). In one aspect, the LSD1 inhibitor is a 2-cyclylcyclopropan-1-amine compound, a phenelzine compound, or a propargylamine compound, more preferably a 2-cyclylcyclopropan-1-amine compound, still more preferably a 2-arylcyclopropan-1-amine compound or a 2-heteroarylcyclopropan-1-amine compound, and even more preferably a 2-phenylcyclopropan-1-amine compound, 2-pyridinylcyclopropan-1-amine compound or a 2-thiazolylcyclopropan-1-amine compound. In one aspect of this embodiment, the LSD1 inhibitor has a therapeutic index of 10 or greater. In one aspect of this embodiment, the LSD1 inhibitor has a therapeutic index of 50 or greater. In one aspect of this embodiment, the LSD1 inhibitor has a therapeutic index of 100 or greater.

The invention also relates to an LSD1 inhibitor (or a pharmaceutical composition comprising an LSD1 inhibitor and a pharmaceutically acceptable carrier) for use in inhibiting Flaviviridae RNA replication. In one embodiment, the Flaviviridae is Hepatitis C Virus, Yellow fever virus, West Nile Virus, Dengue Virus or Japanese encephalitis virus. In a specific embodiment, the Flaviviridae is HCV, Dengue virus or West Nile virus. In another specific embodiment, the Flaviviridae is HCV. In another specific embodiment, the Flaviviridae is WNV. In another specific embodiment, the Flaviviridae is Dengue virus. In another specific embodiment, the Flaviviridae is yellow fever virus. In one aspect, the LSD1 inhibitor is a small molecule inhibitor of LSD1. In one aspect, the LSD1 inhibitor is a selective inhibitor of LSD1. In one aspect, the LSD1 inhibitor is a selective inhibitor of LSD1 and MAOB (i.e. a dual LSD1/MAO-B inhibitor). In one aspect, the LSD1 inhibitor is a 2-cyclylcyclopropan-1-amine compound, a phenelzine compound, or a propargylamine compound, more preferably a 2-cyclylcyclopropan-1-amine compound, still more preferably a 2-arylcyclopropan-1-amine compound or a 2-heteroarylcyclopropan-1-amine compound, and even more preferably a 2-phenylcyclopropan-1-amine compound, 2-pyridinylcyclopropan-1-amine compound or a 2-thiazolylcyclopropan-1-amine compound, or a propargylamine derivative or analog. In one aspect of this embodiment, the LSD1 inhibitor has a therapeutic index of 10 or greater. In one aspect of this embodiment, the LSD1 inhibitor has a therapeutic index of 50 or greater. In one aspect of this embodiment, the LSD1 inhibitor has a therapeutic index of 100 or greater.

Likewise, the invention encompasses an LSD1 inhibitor (or a pharmaceutical composition comprising an LSD1 inhibitor and a pharmaceutically acceptable carrier) for use in treating or preventing HCV infection. In one aspect, the LSD1 inhibitor is a small molecule inhibitor of LSD1. In one aspect, the LSD1 inhibitor is a selective inhibitor of LSD1. In one aspect, the LSD1 inhibitor is a selective inhibitor of LSD1 and MAOB (i.e. a dual LSD1/MAO-B inhibitor). In one aspect, the LSD1 inhibitor is a 2-cyclylcyclopropan-1-amine compound, a phenelzine compound, or a propargylamine compound, more preferably a 2-cyclylcyclopropan-1-amine compound, still more preferably a 2-arylcyclopropan-1-amine compound or a 2-heteroarylcyclopropan-1-amine compound, and even more preferably a 2-phenylcyclopropan-1-amine compound, 2-pyridinylcyclopropan-1-amine compound or a 2-thiazolylcyclopropan-1-amine compound. In one aspect of this embodiment, the LSD1 inhibitor has a therapeutic index of 10 or greater. In one aspect of this embodiment, the LSD11 inhibitor has a therapeutic index of 50 or greater. In one aspect of this embodiment, the LSD1 inhibitor has a therapeutic index of 100 or greater.

The invention also relates to an LSD1 inhibitor (or a pharmaceutical composition comprising an LSD1 inhibitor and a pharmaceutically acceptable carrier) for use in inhibiting HCV RNA replication. In one aspect, the LSD1 inhibitor is a small molecule inhibitor of LSD1. In one aspect, the LSD1 inhibitor is a selective inhibitor of LSD1. In one aspect, the LSD1 inhibitor is a selective inhibitor of LSD1 and MAOB (i.e. a dual LSD1/MAO-B inhibitor). In one aspect, the LSD1 inhibitor is a 2-cyclylcyclopropan-1-amine compound, a phenelzine compound, or a propargylamine compound, more preferably a 2-cyclylcyclopropan-1-amine compound, still more preferably a 2-arylcyclopropan-1-amine compound or a 2-heteroarylcyclopropan-1-amine compound, and even more preferably a 2-phenylcyclopropan-1-amine compound, 2-pyridinylcyclopropan-1-amine compound or a 2-thiazolylcyclopropan-1-amine compound. In one aspect of this embodiment, the LSD1 inhibitor has a therapeutic index of 10 or greater. In one aspect of this embodiment, the LSD1 inhibitor has a therapeutic index of 50 or greater. In one aspect of this embodiment, the LSD1 inhibitor has a therapeutic index of 100 or greater.

Moreover, the invention encompasses an LSD1 inhibitor (or a pharmaceutical composition comprising an LSD1 inhibitor and a pharmaceutically acceptable carrier) for use in the treatment or prevention of liver disease in an individual infected with HCV. In a preferred embodiment, the liver disease is hepatitis or hepatocellular carcinoma. In one aspect, the LSD1 inhibitor is a small molecule inhibitor of LSD1. In one aspect, the LSD1 inhibitor is a selective inhibitor of LSD1. In one aspect, the LSD1 inhibitor is a selective inhibitor of LSD1 and MAOB (i.e. a dual LSD1/MAO-B inhibitor). In one aspect, the LSD1 inhibitor is a 2-cyclylcyclopropan-1-amine compound, a phenelzine compound, or a propargylamine compound, more preferably a 2-cyclylcyclopropan-1-amine compound, still more preferably a 2-arylcyclopropan-1-amine compound or a 2-heteroarylcyclopropan-1-amine compound, and even more preferably a 2-phenylcyclopropan-1-amine compound, 2-pyridinylcyclopropan-1-amine compound or a 2-thiazolylcyclopropan-1-amine compound. In one aspect of this embodiment, the LSD1 inhibitor has a therapeutic index of 10 or greater. In one aspect of this embodiment, the LSD1 inhibitor has a therapeutic index of 50 or greater. In one aspect of this embodiment, the LSD1 inhibitor has a therapeutic index of 100 or greater.

The invention also relates to a LSD1 inhibitor (or a pharmaceutical composition comprising an LSD1 inhibitor and a pharmaceutically acceptable carrier) and one or more further therapeutic agents for use in the treatment or prevention of a Flaviviridae infection or a disease caused by Flaviviridae. In one aspect, the invention provides a LSD1 inhibitor (or a pharmaceutical composition comprising an LSD1 inhibitor and a pharmaceutically acceptable carrier) and a second anti-HCV agent for use in the treatment or prevention of HCV infection or a disease caused by HCV. In one embodiment, the second anti-HCV agent is chosen from an interferon agent, a nucleoside polymerase inhibitor, a non-nucleoside polymerase inhibitor, a protease inhibitor or a NS5A inhibitor. In one embodiment, the second anti-HCV agent is an interferon agent. In one embodiment, the second anti-HCV agent is a nucleoside polymerase inhibitor. In a specific embodiment the nucleoside polymerase inhibitor is BI-207127, MK0608, R7128, PSI-7851, or IDX184 In one embodiment, the second anti-HCV agent is a non-nucleoside polymerase inhibitor. In a specific embodiment the non-nucleoside polymerase inhibitor is chosen from VX222, ANA598, GS9190, VCH759, PF-868554, ABT072, ABT333, or GL59728. In one embodiment, the second anti-HCV agent is a protease inhibitor. In a specific embodiment, the protease inhibitor is Telaprevir, Boceprevir, TMC435350, R7227, VX985, MK7009 (Vaniprevir) or BI1201335. In one embodiment, the second anti-HCV agent is a NS5A inhibitor. In a specific embodiment, the NS5A inhibitor is BMS-790052. In one aspect, the LSD1 inhibitor is a small molecule inhibitor of LSD1. In one aspect, the LSD1 inhibitor is a selective inhibitor of LSD1. In one aspect, the LSD1 inhibitor is a selective inhibitor of LSD1 and MAOB (i.e. a dual LSD1/MAO-B inhibitor). In one aspect, the LSD1 inhibitor is a 2-cyclylcyclopropan-1-amine compound, a phenelzine compound, or a propargylamine compound, more preferably a 2-cyclylcyclopropan-1-amine compound, still more preferably a 2-arylcyclopropan-1-amine compound or a 2-heteroarylcyclopropan-1-amine compound, and even more preferably a 2-phenylcyclopropan-1-amine compound, 2-pyridinylcyclopropan-1-amine compound or a 2-thiazolylcyclopropan-1-amine compound. In one aspect of this embodiment, the LSD1 inhibitor has a therapeutic index of 10 or greater. In one aspect of this embodiment, the LSD1 inhibitor has a therapeutic index of 50 or greater. In one aspect of this embodiment, the LSD1 inhibitor has a therapeutic index of 100 or greater.

In one embodiment, the protease inhibitor is Telaprevir, Boceprevir, TMC435350, R7227, or BI201335. In another embodiment, the nucleoside polymerase inhibitor is R7128, PSI-7851, or IDX184. In another embodiment, the non-nucleoside polymerase inhibitor is PF-868554 or GS-9190. In another embodiment, the NS5A inhibitor is BMS-790052.

Compounds, Formulation, and Routes of Administration

The LSD1 inhibitors, in particular selective LSD1 inhibitors and dual LSD1/MAOB inhibitors for use in the invention can be synthesized by a number of techniques including the ones that are described below.

Examples of selective LSD1 and LSD1/MAOB dual inhibitors are given in e.g., WO2010/043721 (PCT/EP2009/063685), WO2010/084160 (PCT/EP2010/050697), WO 2011/035941 (PCT/EP2010/055131); WO2011/042217 (PCT/EP2010/055103); WO2011/131697 (PCT/EP2011/056279), PCT/EP2011/062947, PCT/EP2011/067608, PCT/EP2011/062949 and EP application numbers EP10171345 all of which are explicitly incorporated herein by reference in their entireties to the extent they are not inconsistent with the instant disclosure.

In one specific aspect, a phenylcyclopropylamine derivative or analog for use in the invention is phenylcyclopropylamine (PCPA) with one or two substitutions on the amine group; phenylcyclopropylamine with zero, one or two substitutions on the amine group and one, two, three, four, or five substitution on the phenyl group; phenylcyclopropylamine with one, two, three, four, or five substitution on the phenyl group; phenylcyclopropylamine with zero, one or two substitutions on the amine group wherein the phenyl group of PCPA is substituted with (exchanged for) another ring system chosen from aryl or heterocyclyl or heteroaryl to give an aryl- or heterocyclyl- or heteroaryl-cyclopropylamine having zero, one or two substituents on the amine group; phenylcyclopropylamine wherein the phenyl group of PCPA is substituted with (exchanged for) another ring system chosen from aryl or heterocyclyl to give an aryl- or heterocycyl-cyclopropylamine wherein said aryl- or heterocyclyl-cyclopropylamine on said aryl or heterocyclyl moiety has zero, one or two substitutions on the amine group and one, two, three, four, or five substitution on the phenyl group; phenylcyclopropylamine with one, two, three, four, or five substitution on the phenyl group; or any of the above described phenylcyclopropylamine analogs or derivatives wherein the cyclopropyl has one, two, three or four additional substituents. Preferably, the heterocyclyl group described above in this paragraph in a heteroaryl.

Other examples of LSD1 inhibitors are e.g., phenelzine or pargyline (propargylamine) or a derivative or analog thereof. Derivatives and analogs of phenelzine and pargyline (propargylamine) include, but are not limited to, compounds where the phenyl group of the parent compound is replaced with a heteroaryl or optionally substituted cyclic group or the phenyl group of the parent compound is optionally substituted with a cyclic group. In one aspect, the phenelzine or pargyline derivative or analog thereof has selective LSD1 or dual LSD1/MAOB inhibitory activity as described herein. In one aspect, the phenelzine derivative or analog has one, two, three, four or five substituents on the phenyl group. In one aspect, the phenelzine derivative or analog has the phenyl group substituted with (exchanged for) an aryl or heterocyclyl group wherein said aryl or heterocyclyl group has zero, one, two, three, four or five substituents. In one aspect, the pargyline derivative or analog has one, two, three, four or five substituents on the phenyl group. In one aspect, the pargyline derivative or analog has the phenyl group substituted with (exchanged for) an aryl or heterocyclyl group wherein said aryl or heterocyclyl group has zero, one, two, three, four or five substituents. Methods of preparing such compounds are known to the skilled artisan.

The LSD1 inhibitor or selective LSD1 inhibitor or dual LSD1/MAO-B inhibitor to be used in accordance with the present invention is preferably a 2-cyclylcyclopropan-1-amine compound, a phenelzine compound or a pargylamine compound, and is more preferably a 2-cyclylcyclopropan-1-amine compound. Said 2-cyclylcyclopropan-1-amine compound is preferably a 2-arylcyclopropan-1-amine compound or a 2-heteroarylcyclopropan-1-amine compound, more preferably a 2-phenylcyclopropan-1-amine compound, a 2-pyridinylcyclopropan-1-amine compound or a 2-thiazolylcyclopropan-1-amine compound.

It is particularly preferred that the LSD1 inhibitor or selective LSD1 inhibitor or dual LSD1/MAO-B inhibitor is a 2-cyclylcyclopropan-1-amine compound which is a compound of the following formula (I) or an enantiomer, a diastereomer, or a racemic mixture thereof, or a pharmaceutically acceptable salt or solvate thereof:

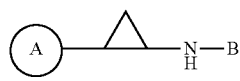

(I)

A is cyclyl optionally having 1, 2, 3 or 4 substituents A'. Preferably, said cyclyl is aryl or heteroaryl. Said aryl is preferably phenyl. Said heteroaryl is preferably selected from pyridinyl, pyrimidinyl, thiophenyl, benzothiophenyl, pyrrolyl, indolyl, furanyl or thiazolyl, more preferably said heteroaryl is selected from pyridinyl, pyrimidinyl or thiazolyl, still more preferably said heteroaryl is pyridinyl (in particular, pyridin-2-yl or pyridin-3-yl) or thiazolyl (in particular thiazol-5-yl) and even more preferably said heteroaryl is pyridin-3-yl or thiazol-5-yl.

It is preferred that said cyclyl (or said aryl or said heteroaryl, or any of the above-mentioned specific aryl or heteroaryl groups) is unsubstituted or has 1 or 2 substituents A', and it is more preferred that said cyclyl (or said aryl or said heteroaryl, or any of the above-mentioned specific aryl or heteroaryl groups) is unsubstituted or has 1 substituent A'.

Said substituent(s) A' is/are each independently selected from -$L^1$-cyclyl (e.g., -$L^1$-aryl, -$L^1$-cycloalkyl or -$L^1$-heterocyclyl), alkyl, alkenyl, alkynyl, alkoxy, amino, amido (e.g., —CO—$NH_2$), —$CH_2$—CO—$NH_2$, alkylamino, hydroxyl, nitro, halo, haloalkyl, haloalkoxy, cyano, sulfonyl, sulfinyl, sulfonamide, acyl, carboxyl, carbamate or urea, wherein the cyclyl moiety comprised in said -$L^1$-cyclyl is optionally further substituted with one or more (e.g., 1, 2 or 3) groups independently selected from halo, haloalkyl, haloalkoxy, aryl, arylalkoxy, aryloxy, arylalkyl, alkyl, alkenyl, alkynyl, alkoxy, amino, amido (e.g., —CO—$NH_2$), alkylamino, hydroxyl, nitro, —$CH_2$—CO—$NH_2$, heteroaryl, heteroarylalkoxy, heteroaryloxy, heteroarylalkyl, cyano, sulfonyl, sulfinyl, sulfonamide, acyl, carboxyl, carbamate or urea, preferably selected from halo, haloalkyl, N-sulfonamido or cyano. It is preferred that the cyclyl moiety comprised in said -$L^1$-cyclyl is unsubstituted or is substituted with one of the above groups (including, e.g., one of the preferred groups halo, haloalkyl, N-sulfonamido or cyano). In one preferred embodiment, the cyclyl moiety comprised in said -$L^1$-cyclyl is substituted with one of the above groups (including, e.g., one of the preferred groups halo, haloalkyl, N-sulfonamido or cyano). In another preferred embodiment the cyclyl moiety is unsubstituted. Said -$L^1$-cyclyl is preferably -$L^1$-aryl, -$L^1$-cycloalkyl or -$L^1$-heterocyclyl (e.g., -$L^1$-heteroaryl or -$L^1$-heterocycloalkyl), more preferably -$L^1$-aryl or -$L^1$-heteroaryl, even more preferably -$L^1$-aryl, even more preferably -$L^1$-phenyl.

Each $L^1$ is independently selected from a covalent bond, —$(CH_2)_{1-6}$—, —$(CH_2)_{0-3}$—O—$(CH_2)_{0-3}$—, —$(CH_2)_{0-3}$—NH—$(CH_2)_{0-3}$— or —$(CH_2)_{0-3}$—S—$(CH_2)_{0-3}$—, preferably from a covalent bond, —$(CH_2)_{1-3}$—, —O—$(CH_2)_{0-3}$— or —NH—$(CH_2)_{0-3}$—, more preferably from a covalent bond, —$CH_2$—, —O—, —O—$CH_2$—, —O—$(CH_2)_2$—, —NH— or —NH—$CH_2$—, even more preferably from a covalent bond, —$CH_2$— or —O—$CH_2$—. It is furthermore preferred that the aforementioned groups $L^1$ (connecting the moiety A to the cyclyl moiety comprised in -$L^1$-cyclyl) are in the specific orientation indicated above (accordingly, the group "—O—$CH_2$-" as an example for $L^1$ is preferably in the orientation ( . . . )-A-O—$CH_2$-cyclyl).

Preferably, said substituent(s) A' is/are each independently selected from -$L^1$-aryl, -$L^1$-cycloalkyl, -$L^1$-heteroaryl or -$L^1$-heterocycloalkyl, wherein said aryl, said cycloalkyl, said heteroaryl or said heterocycloalkyl is optionally substituted with halo (e.g., —F or —Cl), haloalkyl (e.g., —$CF_3$), N-sulfonamido (e.g. —$NHSO_2$-aryl, wherein the aryl group can be optionally substituted) or cyano. More preferably, said substituent(s) A' is/are each independently -$L^1$-aryl (e.g., -$L^1$-phenyl), wherein the aryl moiety in said -$L^1$-aryl (or the phenyl moiety in said -$L^1$-phenyl) is optionally substituted with halo (e.g., —F or —Cl), haloalkyl (e.g., —$CF_3$), N-sulfonamido (e.g. —$NHSO_2$-aryl, wherein the aryl group can be optionally substituted) or cyano. Even more preferably, said substituent(s) A' is/are each independently phenyl, —$CH_2$-phenyl, —O—$CH_2$-phenyl, —NH—$CH_2$-phenyl or —O—$(CH_2)_2$-phenyl, wherein said phenyl or the phenyl moiety in said —$CH_2$-phenyl, said —O—$CH_2$-phenyl, said —NH—$CH_2$-phenyl or said —O—$(CH_2)_2$-phenyl is optionally substituted with halo (e.g., —F or —Cl), haloalkyl (e.g., —$CF_3$), N-sulfonamido (e.g. —$NHSO_2$-aryl, wherein the aryl group can be optionally substituted) or cyano. Even more preferably, said substituent(s) A' is/are each independently phenyl, —$CH_2$-phenyl, or —O—$CH_2$-phenyl, wherein said phenyl or the phenyl moiety in said —$CH_2$-phenyl or said —O—$CH_2$-phenyl is optionally substituted with halo (e.g., —F or —Cl) or haloalkyl (e.g., —$CF_3$).

It is particularly preferred that A is aryl (preferably phenyl) or heteroaryl (preferably pyridinyl or thiazolyl), which aryl or heteroaryl optionally has one substituent A' selected from -$L^1$-aryl, -$L^1$-cycloalkyl, -$L^1$-heteroaryl or -$L^1$-heterocycloalkyl (wherein the aryl moiety in said -$L^1$-aryl, the cycloalkyl moiety in said -$L^1$-cycloalkyl, the heteroaryl moiety in said -$L^1$-heteroaryl or the heterocycloalkyl moiety in said -$L^1$-heterocycloalkyl may be substituted with halo (e.g., —F or —Cl), haloalkyl (e.g., —$CF_3$) or cyano), preferably selected from phenyl, —$CH_2$-phenyl or —O—$CH_2$-phenyl (wherein said phenyl, the phenyl moiety in said —$CH_2$-phenyl or the phenyl moiety in said —O—$CH_2$-phenyl may be substituted with halo (e.g., —F or —Cl) or haloalkyl (e.g., —$CF_3$)).

B is —H, -$L^2$-CO—$NH_2$, -$L^2$-CO—$NR^1R^2$, -$L^2$-CO—$R^3$ or -$L^2$-cyclyl, wherein the cyclyl moiety in said -$L^2$-cyclyl is optionally substituted with one or more (e.g., one, two or three) groups independently selected from halo, haloalkyl, haloalkoxy, haloaryl, aryl, arylalkoxy, aryloxy, arylalkyl, alkyl, alkenyl, alkynyl, alkoxy, amino, amido (e.g., —CO—

$NH_2$), alkylamino, hydroxyl, nitro, —$CH_2$—CO—$NH_2$, heteroaryl, heteroarylalkoxy, heteroaryloxy, heteroarylalkyl, cycloalkyl, cycloalkylalkoxy, cycloalkoxy, cycloalkylalkyl, heterocycloalkyl, heterocycloalkylalkoxy, heterocycloalkoxy, heterocycloalkylalkyl, cyano, cyanato, isocyanato, thiocyanato, isothiocyanato, sulfonyl, sulfinyl, sulfonamide, trihalomethanesulfonamido, acyl, acylamino, acyloxy, alkylthio, cycloalkylthio, heterocycloalkylthio, arylthio, heteroarylthio, carboxyl, carbamate or urea, preferably selected from halo, alkyl, alkoxy, haloalkyl, haloalkoxy, cyano, hydroxyl, amino, alkylamino, aminoalkyl, amido (e.g., —CO—$NH_2$), —$CH_2$—CO—$NH_2$, or sulfonamide.

It is preferred that the cyclyl moiety in said -$L^2$-cyclyl is unsubstituted or is substituted with one group selected from halo, haloalkyl, haloalkoxy, haloaryl, aryl, arylalkoxy, aryloxy, arylalkyl, alkyl, alkenyl, alkynyl, alkoxy, amino, amido (e.g., —CO—$NH_2$), alkylamino, hydroxyl, nitro, —$CH_2$—CO—$NH_2$, heteroaryl, heteroarylalkoxy, heteroaryloxy, heteroarylalkyl, cycloalkyl, cycloalkylalkoxy, cycloalkoxy, cycloalkylalkyl, heterocycloalkyl, heterocycloalkylalkoxy, heterocycloalkoxy, heterocycloalkylalkyl, cyano, cyanato, isocyanato, thiocyanato, isothiocyanato, sulfonyl, sulfinyl, sulfonamide, trihalomethanesulfonamido, acyl, acylamino, acyloxy, alkylthio, cycloalkylthio, heterocycloalkylthio, arylthio, heteroarylthio, carboxyl, carbamate or urea, preferably selected from halo, alkyl, alkoxy, haloalkyl, haloalkoxy, cyano, hydroxyl, amino, alkylamino, aminoalkyl, amido (e.g., —CO—$NH_2$), —$CH_2$—CO—$NH_2$, or sulfonamide.

The cyclyl moiety in said -$L^2$-cyclyl, which may be substituted as defined and described above, is preferably selected from aryl, cycloalkyl or heterocyclyl (e.g., heteroaryl or heterocycloalkyl), more preferably from cycloalkyl or heterocyclyl, still more preferably from heterocyclyl, even more preferably from heteroaryl or heterocycloalkyl. Said heteroaryl is preferably selected from oxadiazolyl, thiazolyl or pyrimidinyl. Said heterocycloalkyl is preferably selected from pyrrolidinyl, piperidinyl, piperazinyl, N-methylpiperazinyl or morpholinyl.

In formula (I), $R^1$ and $R^2$ are each independently chosen from —H, alkyl, alkynyl, alkenyl, -L-carbocycle, -L-aryl, -L-heterocyclyl, wherein said alkyl, said alkynyl or said alkenyl is optionally substituted with one or more groups independently selected from halo, haloalkoxy, haloaryl, aryl, arylalkoxy, aryloxy, alkoxy, amino, amido, alkylamino, hydroxyl, nitro, —$CH_2$—CO—$NH_2$, heteroaryl, heteroarylalkoxy, heteroaryloxy, cycloalkyl, cycloalkylalkoxy, cycloalkoxy, heterocycloalkyl, heterocycloalkylalkoxy, heterocycloalkoxy, cyano, cyanato, isocyanato, thiocyanato, isothiocyanato, sulfonyl, sulfinyl, sulfonamide, trihalomethanesulfonamido, acyl, acylamino, acyloxy, alkylthio, cycloalkylthio, heterocycloalkylthio, arylthio, heteroarylthio, carboxyl, carbamate or urea, and further wherein the carbocycle moiety in said -L-carbocycle, the aryl moiety in said -L-aryl, or the heterocyclyl moiety in said -L-heterocyclyl is optionally substituted with one or more groups independently selected from halo, haloalkyl, haloalkoxy, haloaryl, aryl, arylalkoxy, aryloxy, arylalkyl, alkyl, alkenyl, alkynyl, alkoxy, amino, amido, alkylamino, hydroxyl, nitro, —$CH_2$—CO—$NH_2$, heteroaryl, heteroarylalkoxy, heteroaryloxy, heteroarylalkyl, cycloalkyl, cycloalkylalkoxy, cycloalkoxy, cycloalkylalkyl, heterocycloalkyl, heterocycloalkylalkoxy, heterocycloalkoxy, heterocycloalkylalkyl, cyano, cyanato, isocyanato, thiocyanato, isothiocyanato, sulfonyl, sulfinyl, sulfonamide, trihalomethanesulfonamido, acyl, acylamino, acyloxy, alkylthio, cycloalkylthio, heterocycloalkylthio, arylthio, heteroarylthio, carboxyl, carbamate or urea.

In formula (I), $R^3$ is chosen from —H, alkoxy, -L-carbocyclic, -L-heterocyclic, -L-aryl, wherein the carbocyclic moiety in said -L-carbocyclic, the heterocyclic moiety in said -L-heterocyclic or the aryl moiety in said -L-aryl is optionally substituted with one or more groups independently selected from halo, haloalkyl, haloalkoxy, haloaryl, aryl, arylalkoxy, aryloxy, arylalkyl, alkyl, alkenyl, alkynyl, alkoxy, amino, amido, alkylamino, hydroxyl, nitro, —$CH_2$—CO—$NH_2$, heteroaryl, heteroarylalkoxy, heteroaryloxy, heteroarylalkyl, cycloalkyl, cycloalkylalkoxy, cycloalkoxy, cycloalkylalkyl, heterocycloalkyl, heterocycloalkylalkoxy, heterocycloalkoxy, heterocycloalkylalkyl, cyano, cyanato, isocyanato, thiocyanato, isothiocyanato, sulfonyl, sulfinyl, sulfonamide, trihalomethanesulfonamido, acyl, acylamino, acyloxy, alkylthio, cycloalkylthio, heterocycloalkylthio, arylthio, heteroarylthio, carboxyl, carbamate or urea. $R^3$ is preferably -L-heterocyclic, and more preferably -L-heterocycloalkyl, wherein the heterocyclic moiety in said -L-heterocyclic or the heterocycloalkyl moiety in said -L-heterocycloalkyl is optionally substituted, as defined above. Even more preferably, $R^3$ is -L-heterocycloalkyl, wherein the heterocycloalkyl moiety comprised in said -L-heterocycloalkyl is selected from pyrrolidinyl, piperidinyl, piperazinyl, N-methylpiperazinyl or morpholinyl, and is optionally substituted as defined above. The optional substituents in $R^3$ are preferably selected from halo, alkyl, alkoxy, haloalkyl, haloalkoxy, cyano, hydroxyl, amino, alkylamino, aminoalkyl, amido (e.g., —CO—$NH_2$), —$CH_2$—CO—$NH_2$, or sulfonamide.

Each L is independently selected from —$(CH_2)_n$—, —$(CH_2)_nC(=O)(CH_2)_n$—, —$(CH_2)_nC(=O)NH(CH_2)_n$—, —$(CH_2)_nNHC(=O)O(CH_2)_n$—, —$(CH_2)_nNHC(=O)NH(CH_2)_n$—, —$(CH_2)_nNHC(=S)S(CH_2)_n$—, —$(CH_2)_nOC(=O)S(CH_2)_n$—, —$(CH_2)_nNH(CH_2)_n$—, —$(CH_2)_nO(CH_2)_n$—, —$(CH_2)_nS(CH_2)_n$—, and —$(CH_2)_nNHC(=S)NH(CH_2)_n$—, and each n is independently chosen from 0, 1, 2, 3, 4, 5, 6, 7, and 8. Preferably, each L in $R^1$ and $R^2$ is independently —$(CH_2)_{1-6}$—, more preferably —$(CH_2)_{1-4}$—, and even more preferably —$CH_2$—. Moreover, L in $R^3$ is preferably a covalent bond or —$(CH_2)_{1-4}$—, more preferably a covalent bond or —$(CH_2)_{1-4}$—, and even more preferably a covalent bond.

$L^2$ is $C_{1-12}$ alkylene which is optionally interrupted by one or more (e.g., one, two, three or four) groups independently selected from —O—, —S—, —NH—, —N(alkyl)-, —CO—, —CO—NH— or —CO—N(alkyl)-, or $L^2$ is a covalent bond. Preferably, $L^2$ is —$CH_2$—($C_{1-6}$alkylene), —$CH_2$—CO— or a covalent bond, wherein the alkylene moiety in said —$CH_2$—($C_{1-6}$ alkylene) is optionally interrupted by one or more (e.g., one, two or three) groups independently selected from —O—, —S—, —NH—, —N(alkyl)-, —CO—, —CO—NH—, —CO—N(alkyl)-. More preferably, $L^2$ is —$(CH_2)_{1-4}$—, —$CH_2$—CO— or a covalent bond. Even more preferably, $L^2$ is —$CH_2$—, —$(CH_2)_2$—, —$CH_2$—CO— or a covalent bond.

Preferably, B is —H, —$(CH_2)_{1-4}$—CO—$NH_2$, —$(CH_2)_{1-4}$—CO—$NR^1R^2$, —$(CH_2)_{0-5}$-heteroaryl, —$(CH_2)_{0-5}$-heterocycloalkyl or —$(CH_2)_{1-5}$—CO-heterocycloalkyl, wherein the heteroaryl moiety comprised in said —$(CH_2)_{0-5}$-heteroaryl or the heterocycloalkyl moiety comprised in said —$(CH_2)_{0-5}$-heterocycloalkyl or in said —$(CH_2)_{1-5}$—CO-heterocycloalkyl is optionally substituted with one group selected from halo, alkyl, alkoxy, haloalkyl, haloalkoxy, cyano, hydroxyl, amino, alkylamino, aminoalkyl, amido (e.g., —CO—NH$_2$), —CH$_2$—CO—NH$_2$, or sulfonamide.

In a particularly preferred embodiment, B is —H. In a further particularly preferred embodiment, B is —(CH$_2$)$_{1-4}$—CO—NH$_2$, more preferably —CH$_2$—CO—NH$_2$. In a further particularly preferred embodiment, B is —(CH$_2$)$_{1-4}$—CO—NR$^1$R$^2$, more preferably —CH$_2$—CO—NR$^1$R$^2$. In a further particularly preferred embodiment, B is —(CH$_2$)$_{0-5}$-heteroaryl, wherein the heteroaryl moiety comprised in said —(CH$_2$)$_{0-5}$-heteroaryl is preferably selected from oxadiazolyl, thiazolyl or pyrimidinyl and, furthermore, is optionally substituted with one group selected from halo, alkyl, alkoxy, haloalkyl, haloalkoxy, cyano, hydroxyl, amino, alkylamino, aminoalkyl, amido (e.g., —CO—NH$_2$), —CH$_2$—CO—NH$_2$, or sulfonamide. In a further particularly preferred embodiment, B is —(CH$_2$)$_{0-5}$-heterocycloalkyl, wherein the heterocycloalkyl moiety comprised in said —(CH$_2$)$_{0-5}$-heterocycloalkyl is preferably selected from pyrrolidinyl, piperidinyl, piperazinyl, N-methylpiperazinyl or morpholinyl and, furthermore, is optionally substituted with one group selected from halo, alkyl, alkoxy, haloalkyl, haloalkoxy, cyano, hydroxyl, amino, alkylamino, aminoalkyl, amido (e.g., —CO—NH$_2$), —CH$_2$—CO—NH$_2$, or sulfonamide. In a further particularly preferred embodiment, B is —CH$_2$-oxadiazolyl, wherein the oxadiazolyl moiety comprised in said —CH$_2$-oxadiazolyl is optionally substituted with one group selected from halo, alkyl, alkoxy, haloalkyl, haloalkoxy, cyano, hydroxyl, amino, alkylamino or aminoalkyl (accordingly, B may, for example, be aminooxadiazolylmethyl, such as 2-amino-1,3,4-oxadiazol-5-ylmethyl or 3-amino-1,2,4-oxadiazol-5-ylmethyl). In a further particularly preferred embodiment, B is —(CH$_2$)$_{1-5}$—CO-heterocycloalkyl, wherein the heterocycloalkyl moiety comprised in said —(CH$_2$)$_{1-5}$—CO-heterocycloalkyl is preferably selected from pyrrolidinyl, piperidinyl, piperazinyl, N-methylpiperazinyl or morpholinyl and, furthermore, is optionally substituted with one group selected from halo, alkyl, alkoxy, haloalkyl, haloalkoxy, cyano, hydroxyl, amino, alkylamino, aminoalkyl, amido (e.g., —CO—NH$_2$), —CH$_2$—CO—NH$_2$, or sulfonamide.

The substituents on the cyclopropane ring, i.e. the groups -(A) and —NH—B, are preferably in trans configuration. In that case, the 2-cyclylcyclopropan-1-amine compound of formula (I) may have the configuration (1R,2S) or the configuration (1S,2R) at the cyclopropane ring carbon atoms. The present invention specifically relates to the (1R,2S) stereoisomer of the 2-cyclylcyclopropan-1-amine compound of formula (I). The invention also specifically relates to the (1S,2R) stereoisomer of the 2-cyclylcyclopropan-1-amine compound of formula (I)

In one embodiment, the LSD1 inhibitor or selective LSD1 inhibitor or dual LSD1/MAO-B inhibitor to be used in accordance with the present invention is a 2-cyclylcyclopropan-1-amine compound which is a compound of the following formula (II) or a pharmaceutically acceptable salt thereof:

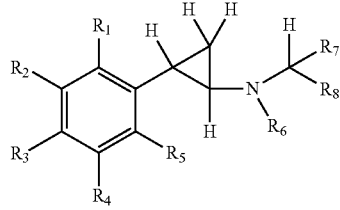

(II)

In formula (II), each of R1-R5 is optionally substituted and independently chosen from —H, halo, alkyl, alkoxy, cycloalkoxy, haloalkyl, haloalkoxy, -L-aryl, -L-heteroaryl, -L-heterocyclyl, -L-carbocycle, acylamino, acyloxy, alkylthio, cycloalkylthio, alkynyl, amino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamide, thiocarbonyl, thiocyanato, trihalomethanesulfonamido, O-carbamyl, N-carbamyl, O-thiocarbamyl, N-thiocarbamyl, and C-amido;

R6 is chosen from —H and alkyl;
R7 is chosen from —H, alkyl, and cycloalkyl;
R8 is chosen from —C(=O)NR$_x$R$_y$ and —C(=O)R$_z$;
R$_x$ when present is chosen from —H, alkyl, alkynyl, alkenyl, -L-carbocycle, -L-aryl, -L-heterocyclyl, all of which are optionally substituted;
R$_y$ when present is chosen from —H, alkyl, alkynyl, alkenyl, -L-carbocycle, -L-aryl, -L-heterocyclyl, all of which are optionally substituted;
R$_z$ when present is chosen from —H, alkoxy, -L-carbocyclic, -L-heterocyclic, -L-aryl, wherein the aryl, heterocyclyl, or carbocycle is optionally substituted;
each L can be saturated, partially saturated, or unsaturated, and is independently chosen from —(CH$_2$)$_n$—(CH$_2$)$_n$—, —(CH$_2$)$_n$C(=O)(CH$_2$)$_n$—, —(CH$_2$)$_n$C(=O)NH(CH$_2$)$_n$—, —(CH$_2$)$_n$NHC(=O)O(CH$_2$)$_n$—, —(CH$_2$)$_n$NHC(=O)NH(CH$_2$)$_n$—, —(CH$_2$)$_n$NHC(=S)S(CH$_2$)$_n$—, —(CH$_2$)$_n$OC(=O)S(CH$_2$)$_n$—, —(CH$_2$)$_n$NH(CH$_2$)$_n$—, —(CH$_2$)$_n$—O—(CH$_2$)$_n$—, —(CH$_2$)$_n$S(CH$_2$)$_n$—, and —(CH$_2$)$_n$NHC(=S)NH(CH$_2$)$_n$—, where each n is independently chosen from 0, 1, 2, 3, 4, 5, 6, 7, and 8, wherein optionally substituted refers to zero or 1 to 4 optional substituents independently chosen from acylamino, acyloxy, alkenyl, alkoxy, cycloalkoxy, alkyl, alkylthio, cycloalkylthio, alkynyl, amino, aryl, arylalkyl, arylalkenyl, arylalkynyl, arylalkoxy, aryloxy, arylthio, heteroarylthio, carbocyclyl, cyano, cyanato, halo, haloalkyl, haloaryl, hydroxyl, heteroaryl, heteroaryloxy, heterocyclyl, heteroarylalkoxy, isocyanato, isothiocyanato, nitro, sulfinyl, sulfonyl, sulfonamide, thiocarbonyl, thiocyanato, trihalomethanesulfonamido, O-carbamyl, N-carbamyl, O-thiocarbamyl, N-thiocarbamyl, and C-amido.

In a further embodiment, the LSD1 inhibitor or selective LSD1 inhibitor or dual LSD1/MAO-B inhibitor to be used in accordance with the invention is a 2-cyclylcyclopropan-1-amine compound which is a compound of the following formula (III) or a pharmaceutically acceptable salt thereof:

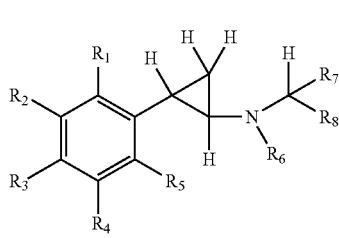

(III)

In formula (III), each of R1-R5 is independently chosen from —H, halo, alkyl, alkoxy, cycloalkoxy, haloalkyl, haloalkoxy, -L-aryl, -L-heterocyclyl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido;

R6 is chosen from —H and alkyl;

R7 is chosen from —H, alkyl, and cycloalkyl;

R8 is a -L-heterocyclyl wherein the ring or ring system of said -L-heterocyclyl has from 0-3 substituents chosen from halo, alkyl, alkoxy, cycloalkoxy, haloalkyl, haloalkoxy, -L-aryl, -L-heterocyclyl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido; or R8 is -L-aryl wherein the ring or ring system of said -L-aryl has from 1-3 substituents chosen from halo, alkyl, alkoxy, cycloalkoxy, haloalkyl, haloalkoxy, -L-aryl, -L-heterocyclyl, -L-carbocyclyl, acylamino, acyloxy, alkylthio, cycloalkylthio, alkynyl, amino, alkylamino, aryl, arylalkyl, arylalkenyl, arylalkynyl, arylalkoxy, aryloxy, arylthio, heteroarylthio, cyano, cyanato, haloaryl, hydroxyl, heteroaryloxy, heteroarylalkoxy, isocyanato, isothiocyanato, nitro, sulfinyl, sulfonyl, sulfonamido, thiocarbonyl, thiocyanato, trihalomethanesulfonamido, O-carbamyl, N-carbamyl, O-thiocarbamyl, N-thiocarbamyl, and C-amido;

each L is independently chosen from —(CH$_2$)$_n$—(CH$_2$)$_n$—, —(CH$_2$)$_n$NH(CH$_2$)$_n$—, —(CH$_2$)$_n$O(CH$_2$)$_n$—, and —(CH$_2$)$_n$S(CH$_2$)$_n$—, and where each n is independently chosen from 0, 1, 2, and 3.

In a further embodiment, the LSD1 inhibitor or selective LSD1 inhibitor or dual LSD1/MAO-B inhibitor to be used in accordance with the invention is a 2-cyclylcyclopropan-1-amine compound which is a compound of the following formula (IV) or an enantiomer, diastereomer, or mixture thereof, or a pharmaceutically acceptable salt or solvate thereof:

(A')$_X$-(A)-(B)—(Z)-(L)-(D)        (IV)

In formula (IV), (A) is heteroaryl or aryl;

each (A'), if present, is independently chosen from aryl, arylalkoxy, arylalkyl, heterocyclyl, aryloxy, halo, alkoxy, haloalkyl, cycloalkyl, haloalkoxy, and cyano, wherein each (A') is substituted with 0, 1, 2, or 3 substituents independently chosen from halo, haloalkyl, aryl, arylalkoxy, alkyl, alkoxy, cyano, sulfonyl, amido, and sulfinyl;

X is 0, 1, 2, or 3;

(B) is a cyclopropyl ring, wherein (A) and (Z) are covalently bonded to different carbon atoms of (B);

(Z) is —NH—;

(L) is chosen from —CH$_2$CH$_2$—, —CH$_2$CH$_2$CH$_2$—, and —CH$_2$CH$_2$CH$_2$CH$_2$—; and (D) is chosen from —N(—R1)-R2, —O—R3, and —S—R3, wherein:

R1 and R2 are mutually linked to form a heterocyclic ring together with the nitrogen atom that R1 and R2 are attached to, wherein said heterocyclic ring has 0, 1, 2, or 3 substituents independently chosen from —NH$_2$, —NH(C$_1$-C$_6$ alkyl), —N(C$_1$-C$_6$ alkyl)(C$_1$-C$_6$ alkyl), alkyl, halo, cyano, alkoxy, haloalkyl, and haloalkoxy, or R1 and R2 are independently chosen from —H, alkyl, cycloalkyl, haloalkyl, and heterocyclyl, wherein the sum of substituents on R1 and R2 together is 0, 1, 2, or 3, and the substituents are independently chosen from —NH$_2$, —NH(C$_1$-C$_6$ alkyl), —N(C$_1$-C$_6$ alkyl)(C$_1$-C$_6$ alkyl), and fluoro; and R3 is chosen from —H, alkyl, cycloalkyl, haloalkyl, and heterocyclyl, wherein R3 has 0, 1, 2, or 3 substituents independently chosen from —NH$_2$, —NH(C$_1$-C$_6$ alkyl), —N(C$_1$-C$_6$ alkyl)(C$_1$-C$_6$ alkyl), and fluoro;

with the proviso that the following compounds are excluded:

N1-[(trans)-2-phenylcyclopropyl]-N2-undecyl-rel-1,2-ethanediamine;

N1-[(trans)-2-phenylcyclopropyl]-N2-tricyclo[3.3.1.13,7]dec-2-yl-rel-1,2-ethanediamine;

N1-cyclooctyl-N2-[(trans)-2-phenylcyclopropyl]-rel-1,2-ethanediamine;

N1,N1-dimethyl-N2-(2-phenylcyclopropyl)-1,3-propanediamine;

N1,N1-dimethyl-N2-(2-phenylcyclopropyl)-1,2-ethanediamine; and trans-1-phenyl-2-[(2-hydroxyethyl)amino]cyclopropane.

In a further embodiment, the LSD1 inhibitor or selective LSD1 inhibitor or dual LSD1/MAO-B inhibitor to be used in accordance with the invention is a 2-cyclylcyclopropan-1-amine compound which is a compound of the following formula (V) or a pharmaceutically acceptable salt or solvate thereof:

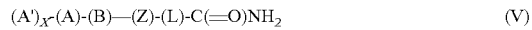

(A')$_X$-(A)-(B)—(Z)-(L)-C(=O)NH$_2$        (V)

In formula (V), (A) is heteroaryl or aryl;

each (A'), if present, is independently chosen from aryl, arylalkoxy, arylalkyl, heterocyclyl, aryloxy, halo, alkoxy, haloalkyl, cycloalkyl, haloalkoxy, and cyano, wherein each (A') is substituted with 0, 1, 2 or 3 substituents independently chosen from halo, haloalkyl, aryl, arylalkoxy, alkyl, alkoxy, cyano, sulfonyl, sulfinyl, and carboxamide;

X is 0, 1, 2, or 3;

(B) is a cyclopropyl ring, wherein (A) and (Z) are covalently bonded to different carbon atoms of (B);

(Z) is —NH—; and (L) is —(CH$_2$)$_m$CR$_1$R$_2$—, wherein m is 0, 1, 2, 3, 4, 5, or 6, and wherein R$_1$ and R$_2$ are each independently hydrogen or C$_1$-C$_6$ alkyl;

provided that, if (L) is —CH$_2$— or —CH(CH$_3$)—, then X is not 0.

In a further embodiment, the LSD1 inhibitor or selective LSD1 inhibitor or dual LSD1/MAO-B inhibitor to be used in accordance with the invention is a 2-cyclylcyclopropan-1-amine compound which is a compound of the following formula (VI) or an enantiomer, a diastereomer, or a mixture thereof, or a pharmaceutically acceptable salt or solvate thereof:

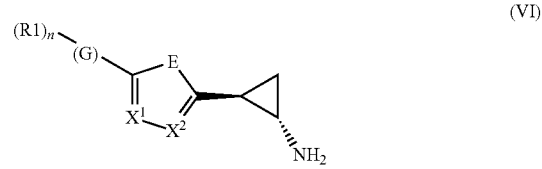

(VI)

In formula (VI), E is —N(R3)-, —O—, or —S—, or is —X$^3$=X$^4$—;

X$^1$ and X$^2$ are independently C(R2) or N;

X$^3$ and X$^4$, when present, are independently C(R2) or N;

(G) is a cyclyl group;

each (R1) is independently chosen from alkyl, alkenyl, alkynyl, cyclyl, -L1-cyclyl, -L1-amino, -L1-hydroxyl, amino, amido, nitro, halo, haloalkyl, haloalkoxy, cyano, sulfinyl, sulfonyl, sulfonamide, hydroxyl, alkoxy, urea, carbamate, acyl, or carboxyl;

each (R2) is independently chosen from —H, alkyl, alkenyl, alkynyl, cyclyl, -L1-cyclyl, -L1-amino, -L1-hydroxyl, amino, amido, nitro, halo, haloalkyl, haloalkoxy, cyano, sulfinyl, sulfonyl, sulfonamide, hydroxyl, alkoxy, urea, carbamate, acyl, or carboxyl, wherein each (R2) group has 1, 2, or 3 independently chosen optional substituents or two (R2) groups can be taken together to form a heterocyclyl or aryl group having 1, 2, or 3 independently chosen optional substituents, wherein said optional substituents are independently chosen from alkyl, alkanoyl, heteroalkyl, heterocyclyl, haloalkyl, cycloalkyl, carbocyclyl, arylalkoxy, heterocyclylalkoxy, aryl, aryloxy, heterocyclyloxy, alkoxy, haloalkoxy, oxo, acyloxy, carbonyl, carboxyl, carboxamido, cyano, halogen, hydroxyl, amino, aminoalkyl, amidoalkyl, amido, nitro, thiol, alkylthio, arylthio, sulfonamide, sulfinyl, sulfonyl, urea, or carbamate;

R3 is —H or a ($C_1$-$C_6$)alkyl group;

each L1 is independently alkylene or heteroalkylene; and n is 0, 1, 2, 3, 4 or 5.

In a further embodiment, the LSD1 inhibitor or selective LSD1 inhibitor or dual LSD1/MAO-B inhibitor to be used in accordance with the invention is a 2-cyclylcyclopropan-1-amine compound which is a compound of the following formula (VII) or an enantiomer, a diastereomer, or a mixture thereof, or a pharmaceutically acceptable salt or solvate thereof:

(VII)

In formula (VII), (A) is heteroaryl or aryl;

each (A'), if present, is independently chosen from aryl, arylalkoxy, arylalkyl, heterocyclyl, aryloxy, halo, alkoxy, haloalkyl, cycloalkyl, haloalkoxy, and cyano, wherein each (A') is substituted with 0, 1, 2, or 3 substituents independently chosen from halo, haloalkyl, haloalkoxy, aryl, arylalkoxy, alkyl, alkoxy, amido, —CH$_2$C(=O)NH$_2$, heteroaryl, cyano, sulfonyl, and sulfinyl;

X is 0, 1, 2, or 3;

(B) is a cyclopropyl ring, wherein (A) and (Z) are covalently bonded to different carbon atoms of (B);

(Z) is —NH—;

(L) is chosen from a single bond, —CH$_2$—, —CH$_2$CH$_2$—, —CH$_2$CH$_2$CH$_2$—, and —CH$_2$CH$_2$CH$_2$CH$_2$—; and (D) is an aliphatic carbocyclic group or benzocycloalkyl, wherein said aliphatic carbocyclic group or said benzocycloalkyl has 0, 1, 2, or 3 substituents independently chosen from —NH$_2$, —NH(C$_1$-C$_6$ alkyl), —N(C$_1$-C$_6$ alkyl)(C$_1$-C$_6$ alkyl), alkyl, halo, amido, cyano, alkoxy, haloalkyl, and haloalkoxy;

with the proviso that the following compounds are excluded:

N-(2-phenylcyclopropyl)-cyclopentanamine;

10,11-dihydro-N-(2-phenylcyclopropyl)-5H-dibenzo[a,d]cyclohepten-5-amine; and trans-N-(2-phenylcyclopropyl)-cyclohexanamine.

In a further embodiment, the LSD1 inhibitor or selective LSD1 inhibitor or dual LSD1/MAO-B inhibitor to be used in accordance with the invention is a 2-cyclylcyclopropan-1-amine compound which is a compound of the following formula (VIII) or a pharmaceutically acceptable salt or solvate thereof:

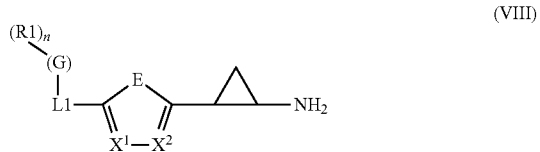

(VIII)

In formula (VIII), E is —X$^3$=X$^4$—, —N(R3)-, —S—, or —O—;

X$^1$ and X$^2$ are each independently C(R2) or N:

X$^3$ and X$^4$, when present, are each independently C(R2) or N;

L is —NH— or —NH—CH$_2$—;

G is a cyclyl group;

each R1 is independently chosen from alkyl, alkenyl, alkynyl, cyclyl, -L2-cyclyl, -L2-amino, -L2-hydroxyl, amino, amido, nitro, halo, haloalkyl, haloalkoxy, cyano, sulfinyl, sulfonyl, sulfonamide, hydroxyl, alkoxy, urea, carbamate, acyl, or carboxyl;

each R2 is independently chosen from —H, alkyl, alkenyl, alkynyl, cyclyl, -L2-cyclyl, -L2-amino, -L2-hydroxyl, amino, amido, nitro, halo, haloalkyl, haloalkoxy, cyano, sulfinyl, sulfonyl, sulfonamide, hydroxyl, alkoxy, urea, carbamate, acyl, or carboxyl, wherein each R2 group has 1, 2, or 3 independently chosen optional substituents, and further wherein two R2 groups bound to adjacent carbon atoms can be taken together to form a heterocyclyl or aryl group having 1, 2, or 3 independently chosen optional substituents; wherein said optional substituents are each independently chosen from alkyl, alkanoyl, heteroalkyl, heterocyclyl, haloalkyl, cycloalkyl, carbocyclyl, arylalkoxy, heterocyclylalkoxy, aryl, aryloxy, heterocyclyloxy, alkoxy, haloalkoxy, oxo, acyloxy, carbonyl, carboxyl, carboxamido, cyano, halogen, hydroxyl, amino, aminoalkyl, amidoalkyl, amido, nitro, thiol, alkylthio, arylthio, sulfinyl, sulfonyl, sulfonamide, urea or carbamate;

R3 is —H or an (C1-C6)alkyl group;

each L2 is independently chosen from alkylene or heteroalkylene; and n is 0, 1, 2, 3, 4 or 5.

In a further embodiment, the LSD1 inhibitor or selective LSD1 inhibitor or dual LSD1/MAO-B inhibitor to be used in accordance with the invention is a 2-cyclylcyclopropan-1-amine compound which is a compound of the following formula (IX) or a pharmaceutically acceptable salt or solvate thereof:

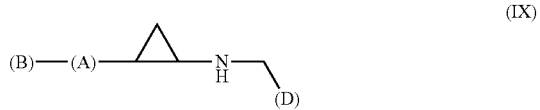

(IX)

In formula (IX), (A) is a cyclyl group having n substituents (R3);

(B) is a cyclyl group or an -(L1)-cyclyl group, wherein said cyclyl group or the cyclyl moiety comprised in said -(L1)-cyclyl group has n substituents (R2);

(L1) is —O—, —NH—, —N(alkyl)-, alkylene or heteroalkylene;

(D) is a heteroaryl group or an -(L2)-heteroaryl group, wherein said heteroaryl group or the heteroaryl moiety comprised in said -(L2)-heteroaryl group has one substituent (R1), and further wherein said heteroaryl group is covalently bonded to the remainder of the molecule through a ring carbon atom or the heteroaryl moiety comprised in said -(L2)-heteroaryl group is covalently bonded to the (L2) moiety through a ring carbon atom;

(L2) is —O—, —NH—, —N(alkyl)-, alkylene or heteroalkylene;

(R1) is a hydrogen bonding group;

each (R2) is independently selected from alkyl, alkenyl, alkynyl, cyclyl, amino, amido, C-amido, alkylamino, hydroxyl, nitro, halo, haloalkyl, haloalkoxy, cyano, sulfinyl, sulfonyl, sulfonamide, alkoxy, acyl, carboxyl, carbamate or urea;

each (R3) is independently selected from alkyl, alkenyl, alkynyl, cyclyl, amino, amido, C-amido, alkylamino, hydroxyl, nitro, halo, haloalkyl, haloalkoxy, cyano, sulfinyl, sulfonyl, sulfonamide, alkoxy, acyl, carboxyl, carbamate, or urea; and n is independently 0, 1, 2, 3 or 4.

Figure 2:
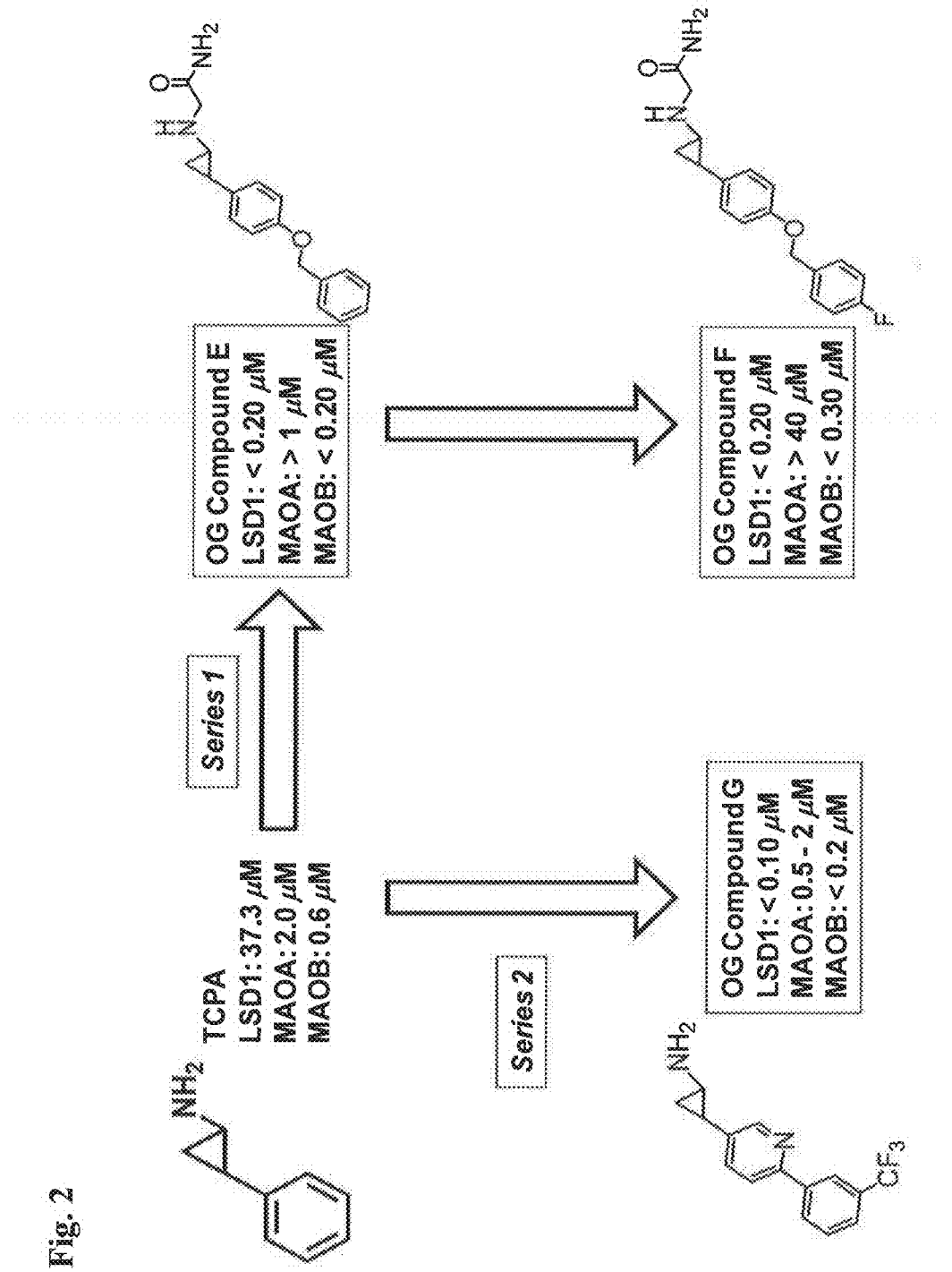
FIG. 2 Optimization of Dual LSD1/MAOB Inhibitors.
Figure 3:
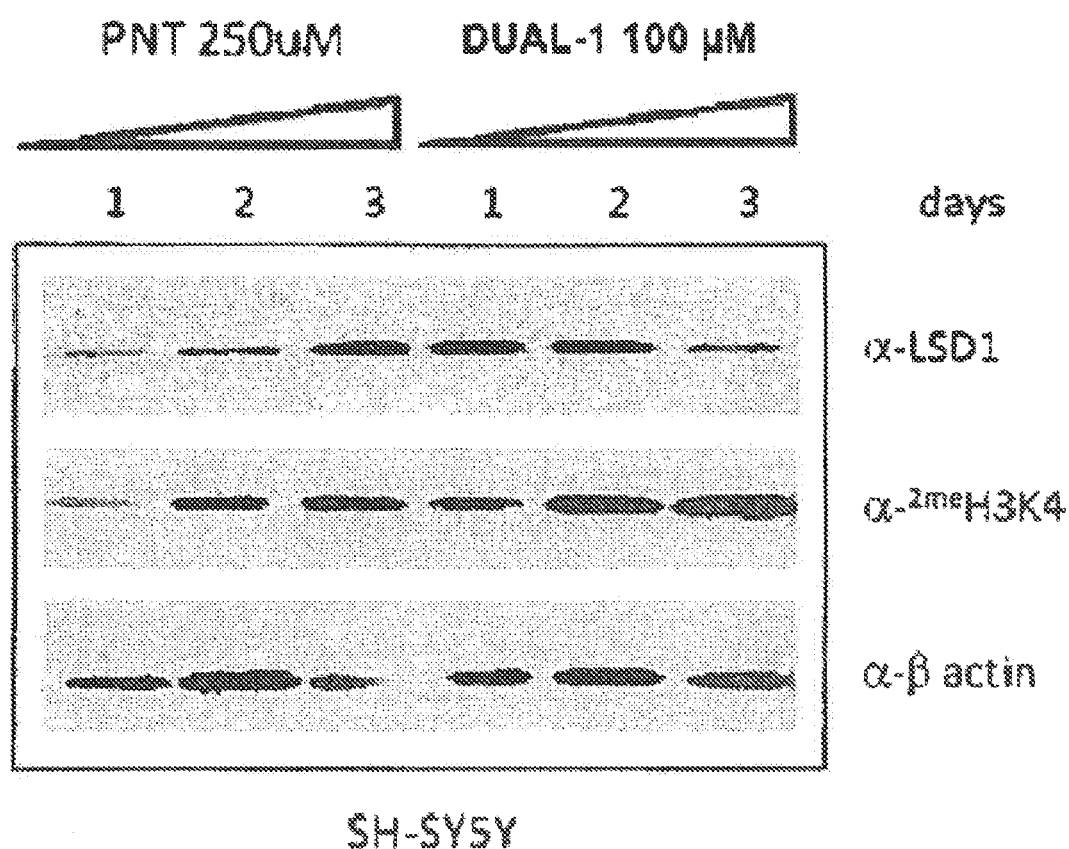
FIG. 3 Compound Dual-1 Increases Histone Methylation.
Figure 3:
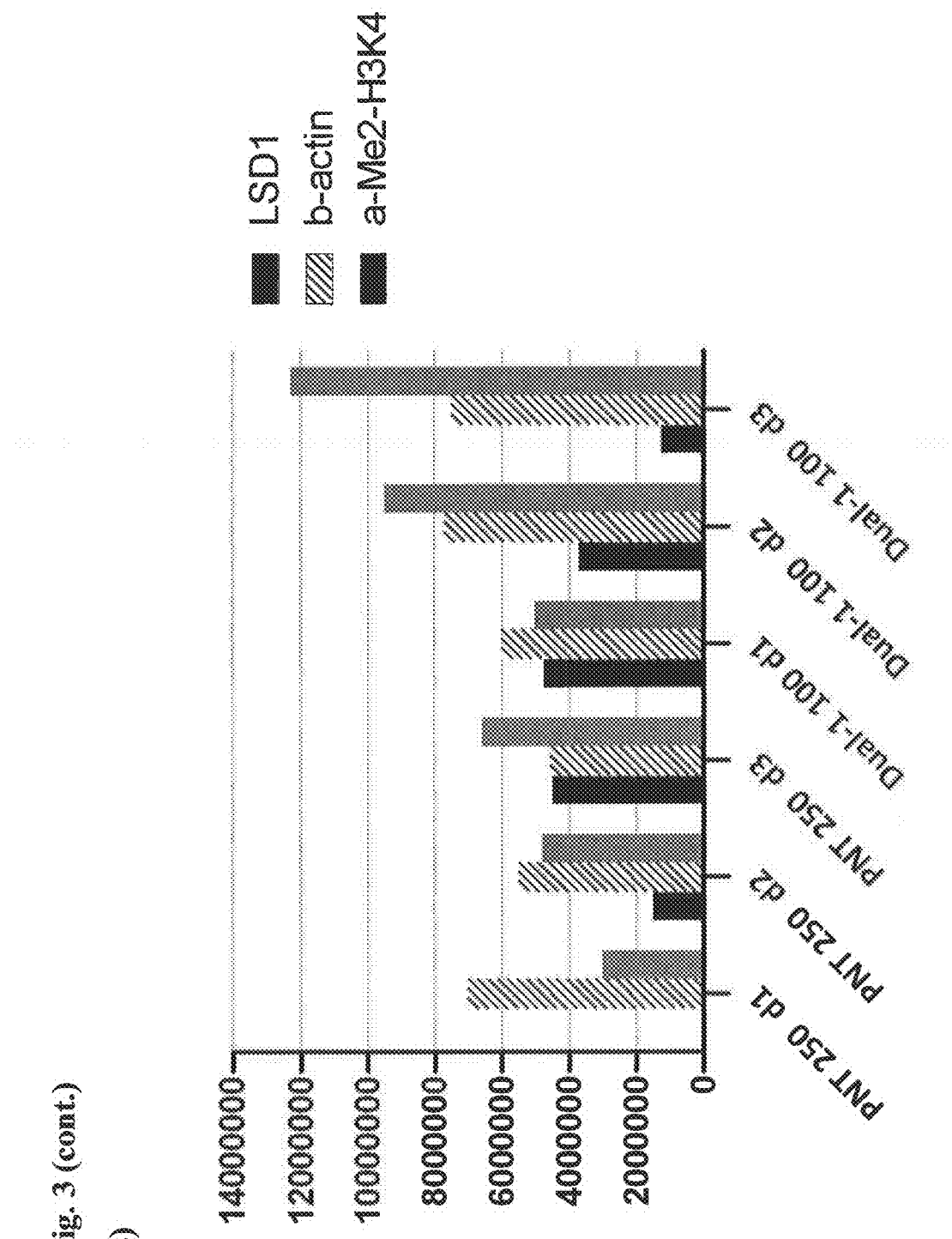

Exemplary non-limiting selective LSD1 inhibitors are OG Compounds A, B, C and D as shown in FIG. 1 and OG Compounds X and Y shown in Example 2, as well as pharmaceutically acceptable salts or solvates thereof. Exemplary non-limiting dual LSD1/MAO B selective inhibitors are OG Compounds E, F and G as shown in FIG. 2 and OG Compound Z as shown in Example 2, as well as pharmaceutically acceptable salts or solvates thereof.

The 2-cyclylcyclopropan-1-amine compounds disclosed and described herein, including, e.g., the compounds of formulae (I) to (IX), can be prepared by methods known in the art of synthetic chemistry. For example, these compounds can be prepared in accordance with or in analogy to the methods described in WO2010/043721, WO2010/084160, WO2011/035941, WO2011/042217, WO2011/131697, PCT/EP2011/062947, PCT/EP2011/062949, and PCT/EP2011/067608.

Any definition herein may be used in combination with any other definition to describe a composite structural group. By convention, the trailing element of any such definition is that which attaches to the parent moiety. For example, the composite group alkylamido would represent an alkyl group attached to the parent molecule through an amido group, and the term alkoxyalkyl would represent an alkoxy group attached to the parent molecule through an alkyl group.

As used herein, the term "aryl," refers a carbocyclic aromatic system containing one ring, or two or three rings fused together where in the ring atoms are all carbon. The term "aryl" groups includes, but is not limited to groups such as phenyl, naphthyl, or anthracenyl.

As used herein, the term "heterocyclyl" or "heterocycle," each refer to a saturated, partially unsaturated, or fully unsaturated monocyclic, bicyclic, or tricyclic heterocyclic group containing at least one heteroatom as a ring member, wherein each said heteroatom may be independently selected from the group consisting of nitrogen, oxygen, and sulfur wherein the nitron or sulfur atoms may be oxidized (e.g., —N—O, —S(=O)—, or —S(=O)$_2$—). Additionally, 1, 2, or 3 of the carbon atoms of the heterocyclyl may be optionally oxidized (e.g., to give an oxo group or =O). One group of heterocyclyls has from 1 to 4 heteroatoms as ring members. Another group of heterocyclyls has from 1 to 2 heteroatoms as ring members. One group of heterocyclyls has from 3 to 8 ring members in each ring. Yet another group of heterocyclyls has from 3 to 7 ring members in each ring. Again another group of heterocyclyls has from 5 to 6 ring members in each ring. "Heterocyclyl" is intended to encompass a heterocyclyl group fused to a carbocyclyl or benzo ring systems. Examples of heterocyclyl groups include, but are not limited to, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, or imidazolidinyl. Examples of heteroaryls that are heterocyclyls include, but are not limited to, pyridinyl, imidazolyl, imidazopyridinyl, pyrimidinyl, pyrazolyl, triazolyl, pyrazinyl, tetrazolyl, furyl, thienyl, isoxazolyl, thiazolyl, oxadiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, or furopyridinyl.

As used herein, the term "heteroaryl," refers to a 3 to 7 membered unsaturated monocyclic ring, or a fused bicyclic, or tricyclic ring system in which the rings are aromatic and in which at least one ring contains at least one atom selected from the group consisting of O, S, and N. One group of heteroaryls has from 5 to 7 ring atoms. Examples of heteroaryl groups include, but are not limited to, pyridinyl, imidazolyl, imidazopyridinyl, pyrimidinyl, pyrazolyl, triazolyl, pyrazinyl, tetrazolyl, furyl, thienyl, isoxazolyl, thiazolyl, oxadiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, or furopyridinyl.

As used herein, the term "acyl," refers to a carbonyl attached to an alkenyl, alkyl, aryl, cycloalkyl, heteroaryl, heterocyclyl, or any other moiety where the atom attached to the carbonyl is carbon. An "acetyl" group refers to a —C(=O)CH$_3$ group. An "alkylcarbonyl" or "alkanoyl" group refers to an alkyl group attached to the parent molecular moiety through a carbonyl group. Examples of such groups include, but are not limited to, methylcarbonyl or ethylcarbonyl. Examples of acyl groups include, but are not limited to, formyl, alkanoyl or aroyl.

As used herein, the term "alkenyl," refers to a straight-chain or branched-chain hydrocarbon group having one or more double bonds and containing from 2 to 20 carbon atoms. Exemplary alkenyl groups may have from 2 to 6 carbon atoms. A (C2-C6)alkenyl has from 2 to 6 carbon atoms.

As used herein, the term "alkoxy," refers to an alkyl ether group, wherein the term alkyl is as defined below. Exemplary alkoxy groups may have from 1 to 6 carbon atoms. Examples of suitable alkyl ether groups include, but are not limited to, methoxy, ethoxy, n-propoxy, isopropoxy, n-butoxy, iso-butoxy, sec-butoxy, tert-butoxy, or n-pentoxy.

As used herein, the term "alkyl," refers to a straight-chain or branched-chain alkyl group containing from 1 to 20 carbon atoms. Exemplary alkyl groups may have from 1 to 10 or, in particular, from 1 to 6 carbon atoms. A (C1-C10) alkyl has from 1 to 10 carbon atoms and a (C1-C6)alkyl has from 1 to 6 carbon atoms and a (C1-C4)alkyl has from 1 to 4 carbon atoms. Examples of alkyl groups include, but are not limited to, methyl, ethyl, n-propyl, isopropyl, n-butyl, isobutyl, sec-butyl, tert-butyl, pentyl, isopentyl, neo-pentyl, iso-amyl, hexyl, heptyl, octyl, or nonyl.

As used herein, the term "alkylene" refers to an alkyl group attached at two positions, i.e. an alkanediyl group. Exemplary alkylene groups may have from 1 to 6 carbon atoms. Examples include, but are not limited to, methylene, ethylene, propylene, butylene, pentylene, hexylene, heptylene, octylene, or nonylene.

As used herein, the term "alkylamino," refers to an alkyl group attached to the parent molecular moiety through an amino group. Suitable alkylamino groups may be mono- or dialkylated, forming groups including, but not limited to N-methylamino, N-ethylamino, N,N-dimethylamino, N,N-ethylmethylamino, N,N-diethylamino, N-propylamino, and N,N-methylpropylamino.

As used herein, the term "alkynyl," refers to a straight-chain or branched-chain hydrocarbon group having one or more triple bonds and containing from 2 to 20 carbon atoms. Exemplary alkynyl groups may have from 2 to 6 carbon atoms. A (C2-C6)alkynyl has from 2 to 6 carbon atoms. A (C2-C4)alkynyl has from 2 to 4 carbon atoms. Examples of alkynyl groups include, but are not limited to, ethynyl, propynyl, hydroxypropynyl, butyn-1-yl, butyn-2-yl, pentyn-1-yl, 3-methylbutyn-1-yl, or hexyn-2-yl.

As used herein, the terms "amido" and "carbamoyl," refer to an amino group as described below attached to the parent molecular moiety through a carbonyl group (e.g., —C(═O)NRR'), or vice versa (—N(R)C(═O)NR'). "Amido" and "carbamoyl" encompass "C-amido", "N-amido" and "acylamino" as defined herein. R and R' are as defined herein.

As used herein, the term "C-amido," refers to a —C(═O)NRR' group with R and R' as defined herein.

As used herein, the term "amino," refers to —NRR', wherein R and R' are independently selected from the group consisting of hydrogen, alkyl, heteroalkyl, aryl, carbocyclyl, and heterocyclyl, Additionally, R and R' may be combined to form a heterocyclyl.

As used herein, the term "arylalkoxy" or "aralkoxy," refers to an aryl group attached to the parent molecular moiety through an alkoxy group. Examples of arylalkoxy groups include, but are not limited to, benzyloxy or phenethoxy.

As used herein, the term "arylalkyl" or "aralkyl," refers to an aryl group attached to the parent molecular moiety through an alkyl group.

As used herein, the term "aryloxy," refers to an aryl group attached to the parent molecular moiety through an oxy (—O—).

As used herein, the term "carbamate," refers to an O-carbamyl or N-carbamyl group as defined herein.

As used herein, the term "carbonyl," when alone includes formyl —C(═O)H and in combination is a —C(═O)— group.

As used herein, the term "carboxyl" or "carboxy" refers to —C(═O)OH or the corresponding "carboxylate" anion, such as is in a carboxylic acid salt. An "O-carboxy" group refers to a RC(═O)O— group, where R is as defined herein. A "C-carboxy" group refers to a —C(═O)OR groups where R is as defined herein.

As used herein, the term "cyano" refers to —CN.

As used herein, the term "carbocyclyl" refers to a saturated or partially saturated monocyclic or a fused bicyclic or tricyclic group wherein the ring atoms of the cyclic system are all carbon and wherein each cyclic moiety contains from 3 to 12 carbon atom ring members. "Carbocyclyl" encompasses benzo fused to a carbocyclyl ring system. One group of carbocyclyls have from 5 to 7 carbon atoms. Examples of carbocyclyl groups include, but are not limited to, cyclopropyl, cyclobutyl, cyclopentyl, cyclohexyl, and cycloheptyl, tetrahydronapthyl, indanyl, octahydronaphthyl, 2,3-dihydro-1H-indenyl, or adamantyl.

As used herein, the term "cycloalkyl" refers to a saturated monocyclic, bicyclic or tricyclic group wherein the ring atoms of the cyclic system are all carbon and wherein each cyclic moiety contains from 3 to 12 carbon atom ring members. One group of cycloalkyls has from 5 to 7 carbon atoms. Examples of cycloalkyl groups include, but are not limited to, cyclopropyl, cyclobutyl, cyclopentyl, cyclohexyl, cycloheptyl, or adamantyl.

As used herein, the term "cycloalkenyl" refers to a partially saturated monocyclic, bicyclic or tricyclic group wherein the ring atoms of the cyclic system are all carbon and wherein each cyclic moiety contains from 3 to 12 carbon atom ring members. One group of carboalkenyls have from 5 to 7 carbon atoms. Examples of cycloalkenyl groups include, but are not limited to, cyclobutenyl, cyclopentenyl, or cyclohexenyl.

As used herein, the term "cyclyl" refers to an aryl, heterocyclyl, or carbocyclyl group as defined herein. A "cyclyl" group may, for example, be an aryl group, a cycloalkyl group, a heteroaryl group or a heterocycloalkyl group.

As used herein, the term "halo" or "halogen" refers to fluorine, chlorine, bromine, or iodine.

As used herein, the term "haloalkoxy" refers to a haloalkyl group attached to the parent molecular moiety through an oxygen atom. Examples of haloalkoxy groups include, but are not limited to, trifluoromethoxy, 2-fluoroethoxy, or 3-chloropropoxy.

As used herein, the term "haloalkyl" refers to an alkyl group having the meaning as defined above wherein one or more hydrogens are replaced with a halogen. Specifically embraced are monohaloalkyl, dihaloalkyl or polyhaloalkyl groups. A monohaloalkyl group, for one example, may have an iodo, bromo, chloro or fluoro atom within the group. Dihalo or polyhaloalkyl groups may have two or more of the same halo atoms or a combination of different halo groups. Examples of haloalkyl groups include, but are not limited to, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl or dichloropropyl.

As used herein, the term "heteroalkyl" refers to a straight or branched alkyl chain, as defined herein above (e.g., an alkyl chain having from 1 to 6 carbon atoms), wherein one, two, or three carbons forming the alkyl chain are each replaced by a heteroatom independently selected from the group consisting of O, N, and S, and wherein the nitrogen and/or sulfur heteroatom(s) (if present) may optionally be oxidized and the nitrogen heteroatom(s) (if present) may optionally be quaternized. The heteroatom(s) O, N and S may, for example, be placed at an interior position of the heteroalkyl group, i.e., the heteroalkyl may be bound to the remainder of the molecule via a carbon atom. Up to two heteroatoms may be consecutive, such as, for example, —CH$_2$—NH—OCH$_3$.

As used herein, the term "heteroalkylene" refers to a heteroalkyl group attached at two positions. Examples include, but are not limited to, —CH$_2$OCH$_2$—, —CH$_2$SCH$_2$—, and —CH$_2$NHCH$_2$—, —CH$_2$S—, or —CH$_2$NHCH(CH$_3$)CH$_2$—.

As used herein, the term "heterocycloalkyl," refers to a heterocyclyl group that is not fully unsaturated e.g., one or more of the rings systems of a heterocycloalkyl is not aromatic. Examples of heterocycloalkyls include piperazinyl, morpholinyl, piperidinyl, or pyrrolidinyl.

As used herein, the term "hydroxyl," as used herein, refers to —OH.

As used herein, the term "hydroxyalkyl," as used herein, refers to a hydroxyl group attached to the parent molecular moiety through an alkyl group.

As used herein, the phrase "in the main chain," refers to the longest contiguous or adjacent chain of carbon atoms starting at the point of attachment of a group to the compounds of any one of the formulas disclosed herein.

As used herein, the term phrase "linear chain of atoms" refers to the longest straight chain of atoms independently selected from carbon, nitrogen, oxygen and sulfur.

As used herein, the term "lower," where not otherwise specifically defined, means containing from 1 to and including 6 carbon atoms.

As used herein, the term "lower aryl," means phenyl or naphthyl.

As used herein, the term "lower heteroaryl," means either 1) monocyclic heteroaryl comprising five or six ring members, of which between one and four said members may be heteroatoms selected from O, S, or N.

As used herein, the terms "benzo" and "benz," refer to the divalent group $C_6H_4$=derived from benzene. Examples include, but are not limited to, benzothiophene or benzimidazole.

As used herein, the term "nitro," refers to —$NO_2$.

As used herein, the terms "sulfonate" "sulfonic acid" and "sulfonic," refers to the —$SO_3H$ group and its anion as the sulfonic acid is used in salt formation.

As used herein, the term "sulfanyl," to —S—.

As used herein, the term "sulfinyl," refers to —S(═O)(R)—, with R as defined herein.

As used herein, the term "sulfonyl," refers to —$S(═O)_2$R, with R as defined herein.

As used herein, the term "sulfonamide" or "sulfonamido", refers to an N-sulfonamido or S-sulfonamido group as defined herein. As used herein, the term "N-sulfonamido," refers to a $RS(═O)_2N(R')$— group with R and R' as defined herein. Exemplary, non-limiting N-sulfonamido groups are —$NHSO_2$alkyl such as —$NHSO_2CH_3$, —$NHSO_2CH_2CH_3$ or —$NHSO_2$(isopropyl), and —$NHSO_2$ (optionally substituted aryl) such as —$NHSO_2$phenyl. As used herein, the term "S-sulfonamido," refers to a —$S(═O)_2NRR'$, group, with R and R' as defined herein.

As used herein, the term "urea," refers to a —N(R)C(═O)N(R) group wherein R and R' are as defined herein.

As used herein, "hydrogen bonding group" refers to a substituent group, which is capable of taking part in a non-covalent bonding between hydrogen and another atom (usually nitrogen or oxygen). Examples include, but are not limited to, —OH, $NH_2$, —OH, amido, —$S(O)_2NH_2$, —$C(═O)NH_2$, —$CH_2$—$C(═O)NH_2$, and —$CH_2$—$NH_2$.

As used herein, the term "optionally substituted" means the preceding or anteceding group may be substituted or unsubstituted. When substituted, the substituents of an "optionally substituted" group may include, without limitation, one or more substituents independently selected from the following groups or a particular designated set of groups, alone or in combination: lower alkyl, lower alkenyl, lower alkynyl, lower alkanoyl, lower heteroalkyl, lower heterocycloalkyl, lower haloalkyl, lower cycloalkyl, phenyl, aryl, aryloxy, lower alkoxy, lower haloalkoxy, oxo, lower acyloxy, carbonyl, carboxyl, lower alkylcarbonyl, lower carboxyester, lower carboxamido, cyano, hydrogen, halogen, hydroxyl, amino, lower alkylamino, arylamino, aminoalkyl, amido, nitro, thiol, lower alkylthio, lower haloalkylthio, lower perhaloalkylthio, arylthio, sulfonate, sulfonic acid, trisubstituted silyl, $N_3$, SH, $SCH_3$, $C(O)CH_3$, $CO_2CH_3$, $CO_2H$, pyridinyl, thiophene, furanyl, carbamate, and urea. Two substituents may be joined together to form a fused five-, six-, or seven-membered carbocyclic or heterocyclic ring consisting of zero to three heteroatoms, for example forming methylenedioxy or ethylenedioxy. An optionally substituted group may be unsubstituted (e.g., —$CH_2CH_3$), fully substituted (e.g., —$CF_2CF_3$), monosubstituted (e.g., —$CH_2CH_2F$) or substituted at a level anywhere in-between fully substituted and monosubstituted (e.g., —$CH_2CF_3$). Where substituents are recited without qualification as to substitution, both substituted and unsubstituted forms are encompassed. Where a substituent is qualified as "substituted," the substituted form is specifically intended. Additionally, different sets of optional substituents to a particular moiety may be defined as needed; in these cases, the optional substitution will be as defined, often immediately following the phrase, "optionally substituted with." In one specific definition, the optional substituents are chosen from hydroxyl, halo, alkyl, alkoxy, haloalkyl, haloalkoxy, —N((C1-C3)alkyl)$_2$, —NH((C1-C3)alkyl), —NHC(═O)((C1-C3)alkyl), —C(═O)OH, —C(═O)O((C1-C3)alkyl), —C(═O)(C1-C3)alkyl), —C(═O)NH$_2$, —C(═O)NH(C1-C3)alkyl), —C(═O)NH(cycloalkyl), —C(═O)N(C1-C3) alkyl)$_2$, —S(═O)$_2$((C1-C3)alkyl), —S(═O)$_2$NH$_2$, —S(═O)$_2$N((C1-C3)alkyl)$_2$, —S(═O)$_2$NH((C1-C3)alkyl), —CHF$_2$, —OCF$_3$, —OCHF$_2$, —SCF$_3$, —CF$_3$, —CN, —NH$_2$, —NO$_2$, or tetrazolyl.

The term R or the term R', appearing by itself and without a number designation, unless otherwise defined, refers to a moiety selected from the group consisting of hydrogen, alkyl, cycloalkyl, heteroalkyl, aryl, heteroaryl and heterocycloalkyl. Whether an R group has a number designation or not, every R group, including R, R' and $R^p$ where p=(1, 2, 3, . . . p), every substituent, and every term should be understood to be independent of every other in terms of selection from a group. Should any variable, substituent, or term (e.g., aryl, heterocycle, R, etc.) occur more than one time in a formula or generic structure, its definition at each occurrence is independent of the definition at every other occurrence. Those of skill in the art will further recognize that certain groups may be attached to a parent molecule or may occupy a position in a chain of elements from either end as written. Thus, by way of example only, an unsymmetrical group such as —C(═O)N(R)— may be attached to the parent moiety at either the carbon or the nitrogen.

As used herein, the term "2-cyclylcyclopropan-1-amine compound" refers to a compound comprising a 2-cyclylcyclopropan-1-amine moiety or a pharmaceutically acceptable salt or solvate thereof. Exemplary 2-cyclylcyclopropan-1-amine compounds are, without limitation, 2-arylcyclopropan-1-amine compounds (such as 2-phenylcyclopropan-1-amine compounds) and 2-heteroarylcyclopropan-1-amine compounds (such as 2-pyridinylcyclopropan-1-amine compounds or 2-thiazolylcyclopropan-1-amine compounds).

As used herein, the term "2-arylcyclopropan-1-amine compound" refers to a compound comprising a 2-arylcyclopropan-1-amine moiety or a pharmaceutically acceptable salt or solvate thereof.

As used herein, the term "2-heteroarylcyclopropan-1-amine compound" refers to a compound comprising a 2-heteroarylcyclopropan-1-amine moiety or a pharmaceutically acceptable salt or solvate thereof.

As used herein, the term "2-phenylcyclopropan-1-amine compound" refers to a compound comprising a 2-phenylcyclopropan-1-amine moiety or a pharmaceutically acceptable salt or solvate thereof.

As used herein, the term "2-pyridinylcyclopropan-1-amine compound" refers to a compound comprising a 2-pyridinylcyclopropan-1-amine moiety or a pharmaceutically acceptable salt or solvate thereof.

As used herein, the term "2-thiazolylcyclopropan-1-amine compound" refers to a compound comprising a 2-thiazolylcyclopropan-1-amine moiety or a pharmaceutically acceptable salt or solvate thereof.

As used herein, the term "phenelzine compound" refers to a compound comprising a 2-phenylethylhydrazine moiety or a pharmaceutically acceptable salt or solvate thereof.

As used herein, the term "propargylamine compound" refers to a compound comprising a propargylamine moiety or a pharmaceutically acceptable salt or solvate thereof. An exemplary propargylamine compound is, without limitation, pargyline (N-benzyl-N-methylprop-2-yn-1-amine).

In reference to the substituents referred to above, as the skilled artisan is aware, the appropriate selection of the substituents can be made in view of the disclosure herein to provide LSD1 inhibitors, selective LSD1 inhibitors, and dual LSD1/MAOB inhibitors for use in the methods and compositions of the invention.

Other LSD1 inhibitors include, but are not limited to those e.g., disclosed in Ueda et al. ((2009) *J. Am. Chem Soc.* 131(48):17536-17537) including; Binda et al. (*J Am Chem Soc.* 2010 May 19; 132(19):6827-33). Mimasu et al. ((2010) Biochemistry June 22. [Epub ahead of print]PMID: 20568732 [PubMed—as supplied by publisher].

Other phenylcyclopropylamine derivatives and analogs are found e.g., in Kaiser et al. ((1962) *J. Med. Chem.* 5:1243-1265); Zirkle et al. ((1962) *J. Med. Chem.* 1265-1284; U.S. Pat. Nos. 3,365,458; 3,471,522; 3,532,749) and Bolesov et al. ((1974) *Zhurnal Organicheskoi Khimii* 10:8 1661-1669) and Russian Patent No. 230169 (19681030).

Preferably, the LSD1 inhibitor for use in the invention is a selective LSD1 inhibitor or dual inhibitor of LSD1 and MAOB. In one preferred aspect, the selective LSD1 or dual LSD1 MAOB inhibitor has a molecular weight of less than 700. In one preferred aspect, the selective LSD1 or dual LSD1 MAOB inhibitor has a molecular weight of less than 500. In one preferred aspect, the selective LSD1 or dual LSD1 MAOB inhibitor has a molecular weight of less than 300.

Preferably, the LSD1 inhibitor comprises five or less amide bonds (—NH—C=O). Preferably, the LSD1 inhibitor comprises three or less amide bonds (—NH—C=O).

In one aspect, the LSD1 inhibitor for use in the invention has zero amide bonds.

In one aspect, the selective LSD1 and dual LSD1/MAOB inhibitors for use in the invention desirably inhibits LSD1 and/or MAOB selectively compared to MAOA, thus avoiding deleterious side effects associated with administration to animals, including humans, of MAOA inhibitors. As the inventors have described herein, the selective LSD1 inhibitors and the dual LSD1/MAOB inhibitors can be administered in a such a way to an individual e.g., a mammal or human, to achieve concentration in vivo that are expected to inhibit LSD1 and/or MAO-B while avoiding the toxicity associated with inhibition of MAOA and these concentrations are sufficient enough to improve specific phenotypes or symptoms associated with Flaviviridae infection or HCV infection.

In another aspect, the selective LSD1 and dual LSD11/MAOB inhibitors for use in the invention desirably inhibit LSD1 and/or MAOB targeting a host cell protein involved in Flaviviridae infection. Without wishing to be bound by theory targeting Flaviviridae with LSD1 inhibitors can avoid or lessen the ability of the virus to develop resistance to therapy alone or in combination with an interferon agent or an agent targeting a viral protein such as a protease inhibitor or a nucleoside or non-nucleoside polymerase inhibitor or an NS5A inhibitor. As the inventors have described herein, the selective LSD1 inhibitors and the dual LSD1/MAOB inhibitors can be administered in a such a way to an individual e.g., a mammal or human, to achieve concentration in vivo that are expected to inhibit LSD1 and/or MAO-B while avoiding the toxicity associated with inhibition of MAOA and these concentrations are sufficient enough to improve specific phenotypes or symptoms associated with Flaviviridae or HCV infection.

In one aspect, the selective LSD1 and dual LSD1/MAOB inhibitors for use in the invention desirably inhibit LSD1 and/or MAOB targeting a host cell protein involved in Flaviviridae infection. Without wishing to be bound by theory targeting Flaviviridae with LSD1 inhibitors can avoid or lessen the side effects associated with treatment with interferon agent or an agent targeting a viral protein such as a protease inhibitor or a nucleoside or non-nucleoside polymerase inhibitor or an NS5A inhibitor. As the inventors have described herein, the selective LSD1 inhibitors and the dual LSD1/MAOB inhibitors can be administered in a such a way to an individual e.g., a mammal or human, to achieve concentration in vivo that are expected to inhibit LSD1 and/or MAO-B while avoiding the toxicity associated with inhibition of MAOA and these concentrations are sufficient enough to improve specific phenotypes or symptoms associated with Flaviviridae or HCV infection.

In still another aspect, the selective LSD1 and dual LSD1/MAOB inhibitors for use in the invention desirably inhibit LSD1 and/or MAOB targeting a host cell protein involved in HCV infection. Without wishing to be bound by theory targeting HCV with LSD1 inhibitors can avoid or lessen the side effects associated with treatment with interferon agent or an agent targeting a viral protein such as a protease inhibitor or a nucleoside or non-nucleoside polymerase inhibitor or an NS5A inhibitor. As the inventors have described herein, the selective LSD1 inhibitors and the dual LSD1/MAOB inhibitors can be administered in a such a way to an individual e.g., a mammal or human, to achieve concentration in vivo that are expected to inhibit LSD1 and/or MAO-B while avoiding the toxicity associated with inhibition of MAOA and these concentrations are sufficient enough to improve specific phenotypes or symptoms associated with HCV infection.

The invention provides a pharmaceutical composition comprising a pharmaceutically acceptable carrier and a compound which is a selective inhibitor of LSD1. Preferably, LSD1 selective inhibitors have IC50 values for LSD1 which are at least 2-fold lower than the IC50 value for MAOA and/or MAOB. Even more preferably, LSD1 selective inhibitors have IC50 values for LSD1 which are at least 5-fold lower than the IC50 value for MAOA and/or MAOB. Yet even more preferably, LSD1 selective inhibitors have IC50 values for LSD1 which are at least 10-fold lower than the IC50 value for MAOA and/or MAOB. The ability of a compound to inhibit LSD1 and its IC50 values for LSD1, MAO-A and MAO-B can be determined in accordance with the experimental protocol described in Example 1. In one specific embodiment, dual selective LSD1/selective inhibitor for use in the invention are as defined above and is chosen from a phenylcyclopropylamine derivative or analog, a phenelzine derivative or analog, or a propargylamine derivative or analog. In another embodiment, the selective LSD1 inhibitor for use in the invention is chosen from a 2-cyclylcyclopropan-1-amine compound, a phenelzine compound and a propargylamine compound; more preferably, the LSD1 inhibitor for use in the invention is a 2-cyclylcyclopropan-1-amine compound, preferably a 2-arylcyclopropan-1-amine compound or a 2-heteroarylcyclopropan-1-amine compound, and still more preferably a 2-phenylcyclopropan-1-amine compound, 2-pyridinylcyclopropan-1-amine compound or a 2-thiazolylcyclopropan-1-amine compound.

The invention also provides a pharmaceutical composition comprising a pharmaceutically acceptable carrier and a compound which is a dual inhibitor selective for LSD1 and MAOB. Preferably, dual LSD1/MAOB selective inhibitors have IC50 values for LSD1 and MAOB which are at least 2-fold lower than the IC50 value for MAO-A. Even more preferably, dual LSD1/MAOB selective inhibitors have IC50 values for LSD1 and MAOB which are at least 5-fold lower than the IC50 value for MAO-A. Yet even more preferably, dual LSD1/MAOB selective inhibitors have C150 values for LSD1 and MAOB which are at least 10-fold lower than the IC50 value for MAO-A. The ability of a compound to inhibit LSD1 and MAO-B and its IC50 values for LSD1, MAO-A and MAO-B can be determined in accordance with the experimental protocol described in Example 1 In one specific embodiment, dual selective LSD1/selective inhibitors for use in the invention are as defined above and are chosen from a phenylcyclopropylamine derivative or analog, a phenelzine derivative or analog, or a propargylamine derivative or analog. In another embodiment, the dual LSD1/MAOB inhibitor for use in the invention is chosen from a 2-cyclylcyclopropan-1-amine compound, a phenelzine compound and a propargylamine compound; more preferably, the dual LSD1/MAOB inhibitor for use in the invention is a 2-cyclylcyclopropan-1-amine compound, preferably a 2-arylcyclopropan-1-amine compound or a 2-heteroarylcyclopropan-1-amine compound, and still more preferably a 2-phenylcyclopropan-1-amine compound, 2-pyridinylcyclopropan-1-amine compound or a 2-thiazolylcyclopropan-1-amine compound.

Typically, compounds for use as selective LSD1 inhibitors or dual inhibitors of LSD1 and MAOB can be effective in an amount of from about 0.01 µg/kg to about 100 mg/kg per day based on total body weight. The active ingredient may be administered at once, or may be divided into a number of smaller doses to be administered at predetermined intervals of time. The suitable dosage unit for humans for each administration can be, e.g., from about 1 µg to about 2000 mg, preferably from about 5 µg to about 1000 mg, and even more preferably from about 0.5 mg to about 500 mg. The active ingredient can be administered orally or by other routes of administration e.g., IP, IV, etc. Preferably, the inhibitor is formulated and delivered in such a way as to achieve concentration in vivo that modulate the target activity e.g., LSD1 and/or MAOB. Thus, in a specific embodiment, the effective amount of compound ranges from 0.05 µg/kg to about 100 mg/kg per day based on total body weight, preferably from 0.05 µg/kg to about 50 mg/kg.

It should be understood that the dosage ranges set forth above are exemplary only and are not intended to limit the scope of this invention unless specified. The therapeutically effective amount for each active compound can vary with factors including but not limited to the activity of the compound used, stability of the active compound in the patient's body, the severity of the conditions to be alleviated, the total weight of the patient treated, the route of administration, the ease of absorption, distribution, and excretion of the active compound by the body, the age and sensitivity of the patient to be treated, and the like, as will be apparent to a skilled artisan. The amount of administration can be adjusted as the various factors change over time.

For oral delivery, the active compounds can be incorporated into a formulation that includes pharmaceutically acceptable carriers such as binders (e.g., gelatin, cellulose, gum tragacanth), excipients (e.g., starch, lactose), lubricants (e.g., magnesium stearate, silicon dioxide), disintegrating agents (e.g., alginate, Primogel, and corn starch), and sweetening or flavoring agents (e.g., glucose, sucrose, saccharin, methyl salicylate, and peppermint). The formulation can be orally delivered in the form of enclosed gelatin capsules or compressed tablets. Capsules and tablets can be prepared in any conventional techniques. The capsules and tablets can also be coated with various coatings known in the art to modify the flavors, tastes, colors, and shapes of the capsules and tablets. In addition, liquid carriers such as fatty oil can also be included in capsules.

Suitable oral formulations can also be in the form of suspension, syrup, chewing gum, wafer, elixir, and the like. If desired, conventional agents for modifying flavors, tastes, colors, and shapes of the special forms can also be included. In addition, for convenient administration by enteral feeding tube in patients unable to swallow, the active compounds can be dissolved in an acceptable lipophilic vegetable oil vehicle such as olive oil, corn oil and safflower oil.

The active compounds can also be administered parenterally in the form of solution or suspension, or in lyophilized form capable of conversion into a solution or suspension form before use. In such formulations, diluents or pharmaceutically acceptable carriers such as sterile water and physiological saline buffer can be used. Other conventional solvents, pH buffers, stabilizers, anti-bacteria agents, surfactants, and antioxidants can all be included. For example, useful components include sodium chloride, acetates, citrates or phosphates buffers, glycerin, dextrose, fixed oils, methyl parabens, polyethylene glycol, propylene glycol, sodium bisulfate, benzyl alcohol, ascorbic acid, and the like. The parenteral formulations can be stored in any conventional containers such as vials and ampoules.

Routes of topical administration include nasal, bucal, mucosal, rectal, or vaginal applications. For topical administration, the active compounds can be formulated into lotions, creams, ointments, gels, powders, pastes, sprays, suspensions, drops and aerosols. Thus, one or more thickening agents, humectants, and stabilizing agents can be included in the formulations. Examples of such agents include, but are not limited to, polyethylene glycol, sorbitol, xanthan gum, petrolatum, beeswax, or mineral oil, lanolin, squalene, and the like. A special form of topical administration is delivery by a transdermal patch. Methods for preparing transdermal patches are disclosed, e.g., in Brown, et al. (1988) Ann. Rev. Med. 39:221-229 which is incorporated herein by reference.

Subcutaneous implantation for sustained release of the active compounds may also be a suitable route of administration. This entails surgical procedures for implanting an active compound in any suitable formulation into a subcutaneous space, e.g., beneath the anterior abdominal wall. See, e.g., Wilson et al. (1984) J. Clin. Psych. 45:242-247. Hydrogels can be used as a carrier for the sustained release of the active compounds. Hydrogels are generally known in the art. They are typically made by crosslinking high molecular weight biocompatible polymers into a network, which swells in water to form a gel like material. Preferably, hydrogels are biodegradable or biosorbable. For purposes of this invention, hydrogels made of polyethylene glycols, collagen, or poly(glycolic-co-L-lactic acid) may be useful. See, e.g., Phillips et al. (1984) J. Pharmaceut. Sci., 73: 1718-1720.

The active compounds can also be conjugated, to a water soluble non-immunogenic non-peptidic high molecular weight polymer to form a polymer conjugate. For example, an active compound is covalently linked to polyethylene glycol to form a conjugate. Typically, such a conjugate exhibits improved solubility, stability, and reduced toxicity and immunogenicity. Thus, when administered to a patient, the active compound in the conjugate can have a longer half-life in the body, and exhibit better efficacy. See generally, Burnham (1994) Am. J. Hosp. Pharm. 15:210-218. PEGylated proteins are currently being used in protein replacement therapies and for other therapeutic uses.

For example, PEGylated interferon (PEG-INTRON A®) is clinically used for treating Hepatitis B. PEGylated adenosine deaminase (ADAGEN®) is being used to treat severe combined immunodeficiency disease (SCIDS). PEGylated L-asparaginase (ONCAPSPAR®) is being used to treat acute lymphoblastic leukemia (ALL). It is preferred that the covalent linkage between the polymer and the active compound and/or the polymer itself is hydrolytically degradable under physiological conditions. Such conjugates known as "prodrugs" can readily release the active compound inside the body. Controlled release of an active compound can also be achieved by incorporating the active ingredient into microcapsules, nanocapsules, or hydrogels generally known in the art. Other pharmaceutically acceptable prodrugs of the compounds of this invention include, but are not limited to, esters, carbonates, thiocarbonates, N-acyl derivatives, N-acyloxyalkyl derivatives, quaternary derivatives of tertiary amines, N-Mannich bases, Schiff bases, aminoacid conjugates, phosphate esters, metal salts and sulfonate esters.

Liposomes can also be used as carriers for the active compounds of the present invention. Liposomes are micelles made of various lipids such as cholesterol, phospholipids, fatty acids, and derivatives thereof. Various modified lipids can also be used. Liposomes can reduce the toxicity of the active compounds, and increase their stability. Methods for preparing liposomal suspensions containing active ingredients therein are generally known in the art. See, e.g., U.S. Pat. No. 4,522,811; Prescott, Ed., Methods in Cell Biology, Volume XIV, Academic Press, New York, N.Y. (1976).

The active ingredient can be formulated as a pharmaceutically acceptable salt. A "pharmaceutically acceptable salt" is intended to mean a salt that retains the biological effectiveness of the free acids and bases of the specified compound and that is not biologically or otherwise undesirable. A compound for use in the invention may possess a sufficiently acidic, a sufficiently basic, or both functional groups, and accordingly react with any of a number of inorganic or organic bases, and inorganic and organic acids, to form a pharmaceutically acceptable salt. Exemplary pharmaceutically acceptable salts include those salts prepared by reaction of the compounds of the present invention with a mineral or organic acid or an inorganic base, such as salts including sulfates, pyrosulfates, bisulfates, sulfites, bisulfites, phosphates, monohydrophosphates, dihydrophosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4 dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, gamma-hydroxybutyrates, glycollates, tartrates, methane-sulfonates, propanesulfonates, naphthalene-1-sulfonates, naphthalene-2-sulfonates, or mandelates.

As used herein, a "pharmaceutically acceptable carrier" refers to a non-API (API refers to Active Pharmaceutical Ingredient) substances such as disintegrators, binders, fillers, and lubricants used in formulating pharmaceutical products. They are generally safe for administering to humans according to established governmental standards, including those promulgated by the United States Food and Drug Administration and the European Medical Agency.

The active compounds can also be administered in combination with another active agent that synergistically treats or prevents the same symptoms or is effective for another disease or symptom in the patient treated so long as the other active agent does not interfere with or adversely affect the effects of the active compounds of this invention. Such other active agents include but are not limited to anti-inflammation agents, antiviral agents, antibiotics, antifungal agents, antithrombotic agents, cardiovascular drugs, cholesterol lowering agents, anti-cancer drugs, hypertension drugs, and the like.

As used herein the term "hepatitis C" or "HCV" refers to any of the strains and isolates of hepatitis C that have been identified or are identifiable according to known classifications and methods. The term "hepatitis C" or "HCV" is intended to encompass all currently known strains, types and subtypes of HCV as wells those discovered and classified as HCV in the future. The identification of HCV is well within the purvey of an ordinary skilled artisan. The first known HCV isolate was identified in the USA (see Q.-L. Choo et al. (1989) Science 244: 359-362, Q.-L. Choo et al. (1990) Brit. Med. Bull. 46: 423-441, Q.-L. Choo et al., Proc. Natl. Acad. Sci. 88: 2451-2455 (1991). Numerous HCV strains, types, and subtypes are known with their sequences being deposited in public databases. Examples include, but are not limited to, GenBank accession numbers AF177036, AF169002, D28917, AF169003, D84262, AF238484, Y12083, AB047639, AB047641, D63821, and the such.

As used herein, the term "interferon agent" or "alpha interferon" or "interferon alpha" or "a-interferon" refers to the family of interferon proteins that inhibit viral replication, inhibit cellular proliferation, and modulate immune response. The term "alpha interferon" encompasses a variety of commercially available alpha interferons, including, but not limited to, Roferon A interferon (Hoffman-La Roche, Nutley, N.J.), Berofor alpha 2 (Boehringer Ingelheim Pharmaceutical, Inc., Ridgefield, Conn.), Sumiferon (Sumitomo, Japan), Wellferon interferon alpha-n1 (Glaxo-Wellcome Ltd., London, Great Britain). Alpha interferon 2b currently has the broadest approval throughout the world for use in treating HCV. U.S. Pat. No. 4,530,901 (which is hereby incorporated by reference in its entirety) provides a description of the manufacture of alpha interferon 2b.

As used herein, the term "diagnosed with HCV" refers to an individual in which a HCV marker has been detected. A variety of HCV markers are known in the art and can be readily measured by a skilled artisan. For example, HCV can be detected by testing for antibodies against HCV (anti-HCV) in a patient or suspected carrier's blood serum.

Another approach to detecting HCV is to test for HCV RNA in the serum of a patient or suspected carrier using a PCR based assay. Recombinant immunoblots can also be used to detect HCV. In this test serum is incubated with four recombinant viral proteins that are blotted on nitrocellulose strips. A simple color change indicates antibodies are present in the serum that bind to the viral proteins. Furthermore, new methods for detecting HCV are continually being developed and the methods can be employed for diagnosing HCV infection.

As used herein, the term "side effects of alpha interferon treatment" include fatigue, muscle aches, headaches, nausea, vomiting, low-grade fever, weight loss, irritability, depression, mild bone marrow suppression, and hair loss.

As used herein, the term "side effects associated with ribavirin treatment" refers to anemia, fatigue and irritability, itching, skin rash, nasal congestion, sinusitis, and cough associated with the administration of ribavirin to an individual.

As used herein, the term "alleviate a symptom associated with HCV" refers to a lessening of fatigue, dark urine, abdominal pain, nausea, tenderness in the upper right quadrant, poor appetite, muscle and joint pain, cirrhosis (with symptoms such as enlarged liver, enlarged spleen, jaundice, muscle wasting excoriations, ascites and ankle swelling).

The term also encompasses symptoms not associated with the liver, including, but not limited to, cryoglobulinemia symptoms such as skin rashes, joint and muscle aches, kidney disease, neuropathy, cryoglobulins, rheumatoid factor, low complement levels in serum, glomerulonephritis, or porphyria cutanca tarda. The term is also meant to encompass the alleviation of symptoms associated with disease that are thought to be or might be associated with chronic HCV including seronegative arthritis, keratoconjunctivitis sicca (Sjogren's syndrome), non-Hodgkin's type B-cell lymphomas, fibromyalgia, or lichen planus.

As used herein, the term "individual in need of treatment" encompasses individuals who have symptoms of Flaviviridae infection, such as HCV infection, those who have been diagnosed with Flaviviridae infection or disease caused by Flaviviridae, such as those diagnosed with HCV, or those in need of prophylaxis. An "individual in need of treatment" can have anti-HCV, HCV RNA, elevated serum aminotransferase levels, and/or evidence of chronic hepatitis.

As used herein, the term "ribavirin" refers to 1-D-ribofuranosyl-1H-1,2,4-triazole-3-carboxamide.

As used herein, the term "reversible amine oxidase" inhibitor refers to the class of compounds that inhibit MAOA or MAOB in a reversible manner that are well known in the art. Reversible amine oxidase inhibitors can be designed to increase selectivity for LSD1 using medicinal chemistry approaches.

As used herein, the term "irreversible amine oxidase" inhibitor refers to the class of compounds that inhibit MAOA or MAOB in an irreversible manner that are well known in the art. Examples of irreversible MAO inhibitors include phenylcyclopropylamine, phenelzine, and pargyline. Irreversible amine oxidase inhibitors can be designed to increase selectivity for LSD1 using medicinal chemistry approaches.

In reference to the other anti-HCV agents referred to herein, terms such as VX950, R7227, Telaprevir are intended to encompass the active agent as well as any salt forms of the active agent, and the particular salt form of the active agent that is in development or marketed unless otherwise specified.

There examples described herein are intended to illustrate different aspects of the invention by exemplification and are not intended to limit the scope of the claims or invention.

EXAMPLES

Example 1

Biochemical Assays

Compounds for use in the methods of the invention can be identified by their ability to inhibit LSD1. The ability of the compounds of the invention to inhibit LSD1 can be tested as follows. Human recombinant LSD1 protein was purchased from BPS Bioscience Inc. In order to monitor LSD1 enzymatic activity and/or its inhibition rate by our inhibitor(s) of interest, di-methylated H3-K4 peptide (Millipore) was chosen as a substrate. The demethylase activity was estimated, under aerobic conditions, by measuring the release of $H_2O_2$ produced during the catalytic process, using the Amplex® Red peroxide/peroxidase-coupled assay kit (Invitrogen).

Briefly, a fixed amount of LSD1 was incubated on ice for 15 minutes, in the absence and/or in the presence of various concentrations of inhibitor (e.g., from 0 to 75 µM, depending on the inhibitor strength). Tranylcypromine (Biomol International) was used as a control for inhibition. Within the experiment, each concentration of inhibitor was tested in triplicate. After leaving the enzyme interacting with the inhibitor, 12.5 µM of di-methylated H3-K4 peptide was added to each reaction and the experiment was left for 1 hour at 37° C. in the dark. The enzymatic reactions were set up in a 50 mM sodium phosphate, pH 7.4 buffer. At the end of the incubation, Amplex® Red reagent and horseradish peroxidase (HPR) solution were added to the reaction according to the recommendations provided by the supplier (Invitrogen), and left to incubate for 30 extra minutes at room temperature in the dark. A 1 µM $H_2O_2$ solution was used as a control of the kit efficiency. The conversion of the Amplex® Red reagent to resorufin due to the presence of $H_2O_2$ in the assay, was monitored by fluorescence (excitation at 540 nm, emission at 590 nm) using a microplate reader (Infinite 200, Tecan). Arbitrary units were used to measure level of $H_2O_2$ produced in the absence and/or in the presence of inhibitor.

The maximum demethylase activity of LSD1 was obtained in the absence of inhibitor and corrected for background fluorescence in the absence of LSD1. The Ki (IC50) of each inhibitor was estimated at half of the maximum activity.

Human recombinant monoamine oxidase proteins MAO-A and MAO-B were purchased from Sigma Aldrich. MAOs catalyze the oxidative deamination of primary, secondary and tertiary amines. In order to monitor MAO enzymatic activities and/or their inhibition rate by inhibitor(s) of interest, a fluorescent-based (inhibitor)-screening assay was set up. 3-(2-Aminophenyl)-3-oxopropanamine (kynuramine dihydrobromide, Sigma Aldrich), a non fluorescent compound was chosen as a substrate. Kynuramine is a non-specific substrate for both MAOs activities. While undergoing oxidative deamination by MAO activities, kynuramine is converted into 4-hydroxyquinoline (4-HQ), a resulting fluorescent product.

The monoamine oxidase activity was estimated by measuring the conversion of kynuramine into 4-hydroxyquinoline. Assays were conducted in 96-well black plates with clear bottom (Corning) in a final Volume of 100 µL. The assay buffer was 100 mM HEPES, pH 7.5. Each experiment was performed in triplicate within the same experiment.

Briefly, a fixed amount of MAO (0.25 μg for MAO-A and 0.5 μg for MAO-B) was incubated on ice for 15 minutes in the reaction buffer, in the absence and/or in the presence of various concentrations of inhibitor (e.g., from 0 to 50 μM, depending on the inhibitor strength). Tranylcypromine (Biomol International) was used as a control for inhibition.

After leaving the enzyme(s) interacting with the inhibitor, 60 to 90 μM of kynuramine was added to each reaction for MAO-B and MAO-A assay respectively, and the reaction was left for 1 hour at 37° C. in the dark. The oxidative deamination of the substrate was stopped by adding 50 μL (v/v) of NaOH 2N. The conversion of kynuramine to 4-hydroxyquinoline, was monitored by fluorescence (excitation at 320 nm, emission at 360 nm) using a microplate reader (Infinite 200, Tecan). Arbitrary units were used to measure levels of fluorescence produced in the absence and/or in the presence of inhibitor.

The maximum of oxidative deamination activity was obtained by measuring the amount of 4-hydroxyquinoline formed from kynuramine deamination in the absence of inhibitor and corrected for background fluorescence in the absence of MAO enzymes. The Ki (IC50) of each inhibitor was determined at Vmax/2.

Example 2

LSD1 and LSD1/MAOB Dual Inhibitors

| Compound No. | LSD1 IC50 (uM) | MAOA IC50 (uM) | MAO B IC50 (uM) |
| --- | --- | --- | --- |
| Dual-1 | <0.20 | >1.0 | <0.20 |
| Dual-2 | <0.20 | >40 | <0.30 |
| Selective-1 | <0.10 | >1.0 | >1.0 |
| Selective-2 | <0.10 | >1.0 | >1.0 | uM = μM

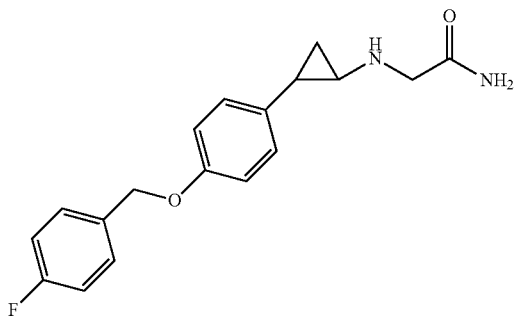

Dual-2 (i.e., "OG Compound F")

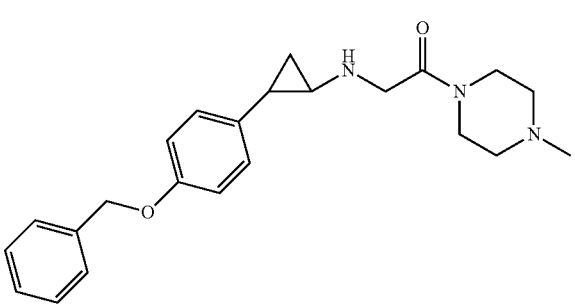

Selective-1 (i.e., "OG Compound A")

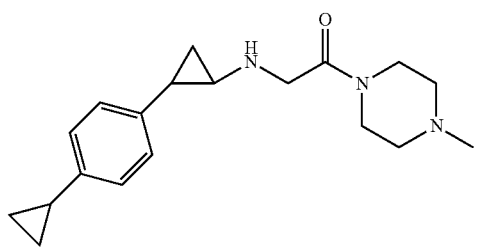

Selective-2 (i.e., "OG Compound C")

Other specific examples of LSD1 inhibitors include Compound X

Dual-1 (i.e., "OG Compound E")

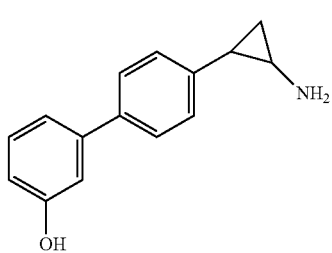 [SMILES: NC1CC1c1ccc(-c2cccc(O)c2)cc1]

Compound Y

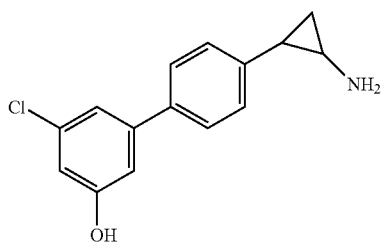 [SMILES: NC1CC1c1ccc(-c2cc(O)cc(Cl)c2)cc1]

which are both selective LSD1 inhibitors
and Compound Z

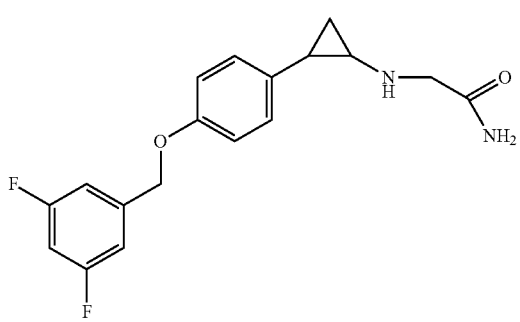 [SMILES: NC(=O)CNC1CC1c1ccc(OCc2cc(F)cc(F)c2)cc1]

which is a dual LSD1/MAOB inhibitor.

Example 3

LSD1 and LSD1/MAO-B Dual Inhibitors Increase Histone Lysine Methylation in Cell Based Assays Histone from SH-SY5Y cells grown in the presence of Compound Dual-1 (a dual LSD1/MAOB inhibitor) or tranylcypromine (parnate) for 1, 2, and 3 days were extracted and subjected to western blot analysis using a commercially available antibody specific for dimethylated H—K4. B-actin was used as a loading control.

The results of a western blot stained for H3K4 methylation with SH-SY5Y cells grown in the presence of Compound Dual-1 or tranylcypromine (parnate) for 1, 2, and 3 days, show that this compound, Dual-1, increases H3K4 methylation in cells in a time dependent manner and furthermore Compound Dual-1 appears to be 10-fold or more potent at increasing global dimethylated H3K4 levels as compared to tranylcypromine.

Furthermore, the inventors have conducted similar studies for other dual inhibitors of LSD1/MAOB and with selective LSD1 inhibitors and found that these compounds can increase dimethylated H3K4 levels in similarly performed assays.

Example 4

LSD1 Inhibitors can be Administered Safely to Mammals

Maximum tolerated dose studies and pharmacokinetics for several LSD1 inhibitors were assessed to determine if the compounds can be administered to mammals safely at doses that are expected to achieve therapeutic effects. In particular, Compound X was given to mice IP at 20 mg/kg, 40 mg/kg and 60 mg/kg daily for 5 days in a MTD study conducted at Leitat. The results of these studies showed that these doses were tolerated with acceptable toxicity. Furthermore, PK studies showed that such doses achieved Cmax values that are expected to result in therapeutic levels of LSD1 inhibitor in mammals.

Example 5

LSD1 Inhibitors Inhibit HCV RNA Replication

Anti-HCV assays were conducted at Southern Research Organization using an HCV RNA replicon with a luciferase reporter.

Southern Research reports that they use cell line Huh7 ET (luc-ubi-neo/ET) containing a HCV RNA replicon with a luciferase (LUC) reporter. This particular construct has not been described in the scientific literature although it is similar to the cell line 5-2 (Krieger et al. (2001) J. Virol. 75:4614-462.) and contains additional modifications that make the cell line more robust and provides for stable LUC expression for antiviral screening. This composition of the replicon is shown as follows 5'-Luc-Ubiq-Neo - - - NS3-NS4A-NS4B-NS5A-NS5B-3'

The HCV RNA replicon ET contains the 5' NTR (IRES) of HCV (5') which drives the production of a firefly luciferase (Luc), ubiquitin (Ubiq), and neomycin phosphotransferase (Neo) fusion protein. Ubiquitin cleavage releases the LUC and Neo genes. The EMCV IRES element (E-I) controls the translation of the HCV structural proteins NS3-NS5 and is located between Neo and NS3. The NS3 protein cleaves the HCV polyprotein to release the mature NS3, NS4A, NS4B, NS5A and NS5B proteins that are required for HCV replication. At the 3' end of the replicon is the authentic 3' NTR of HCV. The LUC reporter is used as an indirect measure of HCV replication. The activity of the LUC reporter is directly proportional to HCV RNA levels and positive control antiviral compounds behave comparably using either LUC or RNA endpoints.

RNA Replicon Assay

The effect of drug added in triplicate at concentrations of from e.g., 0 to 100 uM using half log dilutions on HCV RNA-derived LUC activity and cytotoxicity. Human interferon alpha-2b is included in each run as a positive control compound. Subconfluent cultures of the ET line are plated out into 96-well plates that are dedicated for the analysis of cell numbers (cytotoxicity) or antiviral activity and the next day drugs are added to the appropriate wells. Cells are processed 72 hr later when the cells are still subconfluent. Results from these assays are reported in Table 1 below. Compound cytotoxicity is assessed as the percent viable cells relative to the untreated cell controls. This data is also reported. As is seen below Compound X has strong anti-HCV activity in the 300-500 nanomolar range with a selectivity index (therapeutic index) in the range of 110-160.

TABLE 1

Activity of LSD1 inhibitor in an anti-HCV assay

| Compound | High Test Concentration | Antiviral Activity $EC_{50}$ | Cytotoxicity $IC_{50}$ | Selectivity Index SI |
|---|---|---|---|---|
| Compound X | 100 uM | 0.49 uM | 54.81 uM | 112 |
| rIFNα-2b | 2 IU/mL | 0.02 IU/mL | >2 IU/mL | >100 |

TABLE 1-continued

Activity of LSD1 inhibitor in an anti-HCV assay

| Compound | High Test Concentration | Antiviral Activity $EC_{50}$ | Cytotoxicity $IC_{50}$ | Selectivity Index SI |
|---|---|---|---|---|
| Compound X | 100 uM | <0.32 uM | 50.55 uM | 158 |
| rIFNα-2b | 2 IU/mL | 0.02 IU/mL | >2 IU/mL | >100 | uM = μM

The invention claimed is:

1. A method of treating a Flaviviridae infection or a disease or disorder associated with Flaviviridae, the method comprising administering to an individual in need of such treatment a Lysine Specific Demethylase-1 (LSD1) inhibitor, wherein said LSD1 inhibitor is a 2-cyclylcyclopropan-1-amine compound of formula (I) or an enantiomer, a diastereomer, or a racemic mixture thereof, or a pharmaceutically acceptable salt or solvate thereof:

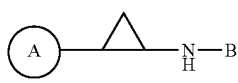

(I)

wherein:
A is cyclyl optionally having 1, 2, 3, or 4 substituents A';
each A' is independently selected from -$L^1$-cyclyl, alkyl, alkenyl, alkynyl, alkoxy, amino, amido, -$CH_2$-CO-$NH_2$, alkylamino, hydroxyl, nitro, halo, haloalkyl, haloalkoxy, cyano, sulfonyl, sulfinyl, sulfonamide, acyl, carboxyl, carbamate and urea, wherein the cyclyl moiety comprised in said -$L^1$-cyclyl is optionally further substituted with one or more groups independently selected from halo, haloalkyl, haloalkoxy, aryl, arylalkoxy, aryloxy, arylalkyl, alkyl, alkenyl, alkynyl, alkoxy, amino, amido, alkylamino, hydroxyl,
nitro, -$CH_2$-CO-$NH_2$, heteroaryl, heteroarylalkoxy, heteroaryloxy, heteroarylalkyl, cyano, sulfonyl, sulfinyl, sulfonamide, acyl, carboxyl, carbamate and urea;
each $L^1$ is independently selected from a covalent bond, -$(CH_2)_{1-6}$-, -$(CH_2)_{0-3}$-O-$(CH_2)_{0-3}$-, -$(CH_2)_{0-3}$-NH-$(CH_2)_{0-3}$- and -$(CH_2)_{0-3}$-S-$(CH_2)_{0-3}$-;
B is -$L^2$-cyclyl, -H, -$L^2$-CO-$NH_2$, -$L^2$-CO-$NR^1R^2$ or -$L^2$-CO-$R^3$, wherein the cyclyl moiety in said -$L^2$-cyclyl is aryl, cycloalkyl or heterocycloalkyl, and wherein the cyclyl moiety in said -$L^2$-cyclyl is optionally substituted with one or more groups independently selected from halo, haloalkyl, haloalkoxy, haloaryl, arylalkoxy, aryloxy, arylalkyl, alkyl, alkenyl, alkynyl, alkoxy, amino, amido, alkylamino, hydroxyl, nitro, -$CH_2$-CO-$NH_2$, heteroaryl, heteroarylalkoxy, heteroaryloxy, heteroarylalkyl, cycloalkyl, cycloalkylalkoxy, cycloalkoxy, cycloalkylalkyl, heterocycloalkyl, heterocycloalkylalkoxy, heterocycloalkoxy, heterocycloalkylalkyl, cyano, cyanato, isocyanato, thiocyanato, isothiocyanato, sulfonyl, sulfinyl, sulfonamide, trihalomethanesulfonamido, acyl, acylamino, acyloxy, alkylthio, cycloalkylthio, heterocycloalkylthio, arylthio, heteroarylthio, carboxyl, carbamate and urea;
$R^1$ and $R^2$ are each independently selected from —H, alkyl, alkynyl, alkenyl, -L-carbocycle, -L-aryl, and -L-heterocyclyl, wherein said alkyl, said alkynyl or said alkenyl is optionally substituted with one or more groups independently selected from halo, haloalkoxy, haloaryl, aryl, arylalkoxy, aryloxy, alkoxy, amino, amido, alkylamino, hydroxyl, nitro, -$CH_2$-CO-$NH_2$, heteroaryl, heteroarylalkoxy, heteroaryloxy, cycloalkyl, cycloalkylalkoxy, cycloalkoxy, heterocycloalkyl, heterocycloalkylalkoxy, heterocycloalkoxy, cyano, cyanato, isocyanato, thiocyanato, isothiocyanato, sulfonyl, sulfinyl, sulfonamide, trihalomethanesulfonamido, acyl, acylamino, acyloxy, alkylthio, cycloalkylthio, heterocycloalkylthio, arylthio, heteroarylthio, carboxyl, carbamate and urea, and further wherein the carbocycle moiety in said -L-carbocycle, the aryl moiety in said -L-aryl, or the heterocyclyl moiety in said -L-heterocyclyl is optionally substituted with one or more groups independently selected from halo, haloalkyl, haloalkoxy, haloaryl, aryl, arylalkoxy, aryloxy, arylalkyl, alkyl, alkenyl, alkynyl, alkoxy, amino, amido, alkylamino, hydroxyl, nitro, -$CH_2$-CO-$NH_2$, heteroaryl, heteroarylalkoxy, heteroaryloxy, heteroarylalkyl, cycloalkyl, cycloalkylalkoxy, cycloalkoxy, cycloalkylalkyl, heterocycloalkyl, heterocycloalkylalkoxy, heterocycloalkoxy, heterocycloalkylalkyl, cyano, cyanato, isocyanato, thiocyanato, isothiocyanato, sulfonyl, sulfinyl, sulfonamide, trihalomethanesulfonamido, acyl, acylamino, acyloxy, alkylthio, cycloalkylthio, heterocycloalkylthio, arylthio, heteroarylthio, carboxyl, carbamate and urea;
$R^3$ is selected from —H, alkoxy, -L-carbocyclic, -L-heterocyclic, and —L-aryl, wherein the carbocyclic moiety in said —L-carbocyclic, the heterocyclic moiety in said -L-heterocyclic, or the aryl moiety in said -L-aryl is optionally substituted with one or more groups independently selected from halo, haloalkyl, haloalkoxy, haloaryl, aryl, arylalkoxy, aryloxy, arylalkyl, alkyl, alkenyl, alkynyl, alkoxy, amino, amido, alkylamino, hydroxyl, nitro, -$CH_2$-CO-$NH_2$, heteroaryl, heteroarylalkoxy, heteroaryloxy, heteroarylalkyl, cycloalkyl, cycloalkylalkoxy, cycloalkoxy, cycloalkylalkyi, heterocycloalkyl, heterocycloalkylalkoxy, heterocycloalkoxy, heterocycloalkylalkyl, cyano, cyanato, isocyanato, thiocyanato, isothiocyanato, sulfonyl, sulfinyl, sulfonamide, trihalomethanesulfonamido, acyl, acylamino, acyloxy, alkylthio, cycloalkylthio, heterocycioalkylthio, arylthio, heteroarylthio, carboxyl, carbamate and urea;
each L is independently selected from -$(CH_2)_n$-$(CH_2)_n$-, -$(CH_2)_nC(=O)(CH_2)_n$-, -$(CH_2)_nC(=O)NH(CH_2)_n$-, -$(CH_2)NHC(=O)O(CH_2)_n$-, -$(CH_2)_nNHC(=O)NH(CH_2)_n$-, -$(CH_2)_nNHC(=S)S(CH_2)_n$-, -$(CH_2)_nOC(=O)S(CH_2)_n$-,- $(CH_2)_nNH(CH_2)_n$-, -$(CH_2)_nO(CH_2)_n$-, -$(CH_2)_nS(CH_2)_n$-, and -$(CH_2)_nNHC(=S)NH(CH_2)_n$-, wherein each n is independently selected from 0, 1, 2, 3, 4, 5, 6, 7, and 8; and
$L^2$ is $C_{1-12}$ alkylene which is optionally interrupted by one or more groups independently selected from -O-, -S-, -NH-, -N(alkyl)-, -CO-, -CO-NH- and -CO-N(alkyl)-.

2. The method of claim 1 wherein said Flaviviridae is Hepatitis C virus, Yellow fever virus, West Nile Virus, Dengue Virus, or Japanese encephalitis virus.

3. A method of treating a symptom of Hepatitis C virus infection or a liver disease in an individual infected with Hepatitis C virus, the method comprising administering to an individual in need of such treatment a Lysine Specific Demethylase-1 (LSD1) inhibitor, wherein said LSD1 inhibitor is a 2-cyclylcyclopropan-1-amine compound of formula (I) or an enantiomer, a diastereomer, or a racemic mixture thereof, or a pharmaceutically acceptable salt or solvate thereof:

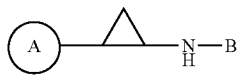

wherein:
A is cyclyl optionally having 1, 2, 3, or 4 substituents A';
each A' is independently selected from -L$^1$-cyclyl, alkyl, alkenyl, alkynyl, alkoxy, amino, amido, -CH$_2$-CO-NH$_2$, alkylamino, hydroxyl, nitro, halo, haloalkyl, haloalkoxy, cyano, sulfonyl, sulfinyl, sulfonamide, acyl, carboxyl, carbamate and urea, wherein the cyclyl moiety comprised in said -L$^1$-cyclyl is optionally further substituted with one or more groups independently selected from halo, haloalkyl, haloalkoxy, aryl, arylalkoxy, aryloxy, arylalkyl, alkyl, alkenyl, alkynyl, alkoxy, amino, amido, alkylamino, hydroxyl,
nitro, -CH$_2$-CO-NH$_2$, heteroaryl, heteroarylalkoxy, heteroaryloxy, heteroarylalkyl, cyano, sulfonyl, sulfinyl, sulfonamide, acyl, carboxyl, carbamate and urea;
each L$^1$ is independently selected from a covalent bond, -(CH$_2$)$_{1-6}$-, -(CH$_2$)$_{0-3}$-O-(CH$_2$)$_{0-3}$-, -(CH$_2$)$_{0-3}$-NH-(CH$_2$)$_{0-3}$- and -(CH$_2$)$_{0-3}$-S-(CH$_2$)$_{0-3}$-;
B is -L$^2$-cyclyl, -H, -L$^2$-CO-NH$_2$, -L$^2$-CO-NR$^1$R$^2$ or -L$^2$-CO-R$^3$, wherein the cyclyl moiety in said -L$^2$-cyclyl is aryl, cycloalkyl or heterocycoloalkyl, and wherein the cyclyl moiety in said -L$^2$-cyclyl is optionally substituted with one or more groups independently selected from halo, haloalkyl, haloalkoxy, haloaryl, arylalkoxy, aryloxy, arylalkyl, alkyl, alkenyl, alkynyl, alkoxy, amino, amido, alkylamino, hydroxyl, nitro, -CH$_2$-CO-NH$_2$, heteroaryl, heteroarylalkoxy, heteroaryloxy, heteroarylalkyl, cycloalkyl, cycloalkylalkoxy, cycloalkoxy, cycloalkylalkyl, heterocycloalkyl, heterocycloalkylalkoxy, heterocycloalkoxy, heterocycloalkylalkyl, cyano, cyanato, isocyanato, thiocyanato, isothiocyanato, sulfonyl, sulfinyl, sulfonamide, trihalomethanesulfonamido, acyl, acylamino, acyloxy, alkylthio, cycloalkylthio, heterocycloalkylthio, arylthio, heteroarylthio, carboxyl, carbamate and urea;
R$^1$ and R$^2$ are each independently selected from —H, alkyl, alkynyl, alkenyl, -L-carbocycle, -L-aryl, and -L-heterocyclyl, wherein said alkyl, said alkynyl or said alkenyl is optionally substituted with one or more groups independently selected from halo, haloalkoxy, haloaryl, aryl, arylalkoxy, aryloxy, alkoxy, amino, amido, alkylamino, hydroxyl, nitro, -CH$_2$-CO-NH$_2$, heteroaryl, heteroarylalkoxy, heteroaryloxy, cycloalkyl, cycloalkylalkoxy, cycloalkoxy, heterocycloalkyl, heterocycloalkylalkoxy, heterocycloalkoxy, cyano, cyanato, isocyanato, thiocyanato, isothiocyanato, sulfonyl, sulfinyl, sulfonamide, trihalomethanesulfonamido, acyl, acylamino, acyloxy, alkylthio, cycloalkylthio, heterocycloalkylthio, arylthio, heteroarylthio, carboxyl, carbamate and urea, and further wherein the carbocycle moiety in said -L-carbocycle, the aryl moiety in said -L-aryl, or the heterocyclyl moiety in said -L-heterocyclyl is optionally substituted with one or more groups independently selected from halo, haloalkyl, haloalkoxy, haloaryl, aryl, arylalkoxy, aryloxy, arylalkyl, alkyl, alkenyl, alkynyl, alkoxy, amino, amido, alkylamino, hydroxyl, nitro, -CH$_2$-CO-NH$_2$, heteroaryl, heteroarylalkoxy, heteroaryloxy, heteroarylalkyl, cycloalkyl, cycloalkylalkoxy, cycloalkoxy, cycloalkylalkyl, heterocycloalkyl, heterocycloalkylalkoxy, heterocycloalkoxy, heterocycloalkylalkyl, cyano, cyanato, isocyanato, thiocyanato, isothiocyanato, sulfonyl, sulfinyl, sulfonamide, trihalomethanesulfonamido, acyl, acylamino, acyloxy, alkylthio, cycloalkylthio, heterocycloalkylthio, arylthio, heteroarylthio, carboxyl, carbamate and urea;
R$^3$ is selected from —H, alkoxy, -L-carbocyclic, -L-heterocyclic, and —L-aryl, wherein the carbocyclic moiety in said —L-carbocyclic, the heterocyclic moiety in said -L-heterocyclic, or the aryl moiety in said -L-aryl is optionally substituted with one or more groups independently selected from halo, haloalkyl, haloalkoxy, haloaryl, aryl, arylalkoxy, aryloxy, arylalkyl, alkyl, alkenyl, alkynyl, alkoxy, amino, amido, alkylamino, hydroxyl, nitro, -CH$_2$-CO-NH$_2$, heteroaryl, heteroarylalkoxy, heteroaryloxy, heteroarylalkyl, cycloalkyl, cycloalkylalkoxy, cycloalkoxy, cycloalkylalkyl, heterocycloalkyl, heterocycloalkylalkoxy, heterocycloalkoxy, heterocycloalkylalkyl, cyano, cyanato, isocyanato, thiocyanato, isothiocyanato, sulfonyl, sulfinyl, sulfonamide, trihalomethanesulfonamido, acyl, acylamino, acyloxy, alkylthio, cycloalkylthio, heterocycioalkylthio, arylthio, heteroarylthio, carboxyl, carbamate and urea;
each L is independently selected from -(CH$_2$)$_n$-(CH$_2$)$_n$-, -(CH$_2$)$_n$C(=O)(CH$_2$)$_n$-, -(CH$_2$)$_n$C(=O)NH(CH$_2$)$_n$-, -(CH$_2$)$_n$NHC(=O)O(CH$_2$)$_n$-, -(CH$_2$)$_n$NHC(=O)NH(CH$_2$)$_n$-, -(CH$_2$)$_n$NHC(=S)S(CH$_2$)$_n$-, -(CH$_2$)$_n$OC(=O)S(CH$_2$)$_n$-, -(CH$_2$)$_n$NH(CH$_2$)$_n$-, -(CH$_2$)$_n$O(CH$_2$)$_n$-, -(CH$_2$)$_n$S(CH$_2$)$_n$-, and -(CH$_2$)$_n$NHC(=S)NH(CH$_2$)$_n$-, wherein each n is independently selected from 0, 1, 2, 3, 4, 5, 6, 7, and 8; and
L$^2$ is C$_{1-12}$ alkylene which is optionally interrupted by one or more groups independently selected from -O-, -S-, -NH-, -N(alkyl)-, -CO-, -CO-NH- and -CO-N(alkyl)-.

4. A method of treating Hepatitis C Virus (HCV) and Hepatitis B Virus (HBV) co-infection comprising administering to an individual in need of such treatment a Lysine Specific Demethylase-1 (LSD1) inhibitor and optionally a second anti-HCV agent or anti-HBV agent, wherein said LSD1 inhibitor is a 2-cyclylcyclopropan-1-amine compound of formula (I) or an enantiomer, a diastereomer, or a racemic mixture thereof, or a pharmaceutically acceptable salt or solvate thereof:

wherein:
A is cyclyl optionally having 1, 2, 3, or 4 substituents A';
each A' is independently selected from -L$^1$-cyclyl, alkyl, alkenyl, alkynyl, alkoxy, amino, amido, -CH$_2$-CO-NH$_2$, alkylamino, hydroxyl, nitro, halo, haloalkyl, haloalkoxy, cyano, sulfonyl, sulfinyl, sulfonamide, acyl, carboxyl, carbamate and urea, wherein the cyclyl moiety comprised in said -L$^1$-cyclyl is optionally further substituted with one or more groups independently selected from halo, haloalkyl, haloalkoxy, aryl, arylalkoxy, aryloxy, arylalkyl, alkyl, alkenyl, alkynyl, alkoxy, amino, amido, alkylamino, hydroxyl,
nitro, -CH$_2$-CO-NH$_2$, heteroaryl, heteroarylalkoxy, heteroaryloxy, heteroarylalkyl, cyano, sulfonyl, sulfinyl, sulfonamide, acyl, carboxyl, carbamate and urea;

each $L^1$ is independently selected from a covalent bond, -(CH$_2$)$_{1-6}$-, -(CH$_2$)$_{0-3}$-O-(CH$_2$)$_{0-3}$-, -(CH$_2$)$_{0-3}$-NH-(CH$_2$)$_{0-3}$- and -(CH$_2$)$_{0-3}$-S-(CH$_2$)$_{0-3}$-;

B is -L$^2$-cyclyl, -H, -L$^2$-CO-NH$_2$, -L$^2$-CO-NR$^1$R$^2$ or -L$^2$-CO-R$^3$, wherein the cyclyl moiety in said -L$^2$-cyclyl is aryl, cycloalkyl or heterocycoloalkyl, and wherein the cyclyl moiety in said -L$^2$-cyclyl is optionally substituted with one or more groups independently selected from halo, haloalkyl, haloalkoxy, haloaryl, arylalkoxy, aryloxy, arylalkyl, alkyl, alkenyl, alkynyl, alkoxy, amino, amido, alkylamino, hydroxyl, nitro, -CH$_2$-CO-NH$_2$, heteroaryl, heteroarylalkoxy, heteroaryloxy, heteroarylalkyl, cycloalkyl, cycloalkylalkoxy, cycloalkoxy, cycloalkylalkyl, heterocycloalkyl, heterocycloalkylalkoxy, heterocycloalkoxy, heterocycloalkylalkyl, cyano, cyanato, isocyanato, thiocyanato, isothiocyanato, sulfonyl, sulfinyl, sulfonamide, trihalomethanesulfonamido, acyl, acylamino, acyloxy, alkylthio, cycloalkylthio, heterocycloalkylthio, arylthio, heteroarylthio, carboxyl, carbamate and urea;

R$^1$ and R$^2$ are each independently selected from —H, alkyl, alkynyl, alkenyl, -L-carbocycle, -L-aryl, and -L-heterocyclyl, wherein said alkyl, said alkynyl or said alkenyl is optionally substituted with one or more groups independently selected from halo, haloalkoxy, haloaryl, aryl, arylalkoxy, aryloxy, alkoxy, amino, amido, alkylamino, hydroxyl, nitro, -CH$_2$-CO-NH$_2$, heteroaryl, heteroarylalkoxy, heteroaryloxy, cycloalkyl, cycloalkylalkoxy, cycloalkoxy, heterocycloalkyl, heterocycloalkylalkoxy, heterocycloalkoxy, cyano, cyanato, isocyanato, thiocyanato, isothiocyanato, sulfonyl, sulfinyl, sulfonamide, trihalomethanesulfonamido, acyl, acylamino, acyloxy, alkylthio, cycloalkylthio, heterocycloalkylthio, arylthio, heteroarylthio, carboxyl, carbamate and urea, and further wherein the carbocycle moiety in said -L-carbocycle, the aryl moiety in said -L-aryl, or the heterocyclyl moiety in said -L-heterocyclyl is optionally substituted with one or more groups independently selected from halo, haloalkyl, haloalkoxy, haloaryl, aryl, arylalkoxy, aryloxy, arylalkyl, alkyl, alkenyl, alkynyl, alkoxy, amino, amido, alkylamino, hydroxyl, nitro, -CH$_2$-CO-NH$_2$, heteroaryl, heteroarylalkoxy, heteroaryloxy, heteroarylalkyl, cycloalkyl, cycloalkylalkoxy, cycloalkoxy, cycloalkylalkyl, heterocycloalkyl, heterocycloalkylalkoxy, heterocycloalkoxy, heterocycloalkylalkyl, cyano, cyanato, isocyanato, thiocyanato, isothiocyanato, sulfonyl, sulfinyl, sulfonamide, trihalomethanesulfonamido, acyl, acylamino, acyloxy, alkylthio, cycloalkylthio, heterocycloalkylthio, arylthio, heteroarylthio, carboxyl, carbamate and urea;

R$^3$ is selected from —H, alkoxy, -L-carbocyclic, -L-heterocyclic, and —L-aryl, wherein the carbocyclic moiety in said —L-carbocyclic, the heterocyclic moiety in said -L-heterocyclic, or the aryl moiety in said -L-aryl is optionally substituted with one or more groups independently selected from halo, haloalkyl, haloalkoxy, haloaryl, aryl, arylalkoxy, aryloxy, arylalkyl, alkyl, alkenyl, alkynyl, alkoxy, amino, amido, alkylamino, hydroxyl, nitro, -CH$_2$-CO-NH$_2$, heteroaryl, heteroarylalkoxy, heteroaryloxy, heteroarylalkyl, cycloalkyl, cycloalkylalkoxy, cycloalkoxy, cycloalkylalkyl, heterocycloalkyl, heterocycloalkylalkoxy, heterocycloalkoxy, heterocycloalkylalkyl, cyano, cyanato, isocyanato, thiocyanato, isothiocyanato, sulfonyl, sulfinyl, sulfonamide, trihalomethanesulfonamido, acyl, acylamino, acyloxy, alkylthio, cycloalkylthio, heterocycioalkylthio, arylthio, heteroarylthio, carboxyl, carbamate and urea;

each L is independently selected from -(CH$_2$)$_n$-(CH$_2$)$_n$-, -(CH$_2$)$_n$C(=O)(CH$_2$)$_n$-, -(CH$_2$)$_n$C(=O)NH(CH$_2$)$_n$-, -(CH$_2$)$_n$NHC(=O)O(CH$_2$)$_n$-, -(CH$_2$)$_n$NHC(=O)NH(CH$_2$)$_n$-, -(CH$_2$)$_n$NHC(=S)S(CH$_2$)$_n$-, -(CH$_2$)$_n$OC(=O)S(CH$_2$)$_n$-, (CH$_2$)$_n$NH(CH$_2$)$_n$-, -(CH$_2$)$_n$O(CH$_2$)$_n$-, -(CH$_2$)$_n$S(CH$_2$)$_n$-, and -(CH$_2$)$_n$NHC(=S)NH(CH$_2$)$_n$-, wherein each n is independently selected from 0, 1, 2, 3, 4, 5, 6, 7, and 8; and L$^2$ is C$_{1-12}$ alkylene which is optionally interrupted by one or more groups independently selected from -O-, -S-, -NH-, -N(alkyl)-, -CO-, -CO-NH- and -CO-N(alkyl)-.

5. The method of claim 1, wherein A is aryl or heteroaryl and wherein A is unsubstituted or has 1 or 2 substituents A'.

6. The method of claim 5, wherein A is phenyl, pyridinyl, pyrimidinyl, thiophenyl, benzothiophenyl, pyrrolyl, indolyl, furanyl, or thiazolyl, and wherein A is unsubstituted or has 1 or 2 substituents A'.

7. The method of claim 1, wherein B is -L$^2$-cyclyl, wherein the cyclyl moiety in said -L$^2$-cyclyl is aryl, cycloalkyl or heterocycloalkyl, and further wherein the cyclyl moiety in said -L$^2$-cyclyl is optionally substituted with one or more groups independently selected from halo, haloalkyl, haloalkoxy, haloaryl, aryl, arylalkoxy, aryloxy, arylalkyl, alkyl, alkenyl, alkynyi, alkoxy, amino, amido, alkylamino, hydroxyl, nitro, -CH$_2$-CO-NH$_2$, heteroaryl, heteroaryialkoxy, heteroaryloxy, heteroarylalkyl, cycloalkyl, cycloalkylalkoxy, cycloalkoxy, cycloalkylaikyl, heterocycloalkyl, heterocycloalkylalkoxy, heterocycloalkoxy, heterocycloalkylalkyl, cyano, cyanato, isocyanato, thiocyanato, isothiocyanato, sulfonyl, suifinyl, sulfonamide, trihalomethanesulfonamido, acyl, acylamino, acyloxy, alkyithio, cycloalkylthio, heterocycloalkylthio, arylthio, heteroarylthio, carboxyl, carbamate, and urea.

8. The method of claim 7, wherein the cyclyl moiety in said -L$^2$-cyclyl is aryl or cycloalkyl.

9. The method of claim 7, wherein the cyclyl moiety in said -L$^2$-cyclyl is heterocycloalkyl.

10. The method of claim 1, wherein L$^2$ is -(CH$_2$)$_{1-4}$- or -CH$_2$-CO-.

11. The method of claim 1, wherein B is -H.

12. The method of claim 1, wherein B is -(CH$_2$)$_{1-4}$-CO-NH$_2$, -(CH$_2$)$_{1-4}$-CO-NR$^1$R$^2$ or -(CH$_2$)$_{1-4}$-CO-R$^3$.

13. The method of claim 1, wherein the substituents on the cyclopropane ring are in trans configuration.

14. The method of claim 7, wherein L$^2$ is -(CH$_2$)$_{1-4}$- or -CH$_2$-CO-.

15. The method of claim 1 wherein said Flaviviridae infection is Hepatitis C virus.

* * * * *